(12) United States Patent
Sato et al.

(10) Patent No.: US 9,475,752 B2
(45) Date of Patent: Oct. 25, 2016

(54) METHOD FOR MANUFACTURING 3,4,5-TRICAFFEOYLQUINIC ACID

(71) Applicant: FUJIFILM Corporation, Tokyo (JP)

(72) Inventors: Kozo Sato, Ashigara-kami-gun (JP); Hiroyuki Naito, Ashigara-kami-gun (JP); Takeshi Murakami, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/876,931

(22) Filed: Oct. 7, 2015

(65) Prior Publication Data

US 2016/0023986 A1  Jan. 28, 2016

Related U.S. Application Data

(63) Continuation of application No. PCT/JP2014/060176, filed on Apr. 8, 2014.

(30) Foreign Application Priority Data

| Apr. 8, 2013 | (JP) | ................ | 2013-080214 |
| Apr. 19, 2013 | (JP) | ................ | 2013-088550 |
| Sep. 30, 2013 | (JP) | ................ | 2013-203423 |

(51) Int. Cl.

| C07C 69/732 | (2006.01) |
| C07C 67/14 | (2006.01) |
| C07C 67/24 | (2006.01) |
| C07C 67/31 | (2006.01) |
| C07C 68/06 | (2006.01) |
| C07C 69/96 | (2006.01) |

(52) U.S. Cl.
CPC ............ *C07C 69/732* (2013.01); *C07C 67/14* (2013.01); *C07C 67/24* (2013.01); *C07C 67/31* (2013.01); *C07C 68/06* (2013.01); *C07C 69/96* (2013.01); *C07C 2101/14* (2013.01)

(58) Field of Classification Search
None
See application file for complete search history.

(56) References Cited

FOREIGN PATENT DOCUMENTS

JP    2005298382 A    10/2005

OTHER PUBLICATIONS

Miyamae et al. (Chem. Pharm. Bull., 2011, 59(4), 502-507).*
The Food Industry: 48(6), pp. 71-74, Mar. 30, 2005, in English with pp. 69-75 in Japanese.
Shokuhin to Gijutsu (Food and Technologies), pp. 11-15, Aug. 1, 2008, Japan Food Industry Association, in English and pp. 10-18 in Japanese.

Miyamae et al., "Structure-Activity Relationship of Caffeoylquinic Acids on the Accelerating Activity on ATP Production," Chem. Pharm. Bull., 59(4), Jan. 13, 2011, pp. 502-507, particularly p. 504, chart 3.
Haslam et al., "407. Gallotannins. Part VIII. The Preparation and Properties of Some Galloyl Esters of Quinic Acid," Journal of the Chemical Society, Apr. 1, 1963, pp. 2173-2181, particularly p. 2180, lines 31-42.
Panizzi et al., "Synthesis of chlorogenic acid," Gazz. Chim. Ital., Jan. 1, 1956, vol. 86, pp. 913-922, Chemical Abstracts, 1959, vol. 53, col. 258b-e.
International Preliminary Report on Patentability and Written Opinion, mailed Oct. 22, 2015, issued in corresponding International Application No. PCT/JP2014/060176, 7 pages.
Communication dated Apr. 26, 2016, from the State Intellectual Property Office of People's Republic of China in counterpart Application No. 201480020134.8.
"Design, Synthesis and Biological Activity Study of Caffeoylquinic Acid Derivatives", Li-juan Zhang, China Masters' Theses Full-text Database, Medical Science and Technology Reports, 2009(6), Jun. 15, 2009; 90 pages total.

* cited by examiner

*Primary Examiner* — Yevegeny Valenrod
(74) *Attorney, Agent, or Firm* — Sughrue Mion, PLLC

(57) ABSTRACT

Provided are a method for manufacturing 3,4,5-tricaffeoylquinic acid, which can produce 3,4,5-tricaffeoylquinic acid with high efficiency by a simple operation in a short process using inexpensive raw materials, and intermediate compounds. The method for manufacturing 3,4,5-tricaffeoylquinic acid of the invention includes at least Step (1) of allowing a compound represented by Formula (1) or a compound represented by Formula (2) to react with a compound represented by Formula (4); and Step (2) of deprotecting the product obtained in Step (1), and producing 3,4,5-tricaffeoylquinic acid:

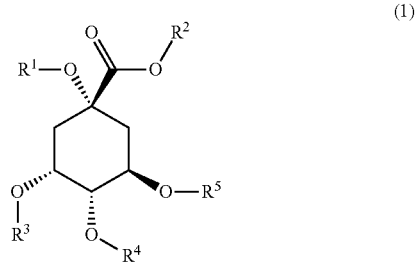

(1)

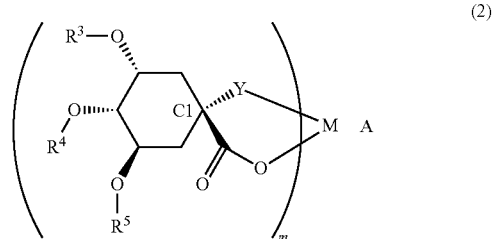

(2)

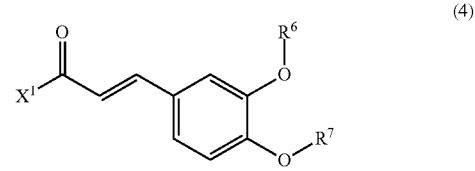

(4)

13 Claims, 11 Drawing Sheets

METHOD FOR MANUFACTURING 3,4,5-TRICAFFEOYLQUINIC ACID

CROSS REFERENCE TO RELATED APPLICATIONS

This application is a continuation of PCT International Application No. PCT/JP2014/060176 filed on Apr. 8, 2014, which claims priority under 35 U.S.C. §119(a) to Japanese Patent Application No. 2013-080214 filed on Apr. 8, 2013, Japanese Patent Application No. 2013-088550 filed on Apr. 19, 2013, and Japanese Patent Application No. 2013-203423 filed on Sep. 30, 2013. Each of the above applications is hereby expressly incorporated by reference, in its entirety, into the present application.

BACKGROUND OF THE INVENTION

The present invention relates to a method for manufacturing 3,4,5-tricaffeoylquinic acid.

In recent years, research and development on the utilization of plant resources is being conducted in a variety of fields have been performed.

Among them, polyphenols in particular are attracting attention from the viewpoint of health care, and various polyphenols are extracted from plants and are utilized in various applications. For example, it has been reported that sweet potato-derived polyphenols are effective in diseases and beauty care, such as cancers, diabetes mellitus, hypertension, Alzheimer's disease, HIV, and melanogenesis inhibition (Shokuhin Kogyo (Food Industry), Vol. 3 (2005), pp. 1-7 (Shokuhin Gijutsu Tosho Shuppan)).

Chlorogenic acids, which constitute one class of polyphenols, are contained in coffee beans, sweet potato leaves, mugwort, honeysuckle, sunflower, and the like, and chlorogenic acids have been extracted from plants using hot water or ethanol. However, it has been extremely difficult to purify chlorogenic acids to such a high extent that the purified chlorogenic acids can be utilized as pharmaceutical products.

3,4,5-Tricaffeoylquinic acid has the highest physiological activity among chlorogenic acids, and it has been reported that this acid has various physiological activities such as strong antitumor action, antidiabetic action, antihypertensive action, and antiviral action (Shokuhin to Gijutsu (Food and Technologies), Vol. 8 (2008), pp. 10-18 (Japan Food Industry Center)). 3,4,5-Tricaffeoylquinic acid is obtained by extracting the acid from the stems and leaves of sweet potato or Brazilian propolis using an alcohol, subsequently degreasing the extract with hexane, and fractionating the acid by adsorption chromatography and gel filtration chromatography (JP 2005-298382A).

However, the amount of 3,4,5-tricaffeoylquinic acid contained in plants and the like is so small that, in order to obtain highly pure 3,4,5-tricaffeoylquinic acid, a complicated and long purification process is required. In spite of having attractive physiological activity, it has been difficult to apply 3,4,5-tricaffeoylquinic acid to practical applications.

On the other hand, synthesis of 3,4,5-tricaffeoylquinic acid has been investigated, and the complete synthesis was reported for the first time in Chem. Pharm. Bull., Vol. 59 (2011), pp. 502-507.

SUMMARY OF THE INVENTION

However, the method described in Chem. Pharm. Bull., Vol. 59 (2011), pp. 502-507 has various problems such as that the process is long, the operation is complicated, expensive reagents are needed, cryogenic reaction conditions are needed, and a markedly long time is required for the detachment of protective groups in the final step.

Under such circumstances, an object of the present invention is to provide a method for manufacturing 3,4,5-tricaffeoylquinic acid, the method being capable of producing 3,4,5-tricaffeoylquinic acid with high efficiency by a short process and a simple operation using inexpensive raw materials.

The inventors of the present invention conducted thorough investigations, and as a result, the inventors found a novel method for manufacturing 3,4,5-tricaffeoylquinic acid, thus completing the invention.

That is, the inventors found that the object described above can be achieved by the following constitution.

(1) A method for manufacturing 3,4,5-tricaffeoylquinic acid, the method including at least Step (1) of allowing a compound represented by Formula (1) described below or a compound represented by Formula (2) described below to react with a compound represented by Formula (4) described below; and Step (2) of deprotecting the product obtained in Step (1), and producing 3,4,5-tricaffeoylquinic acid represented by Formula (6) described below.

(2) The method according to (1), in which Step (1) is carried out in the presence of a solvent having a SP value of 8.0 to 10.0.

(3) The method according to (1) or (2), in which the temperature of the reaction for Step (1) is −10° C. to 30° C.

(4) The method according to any one of (1) to (3), in which a compound represented by Formula (1a) described below is used in Step (1), and the method includes, before Step (1), Step (3) of allowing a compound represented by Formula (A3) described below to react with a compound represented by Formula (A5) described below, and thereby obtaining the compound represented by Formula (1a) described below.

(5) The method according to any one of (1) to (4), in which $X^1$ represents a halogen atom.

(6) The method according to any one of (1) to (5), in which $X^1$ represents a chlorine atom.

(7) The method according to any one of (1) to (6), in which $R^1$ represents a hydroxyl protective group, and $R^2$ represents a carboxyl protective group.

(8) The method according to any one of (1) to (7), in which $R^1$ represents a $C_{1-6}$ alkoxycarbonyl group which may be substituted, an aryloxycarbonyl group which may be substituted, or an acyl group which may be substituted, and $R^2$ represents a $C_{1-6}$ alkyl group which may be substituted, or a $C_{2-6}$ alkenyl group which may be substituted.

(9) The method according to any one of (1) to (8), in which $R^1$ represents a $C_{1-6}$ alkoxycarbonyl group which may be substituted with a halogen atom, and $R^2$ represents a $C_{1-6}$ alkyl group which may be substituted with a halogen atom.

(10) The manufacturing method according to any one of (1) to (9), in which $R^6$ and $R^7$, which are identical or different, each represent a $C_{1-6}$ alkoxycarbonyl group which may be substituted, an aryloxycarbonyl group which may be substituted, or an acyl group which may be substituted.

(11) The method according to any one of (1) to (10), in which $R^6$ and $R^7$, which are identical or different, each represent a $C_{1-6}$ alkoxycarbonyl group which may be substituted with a halogen atom.

(12) The method according to any one of (1) to (11), in which $R^3$, $R^4$, and $R^5$ each represent a hydrogen atom.

(13) A compound represented by Formula (1-1) described below, or a salt thereof.

(14) The compound according to (13), or a salt thereof, in which $R^{1a}$ represents a $C_{1-6}$ alkoxycarbonyl group which may be substituted, an aryloxycarbonyl group which may be substituted, or an acyl group which may be substituted, and $R^{2a}$ represents a $C_{1-6}$ alkyl group which may be substituted, or a $C_{2-6}$ alkenyl group which may be substituted.

(15) The compound according to (13) or (14), or a salt thereof, in which $R^{1a}$ represents a $C_{1-6}$ alkoxycarbonyl group which may be substituted with a halogen atom, and $R^{2a}$ represents a $C_{1-6}$ alkyl group which may be substituted with a halogen atom.

(16) The compound according to any one of (13) to (15), or a salt thereof, in which $R^6$ and $R^7$, which are identical or different, each represent a $C_{1-6}$ alkoxycarbonyl group which may be substituted, an aryloxycarbonyl group which may be substituted, or an acyl group which may be substituted.

(17) The compound according to any one of (13) to (16), or a salt thereof, in which $R^6$ and $R^7$, which are identical or different, each represent a $C_{1-6}$ alkoxycarbonyl group which may be substituted with a halogen atom.

(18) The compound according to any one of (13) to (17), or a salt thereof, in which $R^3$, $R^4$, and $R^5$ each represent a hydrogen atom.

According to the invention, a manufacturing method which can produce a large quantity of 3,4,5-tricaffeoylquinic acid of high purity with high efficiency, by a short process and a simple operation using inexpensive raw materials, can be provided.

DETAILED DESCRIPTION OF THE INVENTION

Figure 1:
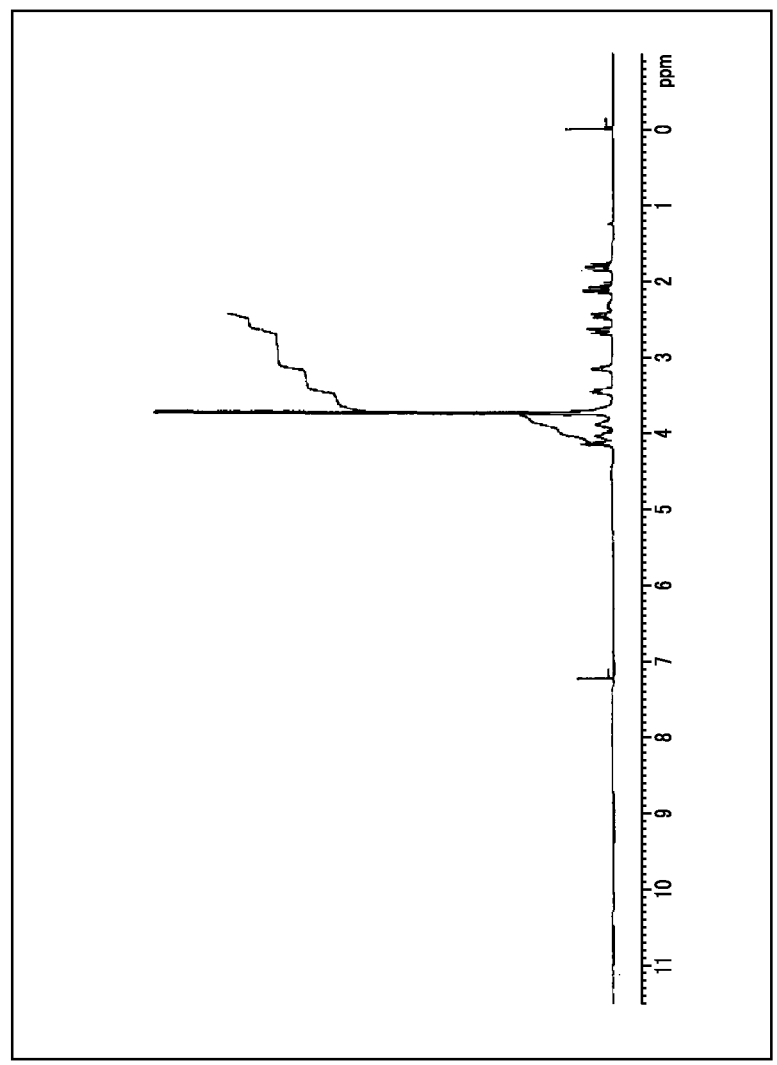
FIG. 1 is the $^1$H-NMR spectrum of 1A synthesized in Synthesis Example 1.

Hereinafter, suitable embodiments of the method for manufacturing 3,4,5-tricaffeoylquinic acid of the present invention (hereinafter, also simply referred to as "manufacturing method of the invention") will be explained in detail.

According to the invention, unless particularly stated otherwise, each term has the following meaning.

A halogen atom means a fluorine atom, a chlorine atom, a bromine atom, or an iodine atom.

A $C_{1-6}$ alkyl group means a linear or branched alkyl group having 1 to 6 carbon atoms, such as a methyl, ethyl, propyl, isopropyl, butyl, sec-butyl, isobutyl, tert-butyl, pentyl, or hexyl group.

A $C_{2-6}$ alkenyl group means a linear or branched alkenyl group having 2 to 6 carbon atoms, such as a vinyl, allyl, propenyl, isopropenyl, butenyl, isobutenyl, 1,3-butadienyl, pentenyl, or hexenyl group.

A $C_{2-6}$ alkynyl group means a linear or branched alkynyl group having 2 to 6 carbon atoms, such as an ethynyl, propynyl, butynyl, pentynyl, or hexynyl group.

A $C_{3-8}$ cycloalkyl group means a cycloalkyl group having 3 to 8 carbon atoms, such as a cyclopropyl, cyclobutyl, cyclopentyl, or cyclohexyl group.

An aryl group means a phenyl or naphthyl group, or the like.

An ar-$C_{1-6}$ alkyl group means an ar-$C_{1-6}$ alkyl group such as a benzyl, diphenylmethyl, trityl, phenethyl, or naphthylmethyl group.

A $C_{1-6}$ alkoxy group means a linear or branched alkyloxy group having 1 to 6 carbon atoms, such as a methoxy, ethoxy, propoxy, isopropoxy, butoxy, isobutoxy, sec-butoxy, tert-butoxy, pentyloxy, or hexyloxy group.

An aryloxy group means a phenoxy or naphthyloxy group, or the like.

A $C_{1-6}$ alkoxy-$C_{1-6}$alkyl group means an alkyl group having 1 to 6 carbon atoms substituted with an alkyloxy having 1 to 6 carbon atoms, such as a methoxymethyl or 1-ethoxyethyl group.

A $C_{2-6}$ alkanoyl group means a linear or branched alkanoyl group having 2 to 6 carbon atoms, such as an acetyl, propionyl, valeryl, isovaleryl, or pivaloyl group.

An aroyl group means a benzoyl or naphthoyl group, or the like.

An acyl group means a formyl group, a $C_{2-6}$ alkanoyl group, or an aroyl group.

A $C_{2-6}$ alkanoyloxy group means a linear or branched alkanoyloxy group having 2 to 6 carbon atoms, such as an acetyloxy or propionyloxy group.

An aroyloxy group means a benzoyloxy group, or a naphthoyloxy group.

An acyloxy group means a $C_{2-6}$ alkanoyloxy group or an aroyloxy group.

A $C_{1-6}$ alkoxycarbonyl group means a linear or branched alkyloxycarbonyl group having 1 to 6 carbon atoms, such as a methoxycarbonyl, ethoxycarbonyl, isopropoxycarbonyl, tert-butoxycarbonyl, or 1,1-dimethylpropoxycarbonyl group.

An aryloxycarbonyl group means a phenyloxycarbonyl or naphthyloxycarbonyl group, or the like.

A $C_{1-6}$ alkylsulfonyl group means an alkylsulfonyl group having 1 to 6 carbon atoms, such as a methylsulfonyl, ethylsulfonyl or propylsulfonyl group.

An arylsulfonyl group means a benzenesulfonyl or naphthalenesulfonyl group, or the like.

A $C_{1-6}$ alkylsulfonyloxy group means an alkylsulfonyloxy group having 1 to 6 carbon atoms, such as a methylsulfonyloxy, ethylsulfonyloxy, or propylsulfonyloxy group.

An arylsulfonyloxy group means a benzenesulfonyloxy or naphthalenesulfonyloxy group, or the like.

A $C_{1-3}$ alkylene group means a methylene, ethylene, or propylene group.

A silyl group means a trimethylsilyl, triethylsilyl, or tributylsilyl group.

A di($C_{1-6}$ alkyl)phosphoryl group means a di($C_{1-6}$ alkyl) phosphoryl group such as a dimethylphosphoryl, diethylphosphoryl, or dibutylphosphoryl group.

A diarylphosphoryl group means a diphenylphosphoryl group or the like.

A diarylphosphinyl group means a diphenylphosphinyl group or the like.

A leaving group means a halogen atom, a $C_{1-6}$ alkylsulfonyloxy group, an arylsulfonyloxy group, or the like. These groups may be each substituted with one or more groups selected from Substituent Group A that will be described below.

Amino protective groups include all groups that can be used as conventional protective groups for an amino group, and examples thereof include the groups described in W. Greene, et al., Protective Groups in Organic Synthesis, 4$^{th}$ Ed., pp. 696-926, 2007, John Wiley & Sons, Inc.

Specific examples include an ar-$C_{1-6}$ alkyl group, a $C_{1-6}$ alkoxy-$C_{1-6}$ alkyl group, an acyl group, a $C_{1-6}$ alkoxycarbonyl group, an aryloxycarbonyl group, a $C_{1-6}$ alkylsulfonyl group, an arylsulfonyl group, and a silyl group. These groups may be each substituted with one or more groups selected from the Substituent Group A.

Carboxyl protective groups include all groups that can be used as conventional protective groups for a carboxyl group, and examples thereof include the groups described in W. Greene, et al., Protective Groups in Organic Synthesis, 4$^{th}$ Ed., pp. 533-646, 2007, John Wiley & Sons, Inc.

Specific examples include a $C_{1-6}$ alkyl group, a $C_{2-6}$ alkenyl group, an aryl group, an ar-$C_{1-6}$ alkyl group, a $C_{1-6}$ alkoxy-$C_{1-6}$ alkyl group, and a silyl group. These groups may be each substituted with one or more groups selected from the Substituent Group A that will be described below.

Hydroxyl protective groups include all groups that can be used as conventional protective groups for a hydroxyl group, and examples thereof include the groups described in W. Greene, et al., Protective Groups in Organic Synthesis, 4$^{th}$ Ed., pp. 16-366, 2007, John Wiley & Sons, Inc.

Specific examples include a $C_{1-6}$ alkyl group, a $C_{2-6}$ alkenyl group, an ar-$C_{1-6}$ alkyl group, a $C_{1-6}$ alkoxy-$C_{1-6}$ alkyl group, an acyl group, a $C_{1-6}$ alkoxycarbonyl group, an aryloxycarbonyl group, a $C_{1-6}$ alkylsulfonyl group, an arylsulfonyl group, a di($C_{1-6}$ alkyl)phosphoryl group, a diarylphosphoryl group, a diarylphosphinyl group, a tetrahydrofuranyl group, a tetrahydropyranyl group, and a silyl group. These groups may be each substituted with one or more groups selected from the Substituent Group A that will be described below.

Phenolic hydroxyl protective groups include all groups that can be used as conventional protective groups for a phenolic hydroxyl group, and examples thereof include the groups described in W. Greene, et al., Protective Groups in Organic Synthesis, 4$^{th}$ Ed., pp. 370-424, 2007, John Wiley & Sons, Inc.

Specific examples include a $C_{1-6}$ alkyl group, a $C_{2-6}$ alkenyl group, an ar-$C_{1-6}$ alkyl group, a $C_{1-6}$ alkoxy-$C_{1-6}$ alkyl group, an acyl group, a $C_{1-6}$ alkylsulfonyl group, an arylsulfonyl group, and a silyl group. These groups may be each substituted with one or more groups selected from the Substituent Group A.

Substituent Group A: a halogen atom, a cyano group, a nitro group, an amino group which may be protected, a hydroxyl group which may be protected, a carboxyl group which may be protected, a carbamoyl group which may be substituted with one or more groups selected from Substituent Group B that will be described below, a sulfamoyl group which may be substituted with one or more groups selected from the Substituent Group B, a $C_{1-6}$ alkyl group which may be substituted with one or more groups selected from the Substituent Group B, a $C_{2-6}$ alkenyl group which may be substituted with one or more groups selected from the Substituent Group B, a $C_{2-6}$ alkynyl group which may be substituted with one or more groups selected from the Substituent Group B, a $C_{3-8}$ cycloalkyl group which may be substituted with one or more groups selected from the Substituent Group B, an aryl group which may be substituted with one or more groups selected from the Substituent Group B, a $C_{1-6}$ alkoxy group which may be substituted with one or more groups selected from the Substituent Group B, an aryloxy group which may be substituted with one or more groups selected from the Substituent Group B, an acyl group which may be substituted with one or more groups selected from the Substituent Group B, an acyloxy group which may be substituted with one or more groups selected from the Substituent Group B, a $C_{1-6}$ alkoxycarbonyl group which may be substituted with one or more groups selected from the Substituent Group B, an aryloxycarbonyl group which may be substituted with one or more groups selected from the Substituent Group B, and an oxo group.

Substituent Group B: a halogen atom, a cyano group, a nitro group, an amino group which may be protected, a hydroxyl group which may be protected, a carboxyl group which may be protected, a $C_{1-6}$ alkyl group, an aryl group, a $C_{1-6}$ alkoxy group, and an oxo group.

Examples of an aliphatic hydrocarbon include pentane, hexane, cyclohexane, heptane, and petroleum ether.

Examples of a halogenated hydrocarbon include methylene chloride, chloroform, and 1,2-dichloroethane.

Examples of an alcohol include methanol, ethanol, propanol, 2-propanol, butanol, and 2-methyl-2-propanol.

Examples of an ether include diethyl ether, diisopropyl ether, dioxane, tetrahydrofuran, anisole, ethylene glycol dimethyl ether, diethylene glycol dimethyl ether, and diethylene glycol diethyl ether.

Examples of an ester include methyl acetate, ethyl acetate, propyl acetate, isopropyl acetate, and butyl acetate.

Examples of a ketone include acetone, 2-butanone, and 4-methyl-2-pentanone.

Examples of an amide include N,N-dimethylformamide, N,N-dimethylacetamide, and 1-methyl-2-pyrrolidone.

Examples of a secondary amine include dimethylamine, diethylamine, dipropylamine, dibutylamine, pyrrolidine, piperidine, piperazine, and morpholine.

The $C_{1-6}$ alkyl group, aryl group, or $C_{1-6}$ alkoxy group for $R^a$ may be substituted with one or more groups selected from the Substituent Group A.

The $C_{1-6}$ alkoxycarbonyl group, aryloxycarbonyl group, or acyl group for $R^1$ may be substituted with one or more groups selected from the Substituent Group A.

The ar-$C_{1-6}$ alkyl group, $C_{2-6}$ alkanoyl group, aroyl group, $C_{1-6}$ alkoxycarbonyl group, aryloxycarbonyl group, $C_{1-6}$ alkylsulfonyl group, or arylsulfonyl group for $R^{1a}$ may be substituted with one or more groups selected from the Substituent Group A.

The $C_{1-6}$ alkyl group or $C_{2-6}$ alkenyl group for $R^2$ may be substituted with one or more groups selected from the Substituent Group A.

The $C_{1-6}$ alkyl group, $C_{2-6}$ alkenyl group, aryl group, or ar-$C_{1-6}$ alkyl group for $R^{2a}$ may be substituted with one or more groups selected from the Substituent Group A.

The $C_{1-6}$ alkoxycarbonyl group, aryloxycarbonyl group, or acyl group for $R^6$ may be substituted with one or more groups selected from the Substituent Group A.

The $C_{1-6}$ alkoxycarbonyl group, aryloxycarbonyl group, or acyl group for $R^7$ may be substituted with one or more groups selected from the Substituent Group A.

The methylene group formed by $R^6$ and $R^7$ together may be substituted with one or more groups selected from the group consisting of the Substituent Group A.

Examples of the salt of the compound represented by Formula (1-1) may include salts for conventionally known basic groups such as an amino group, and acidic groups such as a hydroxyl group and a carboxyl group.

Examples of the salt for a basic group include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of the salt for an acidic group include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

The manufacturing method of the invention uses a compound represented by Formula (1) described below, or a compound represented by Formula (2) described below, as a starting raw material. According to the invention, desired 3,4,5-tricaffeoylquinic acid can be produced conveniently by allowing at least one hydroxyl group in the groups represented by $OR^3$, $OR^4$ and $OR^5$ contained in these compounds, to react with an $X^1$ group in a compound represented by Formula (4) described below to form an ester bond, and then eliminating (detaching) protective groups contained in the product (for example, a hydroxyl protective group, a carboxyl protective group, and a phenolic hydroxyl protective group).

In the following description, first, an embodiment of using a compound represented by Formula (1) as a starting raw material is described in detail, and thereafter, an embodiment of using a compound represented by Formula (2) as a starting raw material is described in detail.

First Exemplary Embodiment

A first exemplary embodiment of the manufacturing method of the invention includes at least Step (A1) of allowing a compound represented by Formula (1) to react with a compound represented by Formula (4); and Step (A2) of performing a deprotection reaction of eliminating protective groups from the product obtained in Step (A1), and producing 3,4,5-tricaffeoylquinic acid.

Hereinafter, the compounds used in each step, and the procedure of the steps are described in detail.

[Step (A1)]

Step (A1) is a step of allowing a compound represented by Formula (1) to react with a compound represented by Formula (4), and thus obtaining a compound represented by Formula (5-1), as illustrated in the following scheme.

First, the compounds used in the present step are described in detail.

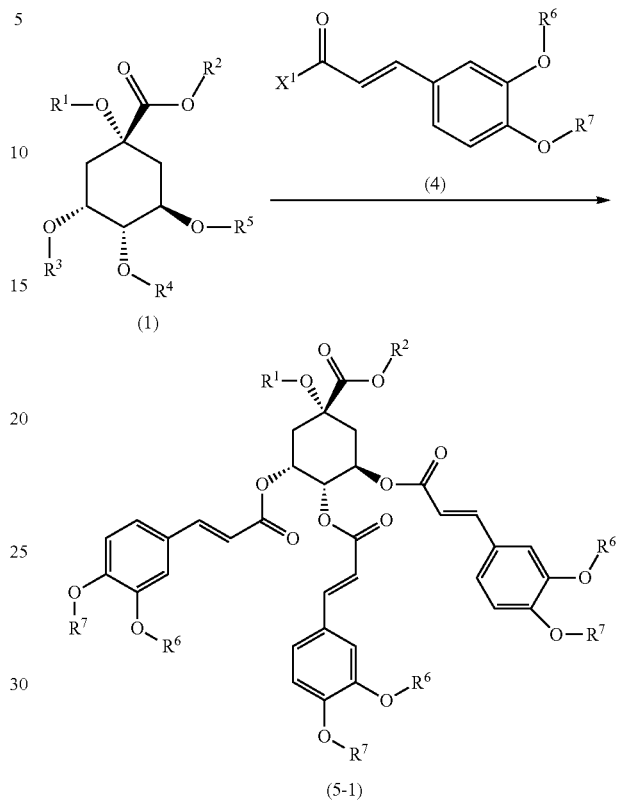

$R^1$ and $R^2$ are such that $R^1$ represents a hydrogen atom or a hydroxyl protective group, while $R^2$ represents a hydrogen atom or a carboxyl protective group, and at least one of $R^1$ and $R^2$ is not a hydrogen atom, or $R^1$ and $R^2$ are joined together to form a protective group represented by —B($R^a$)—. In other words, the definitions (meanings) of $R^1$ and $R^2$ correspond to the following (A) or (B):

(A) $R^1$ represents a hydrogen atom or a hydroxyl protective group, while $R^2$ represents a hydrogen atom or a carboxyl protective group, and at least one of $R^1$ and $R^2$ is not a hydrogen atom.

(B) $R^1$ and $R^2$ are joined together to form a protective group represented by —B($R^a$)—.

Specific embodiments of the above item (A) include embodiment X in which $R^1$ represents a hydroxyl protective group, while $R^2$ represents a carboxyl protective group; embodiment Y in which $R^1$ represents a hydrogen atom, while $R^2$ represents a carboxyl protective group; and embodiment Z in which $R^1$ represents a hydroxyl protective group, while $R^2$ represents a hydrogen atom. Among them, embodiment X is preferred from the viewpoint that 3,4,5-tricaffeoylquinic acid can be produced more efficiently.

Meanwhile, as will be described below, at least one of $R^3$, $R^4$, and $R^5$ represents a hydrogen atom; however, even in a case in which $R^1$ is a hydrogen atom, the compound represented by Formula (4) preferentially reacts with an OH group in which at least one of $R^3$, $R^4$, and $R^5$ is a hydrogen atom, rather than an OH group in which $R^1$ is a hydrogen atom. The details of the reason described above are not clearly understood; however, it is speculated that due to the steric hindrance of $R^2COO$— that is adjacent to $R^1O$—, the reaction between the compound represented by Formula (4) and R¹O— does not easily proceed.

The definition for the hydroxyl protective group represented by R¹ is as described above. Among them, from the viewpoint of being capable of efficiently performing deprotection without damaging the ester bonds at the 3-position to the 5-position of the quinic acid part formed by the above-described reaction, and producing 3,4,5-tricaffeoylquinic acid more efficiently (hereinafter, also simply referred to as "viewpoint that the effects of the invention become superior"), R¹ is preferably a $C_{1-6}$ alkoxycarbonyl group which may be substituted, an aryloxycarbonyl group which may be substituted, or an acyl group which may be substituted; more preferably a $C_{1-6}$ alkoxycarbonyl group which may be substituted with one or more groups selected from the Substituent Group A, an aryloxycarbonyl group which may be substituted with one or more groups selected from the Substituent Group A, or an acyl group which may be substituted with one or more groups selected from the Substituent Group A; even more preferably a $C_{1-6}$ alkoxycarbonyl group which may be substituted with a halogen atom; and most preferably a methoxycarbonyl group or a trichloroethoxycarbonyl group. When a $C_{1-6}$ alkoxycarbonyl group which may be substituted with a halogen atom is used as R¹, a compound represented by Formula (5-1) can be deprotected more efficiently under the conditions that the caffeoyl group is not cleaved.

The definition for the carboxyl protective group represented by R² is as described above. Above all, from the viewpoint that the effects of the invention become superior, R² is preferably a $C_{1-6}$ alkyl group which may be substituted, or a $C_{2-6}$ alkenyl group which may be substituted; more preferably a $C_{1-6}$ alkyl group which may be substituted with one or more groups selected from the Substituent Group A, or a $C_{2-6}$ alkenyl group which may be substituted with one or more groups selected from the Substituent Group A; even more preferably a $C_{1-6}$ alkyl group which may be substituted with a halogen atom; and most preferably a methyl group or a trichloroethyl group.

When a $C_{1-6}$ alkyl group which may be substituted with a halogen atom is used as R², a compound represented by Formula (5-1) can be deprotected more efficiently under the conditions that the caffeoyl group is not broken.

Meanwhile, when R¹ is a $C_{1-6}$ alkoxycarbonyl group, R² is preferably a $C_{1-6}$ alkyl group. When R¹ is a $C_{1-6}$ alkoxycarbonyl group substituted with a halogen atom, R² is preferably a $C_{1-6}$ alkyl group substituted with a halogen atom.

$R^a$ represents a $C_{1-6}$ alkyl group which may be substituted, an aryl group which may be substituted, or a $C_{1-6}$ alkoxy group which may be substituted. Among them, from the viewpoint that the effects of the invention become superior, $R^a$ is preferably an aryl group which may be substituted or a $C_{1-6}$ alkoxy group which may be substituted; more preferably an aryl group which may be substituted; and even more preferably a phenyl group.

More specifically, when R¹ and R² are joined together to form —B($R^a$)—, the compound represented by Formula (1) is represented by the following structural formula:

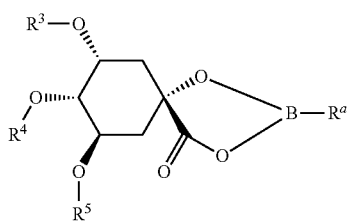

R³, R⁴, and R⁵, which are identical or different, each represent a hydrogen atom or a group represented by Formula (3).

At least one of R³, R⁴, and R⁵ represents a hydrogen atom. Above all, from the viewpoint that 3,4,5-tricaffeoylquinic acid can be produced efficiently in fewer steps, it is preferable that at least two of R³, R⁴, and R⁵ are hydrogen atoms, and it is more preferable that all of them are hydrogen atoms.

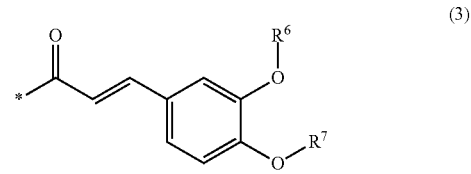

(3)

In Formula (3), R⁶ and R⁷, which are identical or different, each represent a phenolic hydroxyl protective group, or R⁶ and R⁷ are joined together to form a protective group selected from the group consisting of a carbonyl group (—CO—) and a methylene group which may be substituted. Symbol * represents the bonding position to an oxygen atom of the compound represented by Formula (1).

From the viewpoint that the effects of the invention become superior, R⁶ is preferably a $C_{1-6}$ alkoxycarbonyl group which may be substituted, an aryloxycarbonyl group which may be substituted, a $C_{2-6}$ alkenyl group which may be substituted, or an acyl group which may be substituted; more preferably a $C_{1-6}$ alkoxycarbonyl group which may be substituted with one or more groups selected from the Substituent Group A, an aryloxycarbonyl group which may be substituted with one or more groups selected from the Substituent Group A, a $C_{2-6}$ alkenyl group which may be substituted with one or more groups selected from the Substituent Group A, or an acyl group which may be substituted with one or more groups selected from the Substituent Group A; even more preferably a $C_{1-6}$ alkoxycarbonyl group which may be substituted with a halogen atom; and most preferably a methoxycarbonyl group or a trichloroethoxycarbonyl group.

Meanwhile, when a $C_{1-6}$ alkoxycarbonyl group which may be substituted with a halogen atom is used as R⁶, a compound represented by Formula (5-1) can be deprotected more efficiently under the conditions that the caffeoyl group is not broken.

From the viewpoint that the effects of the invention become superior, R⁷ is preferably a $C_{1-6}$ alkoxycarbonyl group which may be substituted, an aryloxycarbonyl group which may be substituted, a $C_{2-6}$ alkenyl group which may be substituted, or an acyl group which may be substituted; more preferably a $C_{1-6}$ alkoxycarbonyl group which may be substituted with one or more groups selected from the Substituent Group A, an aryloxycarbonyl group which may be substituted with one or more groups selected from the Substituent Group A, a $C_{2-6}$ alkenyl group which may be substituted with one or more groups selected from the Substituent Group A, or an acyl group which may be substituted with one or more groups selected from the Substituent Group A; even more preferably a $C_{1-6}$ alkoxycarbonyl group which may be substituted with a halogen atom; and most preferably a methoxycarbonyl group or a trichloroethoxycarbonyl group.

When a $C_{1-6}$ alkoxycarbonyl group which may be substituted with a halogen atom is used as $R^7$, a compound represented by Formula (5-1) can be deprotected more efficiently under the conditions that the caffeoyl group is not broken.

Furthermore, it is preferable that $R^6$ and $R^7$ are identical.

In Formula (4), $X^1$ represents a hydroxyl group or a leaving group. There are no particular limitations on the kind of the leaving group; however, from the viewpoint that the reaction proceeds more efficiently, $X^1$ is preferably a halogen atom, and more preferably a chlorine atom.

The definitions of $R^6$ and $R^7$ are as described above.

The procedure of the present step is not particularly limited as long as a product represented by the above Formula (5-1) is obtained; however, the procedure can be roughly divided into two methods based on the kind of $X^1$ in Formula (4). In the following, the respective methods (method M1 and method M2) are described in detail.

(Method M1: Method of Using Compound Represented by Formula (4) in which $X^1$ is Hydroxyl Group)

When $X^1$ in Formula (4) is a hydroxyl group, a compound represented by Formula (5-1) can be produced by allowing a compound represented by Formula (1) to react with a compound represented by Formula (4) using a condensing agent.

Regarding the condensing agent used in this reaction, any known condensing agent can be used, and examples thereof include (O)-(7-azabenzotriazol-1-yl)-N,N,N',N'-tetramethyluronium hexafluorophosphate, 1-(3-dimethylaminopropyl)-3-ethylcarbodiimide hydrochloride, dicyclohexylcarbodiimide, carbonyldiimidazole, 2-chloro-1-methylpyridinium iodide, 4-(4,6-dimethoxy-1,3,5-triazin-2-yl)-4-methylmorpholine chloride, and ((benzotriazol-1-yl)oxy)(trispyrrolidino)phosphonium hexafluorophosphate.

Regarding the amount of use of the condensing agent, an optimal amount is appropriately selected based on the structure of the compound represented by Formula (1) that is to be used. For example, when $R^3$, $R^4$, and $R^5$ are all hydrogen atoms, the amount of use of the condensing agent is preferably 3 to 30 times, and more preferably 3.3 to 9.0 times, the molar amount of the compound represented by Formula (1). Furthermore, when two of $R^3$, $R^4$, and $R^5$ are hydrogen atoms, the amount of use of the condensing agent is preferably 2 to 20 times, and more preferably 2.2 to 6.0 times, the molar amount of the compound represented by Formula (1). Moreover, when one of $R^3$, $R^4$, and $R^5$ is a hydrogen atom, the amount of use of the condensing agent is preferably 1 to 10 times, and more preferably 1.1 to 3.0 times, the molar amount of the compound represented by Formula (1).

The method M1 may be carried out in the presence of a base, if necessary. When a base is present, the reaction proceeds more efficiently, and the yield is increased.

There are no particular limitations on the kind of the base used; however, examples thereof include pyridines such as pyridine, picoline, lutidine, collidine, and 4-dimethylaminopyridine; diamines such as tetramethylethylenediamine; trialkylamines such as triethylamine and diisopropylethylamine; and polycycloamines such as 1,8-diazabicyclo[5.4.0]-7-undecene (DBU), 1,5-diazabicyclo[4.3.0]-5-nonene (DBN), and 1,4-diazabicyclo[2.2.2]octane (DABCO). Pyridines and diamines are preferred, and picoline, lutidine, and tetramethylethylenediamine are more preferred.

Regarding the amount of use of the base, an optimal amount is appropriately selected based on the structure of the compound represented by Formula (1) that is to be used. For example, when $R^3$, $R^4$, and $R^5$ are all hydrogen atoms, the amount of use of the base is preferably 3 to 30 times, and more preferably 3.3 to 9.0 times, the molar amount of the compound represented by Formula (1). Furthermore, when two of $R^3$, $R^4$, and $R^5$ are hydrogen atoms, the amount of use of the base is preferably 2 to 20 times, and more preferably 2.2 to 6.0 times, the molar amount of the compound represented by Formula (1). Moreover, when one of $R^3$, $R^4$, and $R^5$ is a hydrogen atom, the amount of use of the base is preferably 1 to 10 times, and more preferably 1.1 to 3.0 times, the molar amount of the compound represented by Formula (1).

In the method M1, a solvent may be used, if necessary.

The solvent used therein is not particularly limited as long as the solvent does not affect the reaction; however, examples thereof include aliphatic hydrocarbons, aromatic hydrocarbons, halogenated hydrocarbons, ethers, ketones, nitriles, and esters. These solvents may be used as mixtures. Furthermore, any solvent other than those described above may also be incorporated as long as the solvent does not affect the reaction.

Preferred examples of the solvent include halogenated hydrocarbons and nitriles, and methylene chloride, acetonitrile, and propanenitrile are more preferred.

The amount of use of the solvent is not particularly limited; however, the amount of use is preferably 1 to 50 times (v/w), and more preferably 1 to 15 times (v/w), the amount of the compound represented by Formula (1).

Among the solvents described above, it is preferable to use a solvent having a SP value of 8.0 to 10.0, from the viewpoint that the reaction proceeds more efficiently, and the yield is increased. The SP value is a solubility parameter, and is a characteristic value that serves as an indicator of miscibility between liquids. For the SP value, a calculated value calculated by the Fedors method can be used.

An example may be a solvent having a SP value of 8.0 to 10.0 and selected from aromatic hydrocarbons, halogenated hydrocarbons, ethers, ketones, and esters, and more specific examples include butyl acetate (SP value: 8.5), xylene (SP value: 8.8), toluene (SP value: 8.8), ethyl acetate (SP value: 9.0), benzene (SP value: 9.2), dibutyl phthalate (SP value: 9.4), and methylene chloride (SP value: 9.7).

In the method M1, regarding the amount of use of the compound represented by Formula (4), an optimal amount is appropriately selected based on the structure of the compound represented by Formula (1) that is to be used. For example, when $R^3$, $R^4$, and $R^5$ are all hydrogen atoms, the amount of use of the compound represented by Formula (4) is preferably 3.0 to 7.5 times, and more preferably 3.3 to 4.5 times, the molar amount of the compound represented by Formula (1). Furthermore, when two of $R^3$, $R^4$, and $R^5$ are hydrogen atoms, the amount of use of the compound represented by Formula (4) is preferably 2.0 to 5.0 times, and more preferably 2.2 to 3.0 times, the molar amount of the compound represented by Formula (1). Moreover, when one of $R^3$, $R^4$, and $R^5$ is a hydrogen atom, the amount of use of the compound represented by Formula (4) is preferably 1.0 to 2.5 times, and more preferably 1.1 to 1.5 times, the molar amount of the compound represented by Formula (1).

There are no particular limitations on the reaction conditions for the method M1, and optimal conditions are selected based on the compounds used.

Among them, from the viewpoint that the reaction proceeds more efficiently, the reaction temperature is preferably −10° C. to 50° C., and more preferably 0° C. to 40° C. Also, from the viewpoints of the product yield and productivity, the reaction time is preferably 20 minutes to 8 hours, and more preferably 30 minutes to 4 hours.

According to a method different from the method described above, a compound represented by Formula (5-1) can also be produced by allowing a compound represented by Formula (4) to react with an acid halide or an acid anhydride to convert the compound to a mixed acid anhydride, and then allowing a compound represented by Formula (1) to react with the compound represented by Formula (4) in the presence of a base.

Examples of the acid halide or acid anhydride used in this reaction include chloroformic acid esters such as methyl chloroformate, ethyl chloroformate, and trichloroethyl chloroformate; and acid anhydrides such as trifluoroacetic anhydride.

A compound represented by Formula (5-1) can also be produced by allowing a compound represented by Formula (4) to react with a sulfonic acid halide so as to convert the compound to an alkylsulfonyloxy form or an arylsulfonyloxy form as a mixed acid anhydride similar to those described above, thereby converting the resultant to a mixed acid anhydride with sulfonic acid, and then allowing a compound represented by Formula (1) to react with the compound represented by Formula (4) in the presence of a base. Examples of the sulfonic acid halide used for the mixed acid anhydride with sulfonic acid include methanesulfonyl chloride, benzenesulfonyl chloride, and p-nitrobenzenesulfonyl chloride.

Preferred reaction conditions in the case in which these mixed acid anhydrides are allowed to react with a compound represented by Formula (1), are similar to the conditions applied to the method M1.

(Method M2: Method of Using Compound Represented by Formula (4) in which $X^1$ Represents Halogen Atom)

When $X^1$ in Formula (4) represents a halogen atom, a compound represented by Formula (5-1) can be produced by allowing a compound represented by Formula (1) to react with a compound represented by Formula (4) in the presence of a base. This reaction corresponds to a so-called reaction between a carboxylic acid halide and an alcohol.

A compound represented by Formula (4) in which $X^1$ represents a halogen atom can be produced by allowing a compound represented by Formula (4) in which $X^1$ represents a hydroxyl group, to react with a halogenating agent. Regarding the halogenating agent used therein, any known compound can be used, and examples thereof include thionyl chloride, oxalyl chloride, phosphoryl chloride, sulfuryl chloride, phosphorus trichloride, and phosphorus pentachloride.

There are no particular limitations on the kind of the base used in the method M2, and the bases mentioned for the method M1 may be used. Regarding the amount of use of the base, an optimal amount is appropriately selected based on the structure of the compound represented by Formula (1) that is to be used, and the amount of use mentioned with regard to the method M1, and the like may be used.

In the method M2, a solvent may be used, if necessary. There are no particular limitations on the kind of the solvent used, and the solvents mentioned with regard to the method M1 may be used. The amount of use of the solvent is also as described above.

Furthermore, in the method M2, regarding the amount of use of the compound represented by Formula (4), an optimal amount is appropriately selected based on the structure of the compound represented by Formula (1) that is to be used, and the amount of use mentioned with regard to the method M1, and the like may be used.

There are no particular limitations on the reaction conditions for the method M2, and optimal conditions are selected based on the compounds used.

Among them, from the viewpoint that the reaction proceeds more efficiently, the reaction temperature is preferably −20° C. to 40° C., and more preferably −10° C. to 30° C. From the viewpoints of the product yield and productivity, the reaction time is preferably 20 minutes to 8 hours, and more preferably 30 minutes to 4 hours.

After the present step (A1), separation and purification between the product and impurities (unreacted raw materials, side products, and the like) may be carried out as necessary, before Step (A2) that will be described below.

Separation and purification may be carried out by routine methods, and examples thereof include an extraction operation using organic solvents, recrystallization, crystallization using poor solvents, and column chromatography using silica gel.

In the present specification, hereinafter, the above-described treatments are simply referred to as "separation and purification treatments".

[Step (A2)]

Step (A2) is a step of producing 3,4,5-tricaffeoylquinic acid by deprotecting the product obtained in Step (A1) (compound represented by Formula (5-1)), as illustrated in the following scheme. More specifically, Step (A2) is a step of obtaining desired 3,4,5-tricaffeoylquinic acid by deprotection of the protective groups (a hydroxyl protective group, a carboxyl protective group, a phenolic hydroxyl protective group, —B($R^a$)—, and the like) contained in the compound represented by Formula (5-1).

In the present step, deprotection is intended to mean detachment of groups that protect a hydroxyl group, a phenolic hydroxyl group, and a carboxyl group in 3,4,5-tricaffeoylquinic acid as described above.

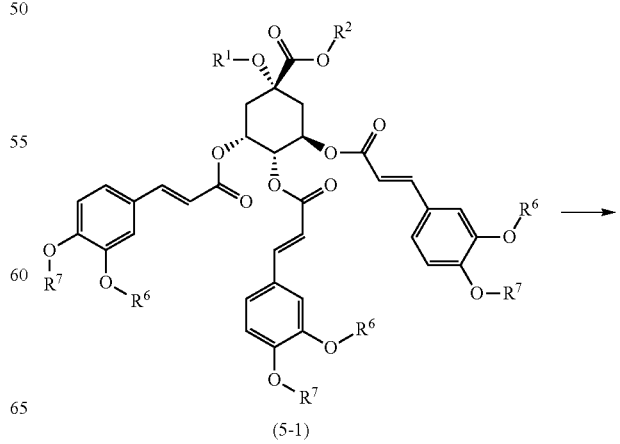

(5-1)

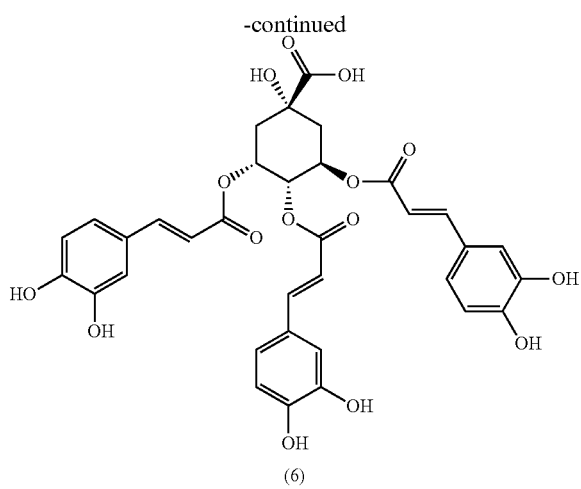

(6)

A compound represented by Formula (6) can be produced by deprotecting the compound represented by Formula (5-1).

This reaction may be carried out according to the methods described in, for example, Protective Groups in Organic Synthesis, 4$^{th}$ Ed., pp. 367-430, 2007, John Wiley & Sons, Inc.

Preferred examples of the method for deprotection include a method of using a nucleophilic agent (method M3), and a method of using zinc dust (method M4). In the following, the respective methods are described in detail.

(Method M3: Method of Using Nucleophilic Agent)

A compound represented by Formula (6) can be produced by allowing a compound represented by Formula (5-1) to react with a nucleophilic agent.

There are no particular limitations on the kind of the nucleophilic agent used in this reaction; however, examples thereof include lithium chloride, lithium bromide, lithium iodide, trimethylsilyl iodide, trimethylsilyl chloride/sodium iodide, sodium iodide, sodium dodecyl thiolate, sodium hexadecyl thiolate, and disodium thioglycolate. Lithium chloride, lithium chloride/sodium bromide, lithium chloride/potassium bromide, lithium chloride/sodium iodide, lithium chloride/potassium iodide, lithium bromide, and lithium iodide are preferred, and lithium chloride/sodium bromide, lithium chloride/sodium iodide, lithium bromide, and lithium iodide are more preferred.

The amount of use of the nucleophilic agent is preferably 12 to 60 times, and more preferably 12 to 30 times, the molar amount of the compound represented by Formula (5-1).

In this reaction, a solvent may be used as necessary.

The solvent used herein is not particularly limited as long as the solvent does not affect the reaction; however, examples thereof include nitriles, amides, and pyridines. These solvents may be used as mixtures. Preferred examples of the solvent include acetonitrile, propanenitrile, N,N-dimethylformamide, N,N-dimethylacetamide, N-methylpyrrolidone, dimethylimidazolidinone, picoline, lutidine, and collidine.

The amount of use of the solvent is not particularly limited; however, the amount of use is preferably 2 to 50 times (v/w), and more preferably 3 to 20 times (v/w), the amount of the compound represented by Formula (5-1).

In this reaction, an acid may be added as necessary. When an acid is added, side reactions are reduced, and the yield can be increased.

The amount of use of the acid is preferably 1 to 10 times, and more preferably 3 to 6 times, the molar amount of the compound represented by Formula (5-1), in view of having no adverse influence on the deprotection reaction.

There are no particular limitations on the kind of the acid as long as the acid does not affect the reaction; however, examples thereof include hydrogen chloride, hydrogen bromide, and hydrogen iodide. In the case of using a basic solvent such as pyridine, the acid can also be added in the form of a salt thereof.

The reaction conditions for the method M3 are not particularly limited, and optimal conditions are selected based on the compounds used. Among them, from the viewpoint that the reaction proceeds more efficiently, the reaction temperature is preferably 20° C. to 180° C., and more preferably 60° C. to 150° C. From the viewpoints of the product yield and productivity, the reaction time is preferably 10 minutes to 12 hours, and more preferably 30 minutes to 5 hours.

(Method M4: Method of Using Zinc Dust)

A compound represented by Formula (6) can be produced by allowing a compound represented by Formula (5-1) to react with zinc dust.

In this reaction, a solvent may be used as necessary.

There are no particular limitations on the solvent used as long as the solvent does not affect the reaction; however, examples thereof include the solvents mentioned above with regard to the method M1, and formic acid, acetic acid, and propionic acid are preferred.

There are no particular limitations on the amount of use of the solvent; however, the amount of use is preferably 3 to 50 times (v/w), and more preferably 4 to 30 times (v/w), the amount of the compound represented by Formula (5-1).

There are no particular limitations on the amount of use of the zinc dust used in this reaction; however, the amount of use is preferably 10 to 60 times, and more preferably 12 to 30 times, the molar amount of the compound represented by Formula (5-1).

There are no particular limitations on the reaction conditions for the method M3, and optimal conditions are selected based on the compounds used. Among them, from the viewpoint that the reaction proceeds more efficiently, the reaction temperature is preferably 10° C. to 100° C., and more preferably 20° C. to 50° C. From the viewpoints of the product yield and productivity, the reaction time is preferably 10 minutes to 12 hours, and more preferably 30 minutes to 3 hours.

Meanwhile, when an alkenyl group is included among $R^1$, $R^6$, and $R^7$, a method of performing deprotection using a palladium catalyst may also be employed.

There are no particular limitations on the palladium catalyst; however, examples thereof include palladium acetate, tetrakis(triphenylphosphine)palladium, dichlorodi(triphenylphosphine)palladium, and Pd—C. Palladium acetate and tetrakis(triphenylphosphine)palladium are preferred, and tetrakis(triphenylphosphine)palladium is more preferred.

The amount of use of the palladium catalyst is preferably 0.001 to 2 times, and more preferably 0.02 to 0.5 times, the molar amount of the compound represented by Formula (5-1).

Furthermore, for the present method, it is preferable to incorporate a nucleophilic species that reacts with allyl palladium. Examples of the nucleophilic species include water, alcohols, and secondary amines. Preferred examples of the nucleophilic species include water, methanol, morpholine, diethylamine, and piperidine, while morpholine is more preferred.

The amount of use of the nucleophilic species is not particularly limited; however, the amount of use is preferably 2 to 100 times, and more preferably 10 to 60 times, the molar amount of the compound represented by Formula (5-1).

There are no particular limitations on the reaction conditions for the present method, and optimal conditions are selected based on the compounds used. Among them, from the viewpoint that the reaction proceeds more efficiently, the reaction temperature is preferably 20° C. to 180° C., and more preferably 10° C. to 50° C. From the viewpoints of the product yield and productivity, the reaction time is preferably 10 minutes to 12 hours, and more preferably 30 minutes to 5 hours.

Meanwhile, in Formula (5-1), when $R^1$ and $R^2$ are joined together to form —B($R^a$)—, a treatment of bringing the compound represented by Formula (5-1) into contact with an acidic aqueous solution, and detaching —B($R^a$)—, may be carried out as necessary, before the method M3 or the method M4 is carried out.

Examples of the acid that is included in the acidic aqueous solution used include phosphoric acid, hydrochloric acid, and sulfuric acid.

The temperature of the acidic aqueous solution is not particularly limited; however, from the viewpoint that the reaction proceeds more efficiently, the temperature is preferably 0° C. to 40° C., and more preferably 0° C. to 30° C.

There are no particular limitations on the time for the reaction between the compound represented by Formula (5-1) and the acidic aqueous solution; however, from the viewpoints of the product yield and productivity, the reaction time is preferably 1 minute to 30 minutes, and more preferably 3 minutes to 10 minutes.

Meanwhile, the treatment for detaching —B($R^a$)— may be carried out after the method M3 or the method M4 is carried out.

Furthermore, the procedure of deprotection may be carried out stepwise. More specifically, in a first stage, the moieties represented by $R^6$ and $R^7$ may be deprotected, and in a second stage, the moieties represented by $R^1$ and $R^2$ may be deprotected. Regarding the method for deprotection, any known methods including the methods described above can be employed. Regarding the method for deprotection in the first stage, for example, a method of using a strong base such as lithium hydroxide, or hydrazine can be employed.

After this Step (A2), a separation and purification treatment for the product and impurities (unreacted raw materials, side products, and the like) may be can ied out, if necessary.

By carrying out Step (A1) and Step (A2), desired 3,4,5-tricaffeoylquinic acid can be produced efficiently.

3,4,5-Tricaffeoylquinic acid can be used in various applications, and for example, since 3,4,5-tricaffeoylquinic acid has a variety of physiological activities such as antitumor action, antidiabetic action, antihypertensive action, antiviral action, a skin brightening effect, and a disinfecting effect, the applications include various medicines and quasi-medicines, foods for specified health care, dietary supplements, and cosmetic products.

A suitable embodiment of the compound represented by Formula (1) described above is a compound represented by Formula (1-1) or a salt thereof.

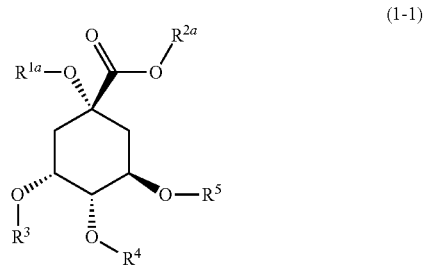

(1-1)

In Formula (1-1), $R^{1a}$ represents an ar-$C_{1-6}$ alkyl group which may be substituted, a formyl group, a $C_{2-6}$ alkanoyl group which may be substituted, an aroyl group which may be substituted, a $C_{1-6}$ alkoxycarbonyl group which may be substituted, an aryloxycarbonyl group which may be substituted, a $C_{1-6}$ alkylsulfonyl group which may be substituted, or an arylsulfonyl group which may be substituted.

$R^{2a}$ represents a $C_{1-6}$ alkyl group which may be substituted, a $C_{2-6}$ alkenyl group which may be substituted, an aryl group which may be substituted, or an ar-$C_{1-6}$ alkyl group which may be substituted.

The definitions of $R^3$, $R^4$, and $R^5$ are as described above.

$R^{1a}$ is preferably a $C_{1-6}$ alkoxycarbonyl group which may be substituted, an aryloxycarbonyl group which may be substituted, or an acyl group which may be substituted, and more preferably a $C_{1-6}$ alkoxycarbonyl group which may be substituted with a halogen atom.

$R^{2a}$ is preferably a $C_{1-6}$ alkyl group which may be substituted, or a $C_{2-6}$ alkenyl group which may be substituted, and more preferably a $C_{1-6}$ alkyl group which may be substituted with a halogen atom.

The method for manufacturing the compound represented by Formula (1) described above is not particularly limited, and appropriate combinations of known methods can be carried out. Among them, from the viewpoint of having excellent productivity, it is preferable that the compound represented by Formula (1) is produced by a method of using quinic acid as a starting raw material as described below.

In the following, a suitable embodiment of the method for manufacturing a compound represented by Formula (1) is described in detail.

[Suitable Embodiment of Method for Manufacturing Compound Represented by Formula (1) ($1^{st}$)]

In Formula (1), $R^1$ represents a hydrogen atom or a hydroxyl protective group; $R^2$ represents a hydrogen atom or a carboxyl protective group (provided that at least one of $R^1$ and $R^2$ is not a hydrogen atom); and when all of $R^3$ to $R^5$ are hydrogen atoms, it is preferable that the compound represented by Formula (1) is produced by the following scheme. Through the following method, the compound represented by Formula (1) can be produced efficiently. However, when $R^1$ is a hydrogen atom, (1a) can be produced by allowing the following (A1) to react directly with (A5).

This method is suitable as a method for efficiently producing a compound in which $R^1$ is a hydroxyl protective group and $R^2$ is a carboxyl protective group.

Meanwhile, in the formula, $L^1$ represents a leaving group.

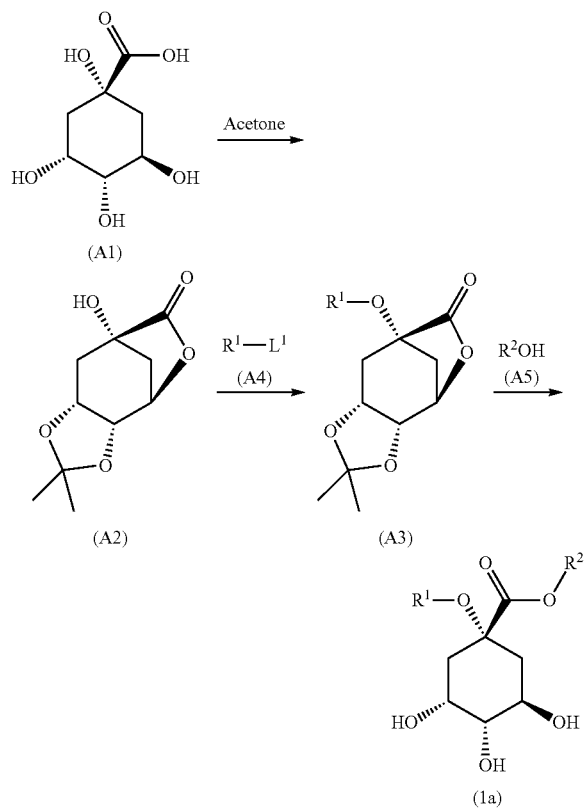

A compound represented by Formula (A2) can be produced by allowing quinic acid represented by Formula (A1) to react with acetone in the presence of an acid.

This reaction may be carried out according to the method described in Rohloff J. C., et al., J. Org. Chem., Vol. 63, pp. 4545-4550, 1998.

There are no particular limitations on the manufacturing conditions for the present reaction; however, from the viewpoint that the reaction proceeds efficiently, the reaction temperature is preferably 20° C. to 60° C., and more preferably 30° C. to 60° C., and the reaction time is preferably 1 to 6 hours, and more preferably 2 to 5 hours.

After completion of the reaction, an alkali may be added to the reaction mixture and neutralize the reaction mixture as necessary, and then the separation and purification treatment described above may be carried out.

A compound represented by Formula (A3) can be produced by allowing a compound represented by Formula (A2) to react with a compound represented by Formula (A4).

The procedure of the present reaction can be carried out according to the procedure described with regard to the Step (A1) described above. For example, there is available a method of allowing a compound represented by Formula (A2) to react with an alkyl chloroformate represented by formula: $R^1$-$L^1$ in the presence of a base (preferably, tetramethylethylenediamine), and obtaining a compound represented by Formula (A3).

The compound represented by Formula (1a) can be produced by allowing a compound represented by Formula (A3) to react with a compound represented by Formula (A5) in the presence of an acid catalyst.

There are no particular limitations on the kind of the acid used, and examples thereof include sulfuric acid, methanesulfonic acid, and toluenesulfonic acid. From the viewpoint of being inexpensive and causing the reaction to proceed more efficiently, sulfuric acid and methanesulfonic acid are preferred.

The amount of use of the acid is not particularly limited; however, from the viewpoint that the reaction proceeds more efficiently, the amount of use is preferably 0.001 to 0.1 times, and more preferably 0.005 to 0.05 times, the molar amount of the compound represented by Formula (A3).

The definition of $R^2$ in the compound represented by Formula (A5) is as described above. Among them, from the viewpoint that the present reaction proceeds efficiently, and the subsequent deprotection is facilitated, $R^2$OH is preferably methanol.

The amount of use of the compound represented by Formula (A5) is not particularly limited; however, from the viewpoint that the reaction proceeds more efficiently, the amount of use is preferably 10 to 200 times, and more preferably 20 to 100 times, the molar amount of the compound represented by Formula (A3).

In the present reaction, a solvent may be used, if necessary; however, usually, the compound represented by Formula (A5) is also used as a solvent.

There are no particular limitations on the manufacturing conditions for the present reaction; however, from the viewpoint of causing the reaction to proceed efficiently and suppressing side reactions, the reaction temperature is preferably 0° C. to 50° C., and more preferably 0° C. to 30° C., and the reaction time is preferably 1 to 8 hours, and more preferably 1 to 5 hours.

Furthermore, regarding another method for obtaining a compound represented by Formula (1a), for example, a method of allowing a compound represented by Formula (A3) to react with a compound represented by Formula (A5) in the presence of a base, subsequently bringing the product thus obtained into contact with an acid, and thereby obtaining a compound represented by Formula (1a), may be employed. In the present method, the compound represented by Formula (1a) is synthesized by a two-stage treatment, and thus the yield is higher.

Meanwhile, suitable examples of the base include inorganic bases, metal alkoxides, and organic bases. Sodium carbonate, potassium carbonate, sodium hydrogen carbonate, sodium ethoxide, and sodium methoxide are preferred, and sodium hydrogen carbonate and sodium methoxide are more preferred.

Furthermore, examples of the acid include sulfuric acid; sulfonic acids such as methanesulfonic acid and trifluoromethanesulfonic acid; carboxylic acids such as acetic acid and trifluoroacetic acid; and hydrogen chloride (HCl). Sulfuric acid, methanesulfonic acid, and hydrogen chloride are preferred, and sulfuric acid and hydrogen chloride are more preferred.

[Suitable Embodiment of Method for Manufacturing Compound Represented by Formula (1) ($2^{nd}$)]

In Formula (1), $R^1$ represents a hydrogen atom or a hydroxyl protective group; $R^2$ represents a hydrogen atom or a carboxyl protective group (provided that at least one of $R^1$ and $R^2$ is not a hydrogen atom); and when two of $R^3$ to $R^5$ are hydrogen atoms, and the remaining group is a group represented by Formula (3), it is preferable that the compound represented by Formula (1) is produced by the following scheme. Through the following method, the compound represented by Formula (1) can be produced efficiently.

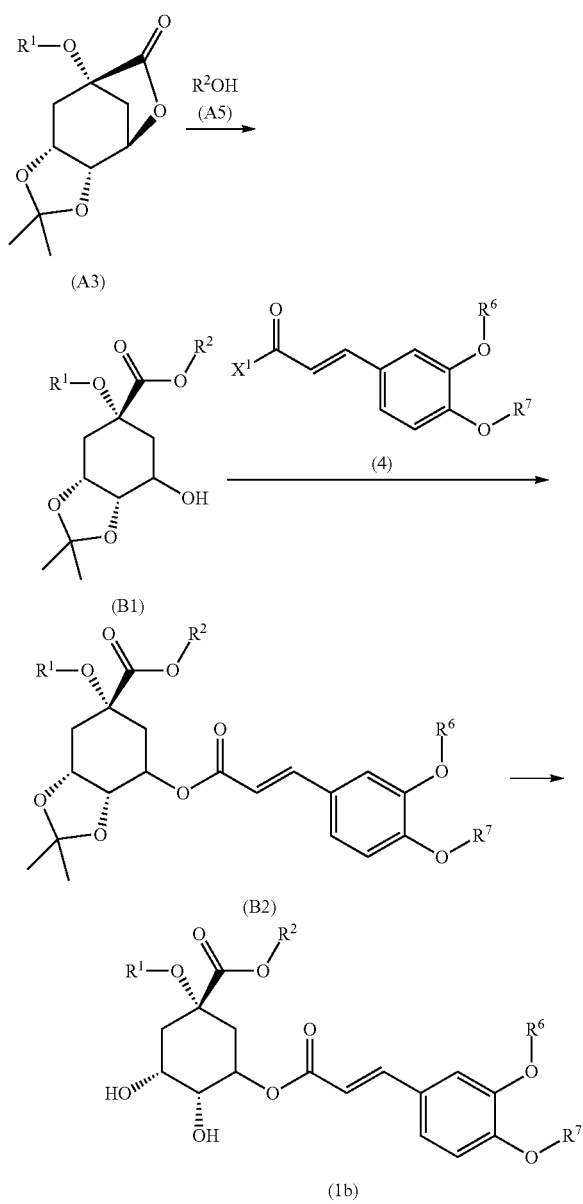

A compound represented by Formula (B1) can be produced by allowing a compound represented by Formula (A3) to react with a compound represented by Formula (A5).

This reaction may be carried out according to the method described in J. Org. Chem., Vol. 71, p. 5397, 2006.

In the present reaction, for example, the compound represented by Formula (B1) can be produced by allowing a compound represented by Formula (A3) to react with a compound represented by Formula (A5) under basic conditions.

There are no particular limitations on the kind of the base used to achieve basic conditions, and examples thereof include sodium methoxide, anhydrous potassium carbonate, and anhydrous sodium carbonate.

There are no particular limitations on the reaction conditions for the present reaction; however, from the viewpoint that the reaction proceeds efficiently, the reaction temperature is preferably 10° C. to 80° C., and more preferably 20° C. to 50° C., and the reaction time is preferably 30 minutes to 5 hours, and more preferably 45 minutes to 3 hours.

A compound represented by Formula (B2) can be produced by allowing a compound represented by Formula (B1) to react with a compound represented by Formula (4).

The procedure of the present reaction may be carried out according to the procedure of Step (A1) described above.

A compound represented by Formula (1b) can be produced by deprotecting a compound represented by Formula (B2).

This reaction may be carried out according to the methods described in Protective Groups in Organic Synthesis, 4$^{th}$ Ed., pp. 16-366, 2007, John Wiley & Sons, Inc.

Regarding a preferred method for deprotection, a method of allowing a compound represented by Formula (B2) to react with water under acidic conditions may be employed.

There are no particular limitations on the kind of the acid used to achieve acidic conditions, and examples thereof include acetic acid, phosphoric acid, hydrochloric acid, and trifluoroacetic acid.

There are no particular limitations on the reaction conditions for the present reaction; however, from the viewpoint that the reaction proceeds efficiently, the reaction temperature is preferably 0° C. to 80° C., and more preferably 10° C. to 60° C., and the reaction time is preferably 10 minutes to 8 hours, and more preferably 30 minutes to 5 hours.

[Suitable Embodiment of Method for Manufacturing Compound Represented by Formula (1) (3$^{rd}$)]

In Formula (1), $R^1$ represents a hydrogen atom or a hydroxyl protective group; $R^2$ represents a hydrogen atom or a carboxyl protective group (provided that at least one of $R^1$ and $R^2$ is not a hydrogen atom); and when one of $R^3$ to $R^5$ is a hydrogen atom, and the remaining groups are groups represented by Formula (3), it is preferable that the compound represented by Formula (1) is produced by the following scheme. Through the following method, the compound represented by Formula (1) can be produced efficiently.

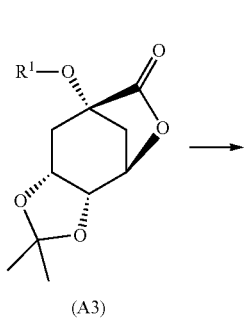

(A3)

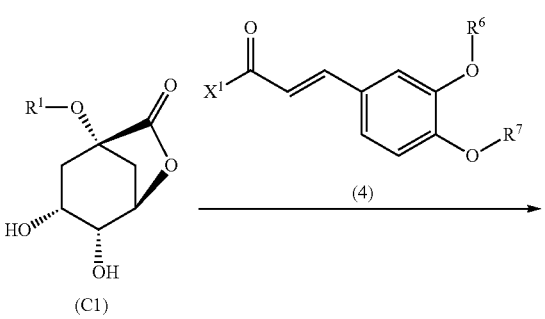

(C1)

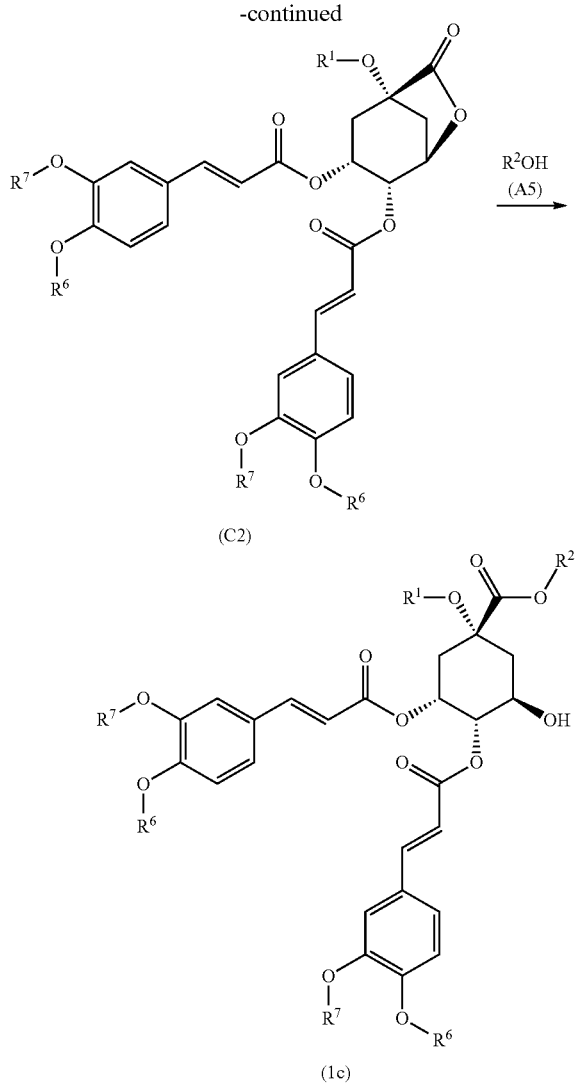

(C2)

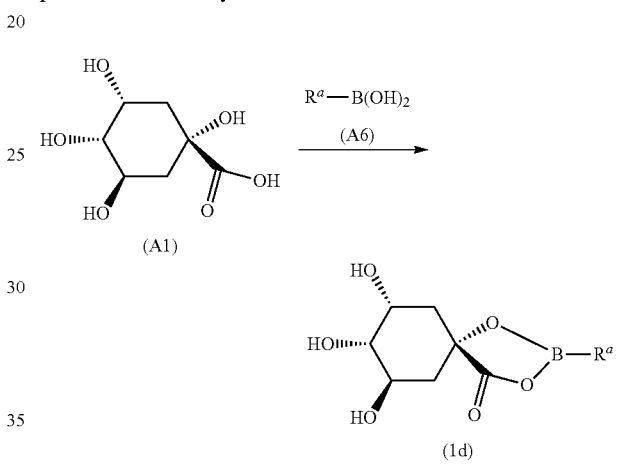

A compound represented by Formula (C1) can be produced by deprotecting the compound represented by Formula (A3).

This reaction may be carried out according to the methods described in Protective Groups in Organic Synthesis, 4$^{th}$ Ed., pp. 16-366, 2007, John Wiley & Sons, Inc.

Regarding a preferred method for deprotection, a method of allowing a compound represented by Formula (A3) to react with an acidic aqueous solution, may be employed.

There are no particular limitations on the kind of the acid used in the acidic aqueous solution, and examples thereof include acetic acid, hydrochloric acid, and trifluoroacetic acid.

There are no particular limitations on the reaction conditions for the present reaction; however, from the viewpoint that the reaction proceeds efficiently, the reaction temperature is preferably 10° C. to 60° C., and more preferably 20° C. to 50° C., and the reaction time is preferably 30 minutes to 8 hours, and more preferably 1 to 5 hours.

A compound represented by Formula (C2) can be produced by allowing the compound represented by Formula (C1) to react with the compound represented by Formula (4).

The procedure of the present reaction may be carried out according to the procedure of Step (A1) described above.

A compound represented by Formula (1c) can be produced by allowing the compound represented by Formula (C2) to react with the compound represented by Formula (A5).

Regarding the procedure of the present invention, the method of allowing the compound represented by Formula (A3) to react with a compound represented by Formula (A5), which was described in the above section [Suitable embodiment of method for manufacturing compound represented by Formula (1) (2$^{nd}$)], may be employed.

[Suitable Embodiment of Method for Manufacturing Compound Represented by Formula (1) (4$^{th}$)]

In Formula (1), when $R^1$ and $R^2$ are joined together to form —B($R^a$)—, and all of $R^3$ to $R^5$ are hydrogen atoms, it is preferable that the compound represented by Formula (1) is produced by the following scheme. Through the following method, the compound represented by Formula (1) can be produced efficiently.

A compound represented by Formula (1d) can be produced by allowing a compound represented by Formula (A1) to react with a compound represented by Formula (A6).

The definition of $R^a$ in the compound represented by Formula (A6) is as described above. Among them, from the viewpoint that the present reaction proceeds more efficiently, $R^a$ is preferably a phenyl group.

The amount of use of the compound represented by Formula (A6) is not particularly limited; however, from the viewpoint that the reaction proceeds more efficiently, the amount of use is preferably 0.95 to 1.05 times, and more preferably 1.0 to 1.03 times, the molar amount of the compound represented by Formula (A1).

If necessary, the present reaction may be carried out in the presence of a dehydrating agent such as anhydrous sodium sulfate or a molecular sieve. When a dehydrating agent is used, the reaction proceeds more efficiently.

In the present reaction, a solvent may be used, if necessary.

The solvent used therein is not particularly limited as long as the solvent does not affect the reaction; however, examples thereof include aliphatic hydrocarbons, halogenated hydrocarbons, ethers, ketones, and esters. These solvents may be used as mixtures. Preferred examples of the solvent include ethyl acetate, toluene, and tetrahydrofuran.

The amount of use of the solvent is not particularly limited; however, the amount of use is preferably 1 to 50 times (v/w), and more preferably 1 to 20 times (v/w), the amount of the compound represented by Formula (A6).

[Suitable Embodiment of Method for Manufacturing Compound Represented by Formula (1) (5th)]

It is preferable that the compound represented by Formula (1) is produced by the following scheme. Through the following method, the compound represented by Formula (1) can be produced efficiently.

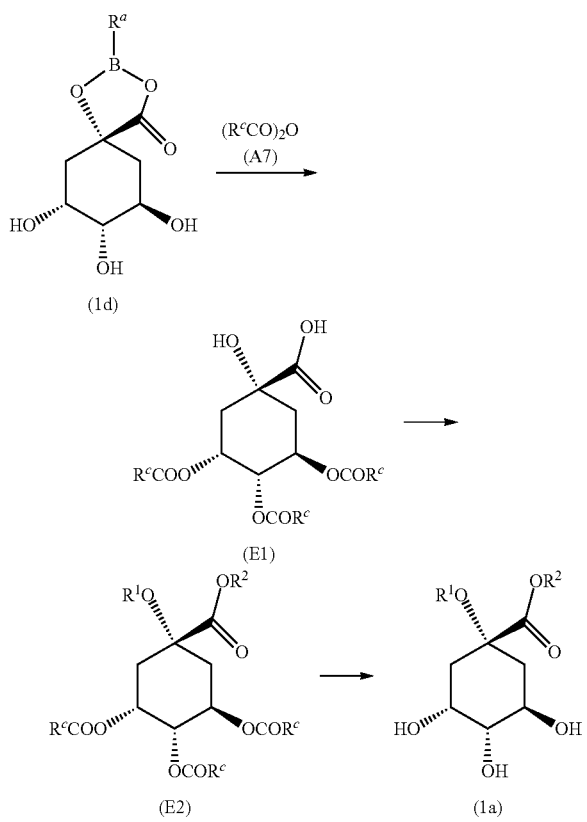

A compound represented by Formula (E1) can be produced by allowing a compound represented by Formula (1d) to react with a compound represented by Formula (A7).

In Formula (A7), $R^C$ represents a halogenated alkyl group, and examples thereof include a trifluoromethyl group, a trichloromethyl group, and a monochloromethyl group.

The present invention may be carried out in the presence of a base, if necessary. When a base is present, the reaction proceeds more efficiently, and the yield is increased. Regarding the kind of the base used therein, the bases mentioned for the method M1 described above, and the like may be used.

Furthermore, in the present reaction, a solvent may be used, if necessary.

The solvent used therein is not particularly limited as long as the solvent does not affect the reaction, and examples thereof include the solvents mentioned for the method M1 described above, and the like.

Meanwhile, in the above-described embodiment, a so-called acid anhydride is used as the compound represented by Formula (A7); however, a compound represented by Formula (8): $R^cCOX^2$ may also be used. $X^2$ therein represents a halogen atom.

A compound represented by Formula (E2) can be produced by protecting at least one of a hydroxyl group and a carboxyl group in the compound represented by Formula (E1).

The method for protection is not particularly limited, and for example, there is available a method of allowing a chloroformic acid ester ($ClCOOR^d$) such as methyl chloroformate, ethyl chloroformate, or trichloroethyl chloroformate, to react with a compound represented by Formula (E1). $R^d$ represents an alkyl group which may be substituted with a halogen atom. In a case in which the chloroformic acid ester and the compound represented by Formula (E1) are caused to react, $R^1$ in Formula (E2) represents —CO-$OR^d$, and $R^2$ represents —$R^d$.

In the case of using a chloroformic acid ester, it is preferable that the reaction is carried out in the presence of the base described above, from the viewpoint that the reaction proceeds more efficiently.

There are no particular limitations on the reaction conditions in the case of using a chloroformic acid ester; however, from the viewpoint that the reaction proceeds efficiently, the reaction temperature is preferably −10° C. to 20° C., and more preferably −5° C. to 10° C., and the reaction time is preferably 30 minutes to 4 hours, and more preferably 1 to 3 hours.

Regarding a method other than the method of using a chloroformic acid ester as described above, for example, the methods mentioned in the section [Suitable embodiment of method for manufacturing compound represented by Formula (1) (1st)] described above may be employed.

A compound represented by Formula (1a) can be produced by deprotecting the compound represented by Formula (E2).

This reaction may be carried out according to the methods described in, for example, Protective Groups in Organic Synthesis, 4th Ed., pp. 16-366, 2007, John Wiley & Sons, Inc.

For example, a preferred example of the method for deprotection in the case of using the above-described chloroformic acid esters, is a method of allowing a compound represented by Formula (E2) to react with water in the presence of a base. The kinds of the base are as described above.

[Suitable Embodiment of Method for Manufacturing Compound Represented by Formula (4)]

The method for manufacturing the compound represented by Formula (4) described above is not particularly limited, and any known methods can be carried out in appropriate combination. Among them, it is preferable that the compound represented by Formula (4) is produced by the following scheme, from the viewpoint of achieving excellent productivity.

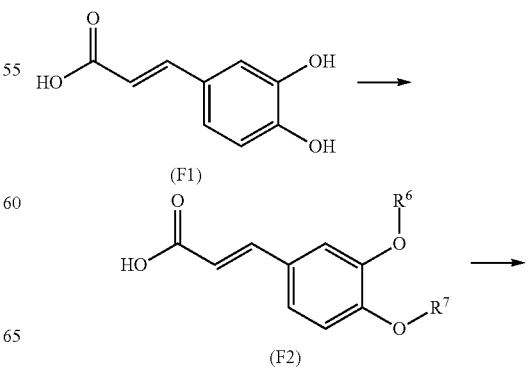

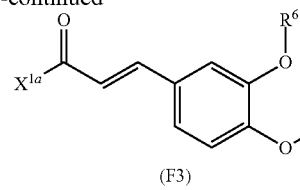

(F3)

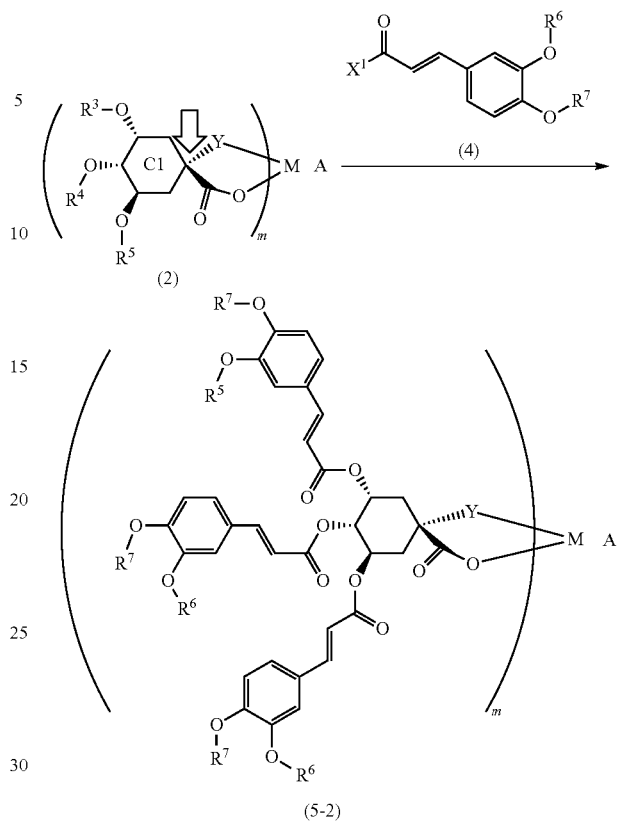

A compound represented by Formula (F2) can be produced by protecting a compound represented by Formula (F1).

This reaction may be carried out according to the methods described in, for example, W. Greene, et al., Protective Groups in Organic Synthesis, $4^{th}$ Ed., pp. 370-424, 2007, John Wiley & Sons, Inc.

For example, a method of allowing a compound represented by Formula (F1) to react with an alkyl chloroformate in the presence of a base may be employed.

A compound represented by Formula (F3) can be produced by allowing a compound represented by Formula (F2) to react with a halogenating agent such as thionyl chloride, thionyl bromide, phosphorus oxychloride, or oxalyl chloride.

The present reaction may be carried out according to the method M2 described above.

When a compound represented by Formula (F3) is obtained, a method of allowing a compound represented by Formula (F2) to react with a halogenating agent, subsequently cooling the reaction liquid, and thereby precipitating and collecting a compound represented by Formula (F3), is available. When a compound represented by Formula (F3) that is obtainable by the relevant method is used, the above-described reaction between the compound represented by Formula (F3) and a compound represented by Formula (1) or a compound represented by Formula (2) proceeds more efficiently. Additionally, the purity of the precipitated compound represented by Formula (F3) may be increased, if necessary, by washing the compound with a solvent.

Second Exemplary Embodiment

A second exemplary embodiment of the manufacturing method of the invention includes Step (B1) of allowing a compound represented by Formula (2) to react with a compound represented by Formula (4), and producing a compound represented by Formula (5-2); and Step (B2) of deprotecting the product obtained in Step (B1), and producing 3,4,5-tricaffeoylquinic acid.

In the following, the compounds used in each step, and the procedure of the steps are described in detail.

[Step (B1)]

Step (B1) is a step of allowing a compound represented by Formula (2) to react with a compound represented by Formula (4), and producing a compound represented by Formula (5-2), as illustrated in the following scheme.

First, the compounds used in the present step are described in detail.

In Formula (2), the definitions of $R^3$ to $R^5$ are as described above.

Y represents $*_1$—$OR^b$. $R^b$ either does not exist, or represents a hydrogen atom. In a case in which $R^b$ does not exist, Y represents —O—, and one of the direct bonds is bonded to a carbon atom represented by C1, and the other direct bond is bonded to M that will be described below.

Meanwhile, $*_1$ represents the position of bonding to the carbon atom represented by C1. The carbon atom represented by C1 is intended to mean a carbon atom represented by a white arrow in the above scheme.

M represents a boron atom, a silicon atom, a divalent metal ion, or a trivalent metal ion. Examples of the divalent metal ion include a calcium ion, a magnesium ion, a zinc ion, an iron ion, a cobalt ion, a chromium ion, a copper ion, and a nickel ion. Furthermore, examples of a trivalent metal ion include an iron ion and an aluminum ion.

Among them, from the viewpoint that excellent adaptability to synthesis of the compound represented by Formula (2) is obtained, and the reaction proceeds more efficiently, a boron atom, a calcium ion, a magnesium ion, and a zinc ion are preferred, and a boron atom and a zinc ion are more preferred.

A either does not exist, or represents a monovalent cation.

Examples of the monovalent cation include alkali metal ions. Among them, from the viewpoint that excellent adaptability to synthesis of the compound represented by Formula (2) is obtained, and isolation is achieved easily, a potassium ion and a sodium ion are preferred.

m represents an integer of 2 or 3. Incidentally, m varies depending on the kind of M.

As a first embodiment, when M is a boron atom, m represents 2, and A represents a monovalent cation. As a second embodiment, when M is a silicon atom, m represents 2, and A does not exist. As a third embodiment, when M is a divalent metal ion, m represents 2, and A does not exist. As a fourth embodiment, when M is a trivalent metal ion, m represents 3, and A does not exist. The respective embodiments are illustrated in the following structural formulas. In the following, the compound represented by Formula (2-1) corresponds to the first embodiment; the compound represented by Formula (2-2) corresponds to the second embodiment; the compound represented by Formula (2-3) corresponds to the third embodiment; and the compound represented by Formula (2-4) corresponds to the fourth embodiment.

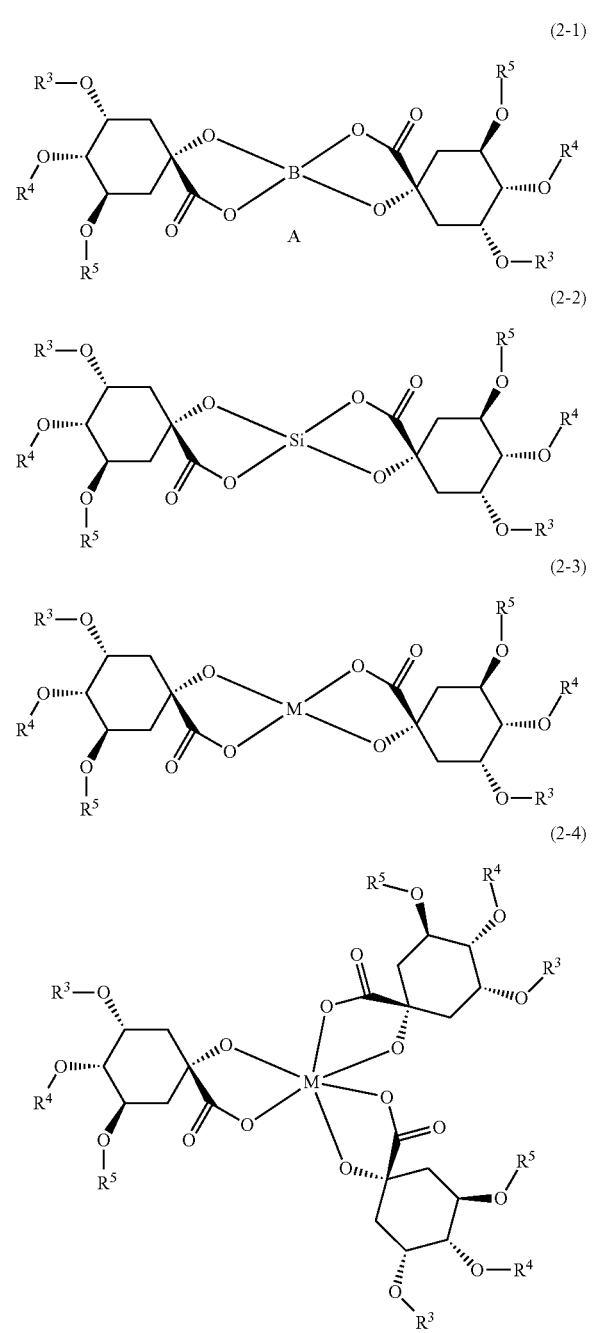

The definition of the compound represented by Formula (4) used in Step (B1) is as described above.

Additionally, Step (B1) may be carried out according to the method mentioned in Step (A1) described above.

[Step (B2)]

Step (B2) is a step of deprotecting the product obtained in Step (B1) (compound represented by Formula (5-2)), and producing 3,4,5-tricaffeoylquinic acid, as illustrated in the following scheme. More specifically, Step (B2) is a step of detaching the protective groups contained in the compound represented by Formula (5-2) (a phenolic hydroxyl protective group and the like), and obtaining desired 3,4,5-tricaffeoylquinic acid.

The term deprotection as used in the present step is intended to mean detachment of the groups that protect a hydroxyl group, a phenolic hydroxyl group, and a carboxyl group in 3,4,5-tricaffeoylquinic acid as described above. Therefore, detaching the moiety represented by M is also included in the term deprotection.

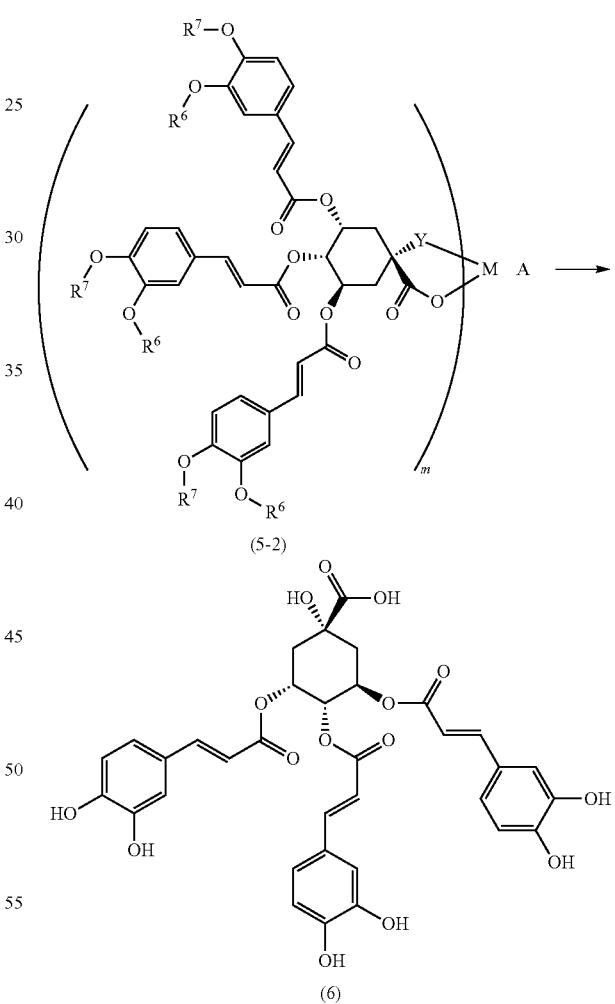

A compound represented by Formula (6) can be produced by deprotecting the compound represented by Formula (5-2).

This reaction may be carried out according to the methods described in, for example, Protective Groups in Organic Synthesis, 4$^{th}$ Ed., pp. 367-430, 2007, John Wiley & Sons, Inc.

The present reaction may be carried out according to the method mentioned in Step (A2) described above.

Regarding a suitable embodiment of Step (B2), as illustrated in the following scheme, a method of producing a compound represented by Formula (5-3) from a compound represented by Formula (5-2), subsequently deprotecting the compound represented by Formula (5-3), and thereby producing a compound represented by Formula (6) may be employed. According to the following scheme, a compound represented by Formula (6) can be produced more efficiently.

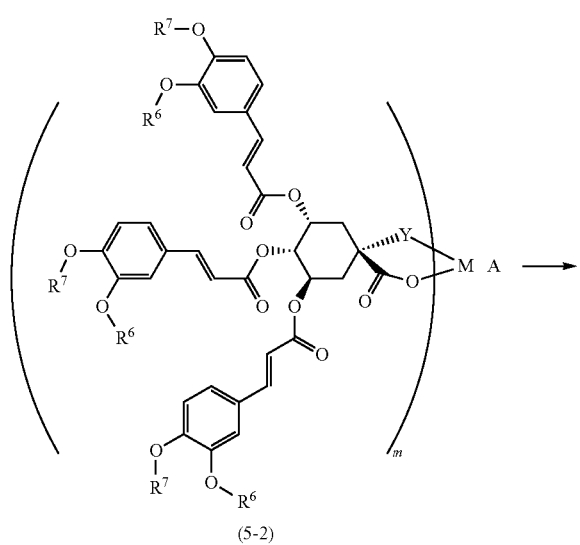

(5-2)

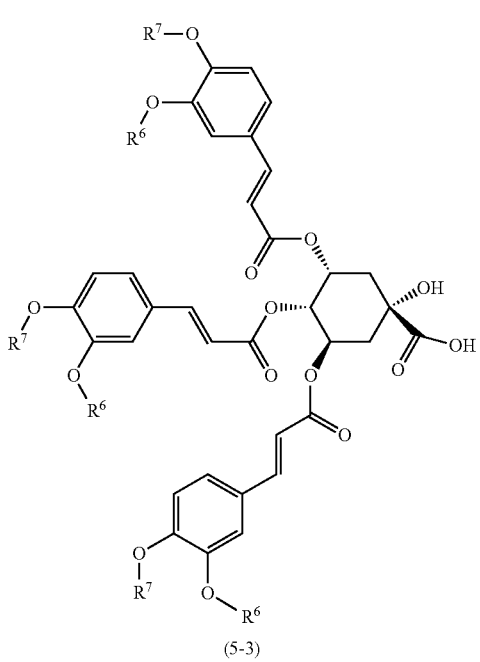

(5-3)

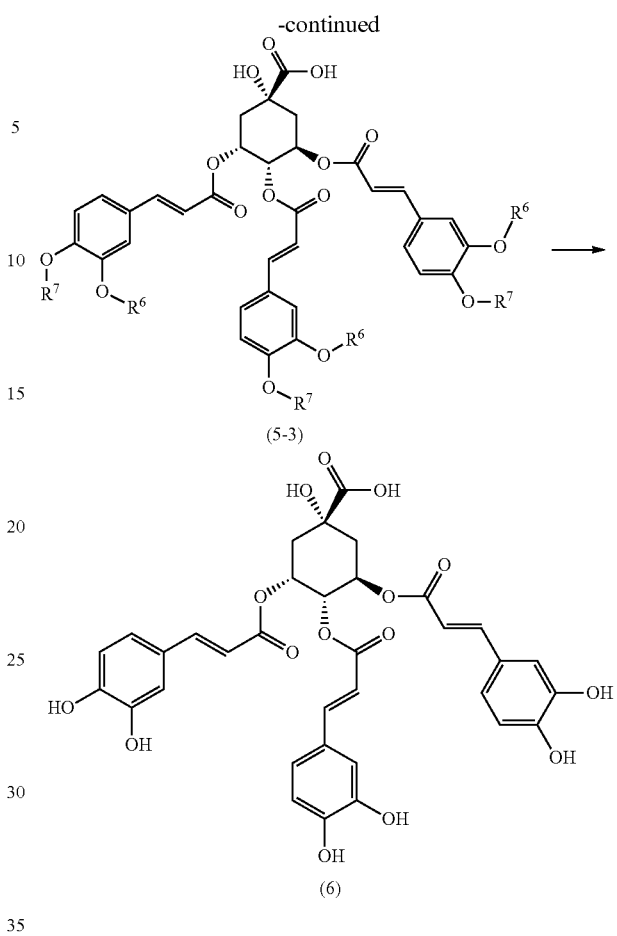

(5-3)

(6)

The method for manufacturing a compound represented by Formula (5-3) from a compound represented by Formula (5-2) is not particularly limited; however, from the viewpoint of obtaining the compound represented by Formula (5-3) efficiently, a method of bringing the compound represented by Formula (5-2) into contact with an acidic aqueous solution or an aqueous solution of a chelating agent may be employed.

There are no particular limitations on the kind of the acid included in the acidic aqueous solution; however, examples thereof include phosphoric acid, hydrochloric acid, and sulfuric acid.

Furthermore, examples of the chelating agent included in the aqueous solution of a chelating agent include EDTA (Ethylenediamine tetraacetic acid) and PDTA (1,3-Propanediamine tetraacetic acid).

The temperature of the acidic aqueous solution and the aqueous solution of a chelating agent is not particularly limited; however, from the viewpoint that the reaction proceeds more efficiently, the temperature is preferably 0° C. to 40° C., and more preferably 10° C. to 30° C.

The time for the reaction between the compound represented by Formula (5-2) or the acidic aqueous solution and the aqueous solution of a chelating agent is not particularly limited; however, the reaction time is preferably 1 minute to 1 hour, and more preferably 3 minutes to 30 minutes, from the viewpoints of the product yield and productivity.

The compound represented by Formula (6) can be produced by deprotecting the compound represented by Formula (5-3).

This reaction may be carried out according to the methods described in, for example, Protective Groups in Organic Synthesis, 4th Ed., pp. 367-430, 2007, John Wiley & Sons, Inc.

The present reaction may be carried out according to the method mentioned in Step (A2) described above.

The method for manufacturing the compound represented by Formula (2) is not particularly limited, and any known methods can be carried out in appropriate combination. Among them, it is preferable that the compound represented by Formula (2) is produced by a method of using quinic acid as a starting raw material, in view of obtaining excellent productivity.

An example of the method for manufacturing the compound represented by Formula (2-1) is a method of allowing quinic acid to react with boric acid in the presence of a base. At that time, a cation exists, and the kind of the cation varies depending on the kind of the base used.

Furthermore, regarding a general method for manufacturing the compounds represented by formulas (2-1) to (2-4), a method of allowing equimolar amounts of quinic acid and boric acid or a derivative, a tetraalkoxysilane, or various metal ions to react with each other in water or methanol at room temperature to 50° C., and after the reaction, distilling off the solvent under reduced pressure, may be employed.

After completion of the reactions of each step and each method described above, isolation and purification can be carried out, if necessary, by the separation and purification treatment described above. Also, the compounds obtainable by each step and each method may be used directly in the subsequent reactions without isolating the compounds.

EXAMPLES

Hereinafter, the invention will be described in detail by way of Examples; however, the invention is not intended to be limited by these Examples.

$^1$H-NMR spectra were analyzed using tetramethylsilane as an internal reference, and using a Bruker AV300 (manufactured by Bruker Corp.).

In the Examples, Me means methyl.

Synthesis Example 1

Synthesis of (1A)

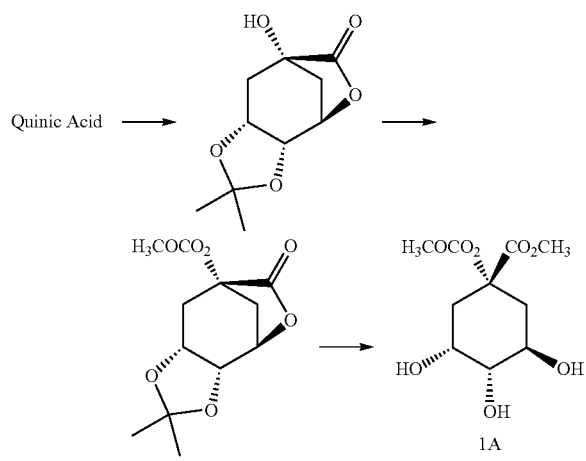

5 mL of sulfuric acid was added dropwise under stirring to a mixture of 100 g of quinic acid, 500 g of anhydrous sodium sulfate, and 2500 mL of acetone, and the mixture was heated to reflux for 5 hours. After the mixture was left to cool naturally, 200 mL of a 5% aqueous solution of sodium hydrogen carbonate was added dropwise thereto to neutralize sulfuric acid, and the solvent was distilled off under reduced pressure. 1500 mL of ethyl acetate was added to the residue, and the mixture was washed with a 5% aqueous solution of sodium hydrogen carbonate and then with a saline solution. Subsequently, the mixture was dried over anhydrous magnesium sulfate, and ethyl acetate was distilled off under reduced pressure. Thus, 104 g of 3,4-O-isopropylidene-1,5-quinide lactone was obtained.

11.6 mL of methyl chloroformate was added dropwise to a mixture of 21.4 g of 3,4-O-isopropylidene-1,5-quinide lactone, 80 mL of pyridine, and 100 mL of methylene chloride under ice cooling at 0° C. to 5° C. After the mixture was stirred for 1 hour at 5° C., 11.6 mL of methyl chloroformate was further added dropwise to the mixture under ice cooling, and the resulting mixture was stirred for 2 hours at 5° C. The reaction liquid was poured into 1 L of cold dilute hydrochloric acid, 300 mL of ethyl acetate was added thereto, and an organic layer was partitioned. The organic layer was washed with a saline solution and dried over anhydrous magnesium sulfate, and the solvent was distilled off under reduced pressure. The residue was recrystallized from hexane/isopropanol, and thus 18.5 g of white crystals of 1-carbomethoxy-3,4-O-isopropylidene-1,5-quinide lactone were obtained.

Five droplets of methanesulfonic acid were added to a mixture of 5.44 g of the white crystals thus obtained and 200 mL of methanol, and the mixture was heated and stirred for 5 hours at 60° C. The solvent was distilled off under reduced pressure, 100 mL of ethyl acetate and 2.0 g of sodium hydrogen carbonate were added to the residue, and the mixture was stirred for 30 minutes at room temperature. Subsequently, insoluble materials were separated off by filtration, and the solvent was distilled off from the filtrate under reduced pressure. The residue was recrystallized from hexane/ethyl acetate, and thus 4.5 g of white crystals of 1A were obtained. The $^1$H-NMR spectrum of 1A (solvent: CDCl$_3$) is presented in FIG. 1.

Synthesis Example 2

Synthesis of (1B)

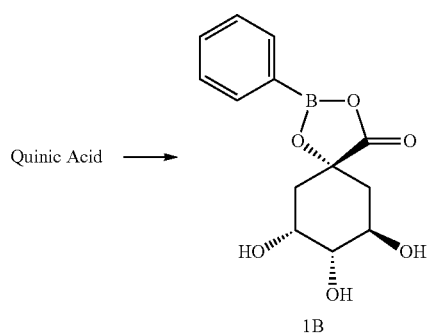 [SMILES: O=C1OB(c2ccccc2)O[C@]12C[C@@H](O)[C@@H](O)[C@H](O)C2]

Figure 2:
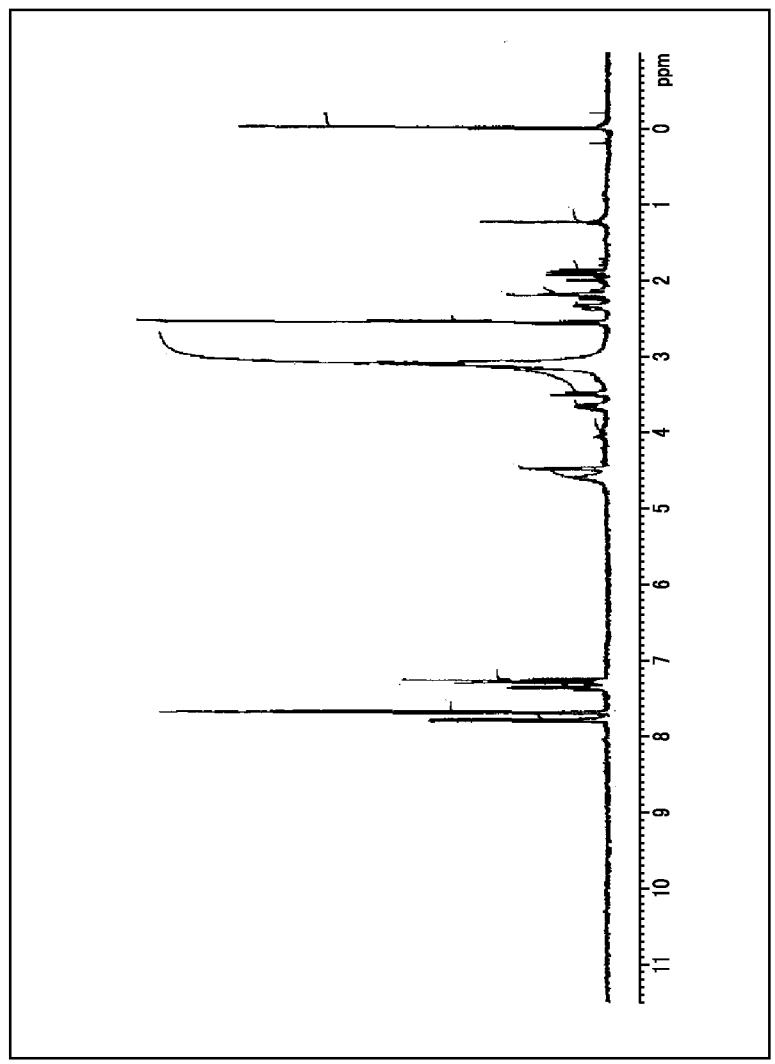
FIG. 2 is the $^1$H-NMR spectrum of 1B synthesized in Synthesis Example 2.

A mixture of 5.76 g of quinic acid, 3.65 g of phenylboric acid, 30 g of anhydrous sodium sulfate, and 100 mL of tetrahydrofuran was heated to reflux for 5 hours. After the mixture was left to cool naturally, sodium sulfate was separated off by filtration, the solvent was distilled off from the filtrate under reduced pressure, and thus 7.3 g of a white solid of 1B was obtained. The ¹H-NMR spectrum of 1B (solvent: DMSO-d₆) is presented in FIG. 2.

Synthesis Example 3

Synthesis of (1C)

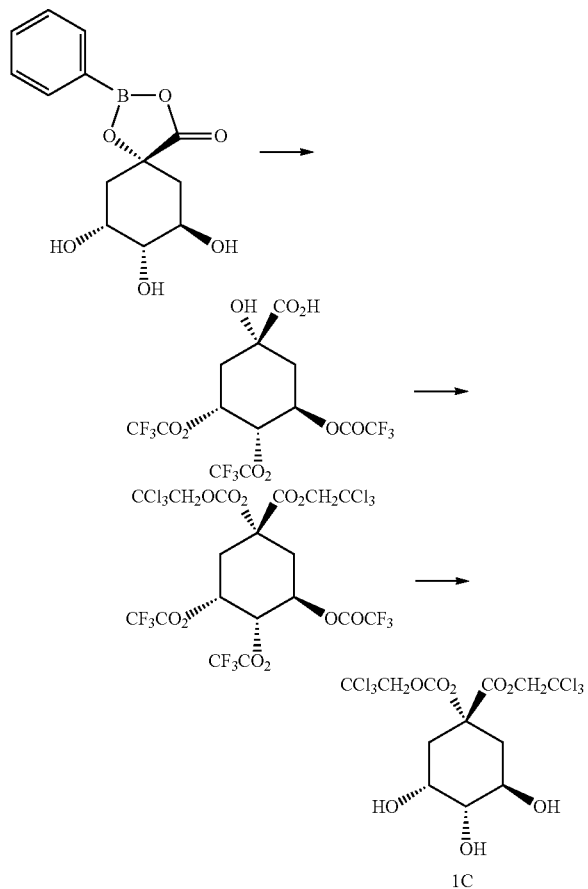

28 mL of trifluoroacetic anhydride was added dropwise to a mixture of 1B (13.9 g) synthesized in Synthesis Example 2, 80 mL of pyridine, and 60 mL of methylene chloride at 0° C. to 3° C. After the mixture was stirred for 2 hours at 5° C. to 10° C., the mixture was poured into cold dilute hydrochloric acid, and extraction was performed using ethyl acetate. The extract was washed with a saline solution, and then dried over anhydrous magnesium sulfate, and the solvent was distilled off under reduced pressure. 40 mL of pyridine and 40 mL of methylene chloride were added to the residue, and under ice cooling, 26.8 mL of trichloroethyl chloroformate was added dropwise to the mixture at 0° C. to 5° C. The resulting mixture was further stirred for 2 hours at 10° C. to 15° C. The reaction liquid was poured into cold dilute hydrochloric acid, and extraction was performed using ethyl acetate. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 21.3 g of trichloroethyl 1-trichlorocarboethoxy-3,4,5-O-tris(trifluoroacetyl)quinate was obtained.

Trichloroethyl 1-trichlorocarboethoxy-3,4,5-O-tris(trifluoroacetyl)quinate was dissolved in 200 mL of methanol, 25 g of potassium hydrogen carbonate was added thereto, and the mixture was stirred for 3 hours at 0° C. to 5° C. Inorganic materials were separated off by filtration, and then the solvent was distilled off under reduced pressure. 50 mL of water and 200 mL of ethyl acetate were added to the residue, and an organic layer was separated off. The organic layer was dried over anhydrous magnesium sulfate, subsequently ethyl acetate was distilled off under reduced pressure, and the residue was recrystallized from hexane/ethyl acetate. Thus, 9.1 g of white crystals of 1C were obtained.

Synthesis Example 4

Synthesis of (1D)

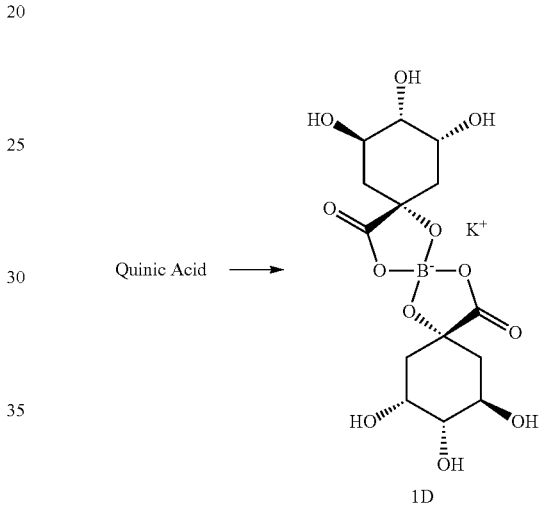

Figure 3:
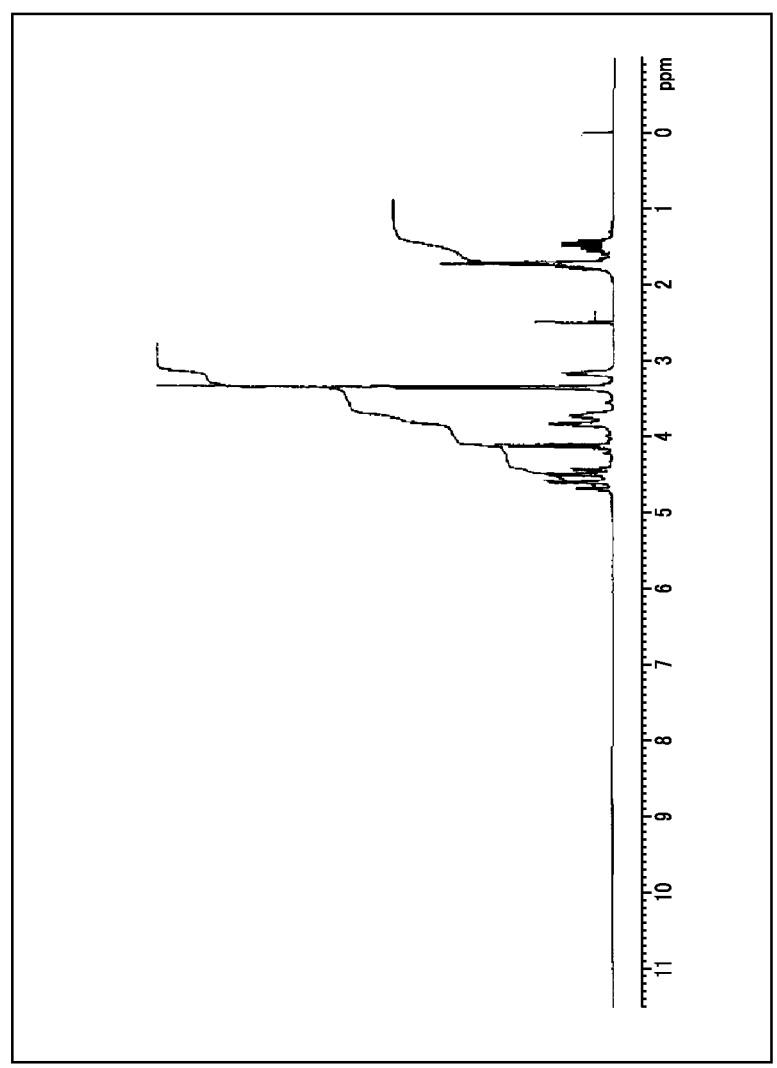
FIG. 3 is the $^1$H-NMR spectrum of 1D synthesized in Synthesis Example 4.

A mixture of 3.84 g of quinic acid, 0.62 g of boric acid, and 10 mL of a 1 N aqueous solution of potassium hydroxide was stirred for 30 minutes at room temperature, and then water was distilled off under reduced pressure. Furthermore, while the mixture was heated to 80° C. by an external heat source, water was completely removed by maintaining a reduced pressure for 3 hours using a vacuum pump. Thus, 4.2 g of a boric acid chelate compound of quinic acid (1D) was obtained. The ¹H-NMR spectrum of 1D (solvent: DMSO-d₆) is presented in FIG. 3.

Synthesis Example 5

Synthesis of (1E)

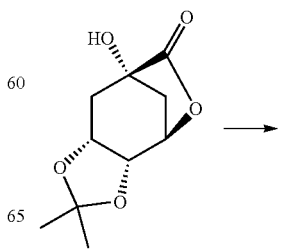

-continued

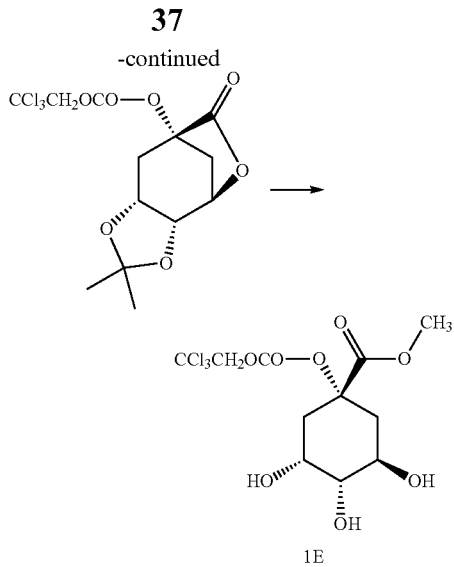

35.0 g of trichloroethyl chloroformate was added dropwise to a mixture of 32.1 g of 3,4-O-isopropylidene-1,5-quinide lactone, 30 mL of pyridine, and 200 mL of methylene chloride under ice cooling at 0° C. to 5° C. The mixture was stirred for 1 hour at 5° C., and then was stirred for 2 hours at room temperature. The reaction liquid was poured into 1 L of cold dilute hydrochloric acid, 500 mL of ethyl acetate was added thereto, and an organic layer was partitioned. The organic layer was washed with a saline solution and then was dried over anhydrous magnesium sulfate, and the solvent was distilled off under reduced pressure. Thus, 57.1 g of a white solid of 1-trichlorocarboethoxy-3,4-O-isopropylidene-1,5-quinide lactone was obtained.

Figure 4:
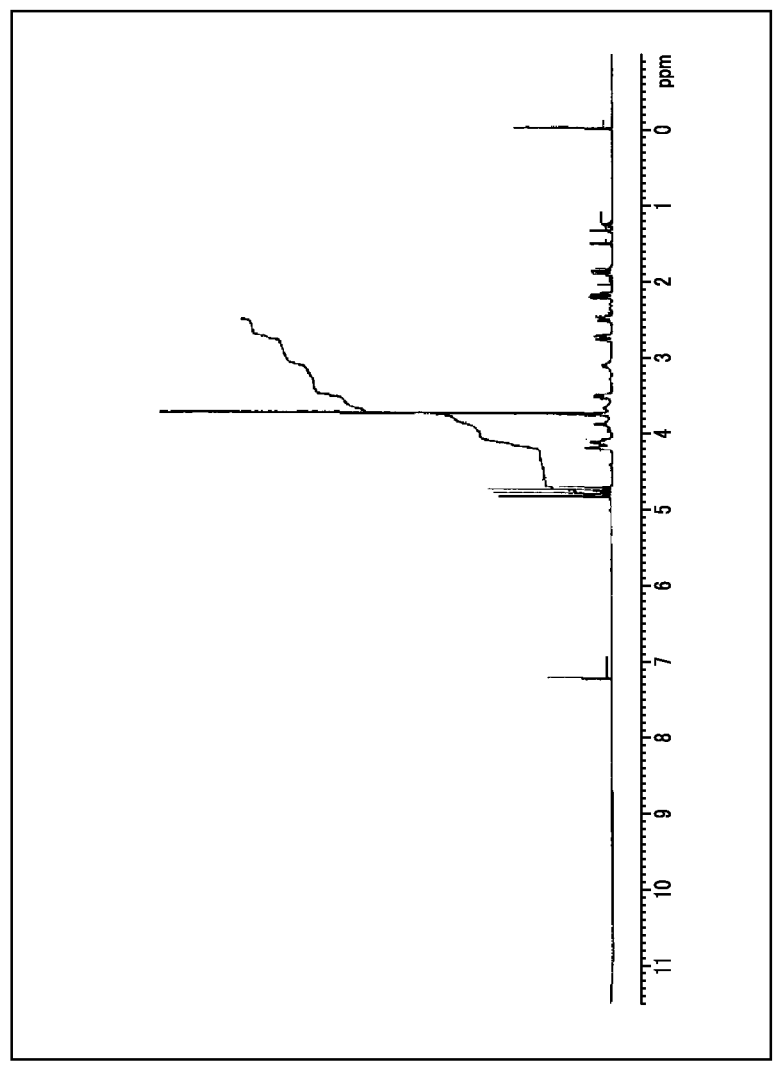
FIG. 4 is the $^1$H-NMR spectrum of 1E synthesized in Synthesis Example 5.

Five droplets of methanesulfonic acid were added to a mixture of 3.9 g of the white solid thus obtained and 40 mL of methanol, and the mixture was heated and stirred for 5 hours at 50° C. After the mixture was left to cool naturally, the solvent was distilled off under reduced pressure. 100 mL of ethyl acetate and 2.0 g of sodium hydrogen carbonate were added to the residue, and the mixture was stirred for 30 minutes at room temperature. Subsequently, insoluble materials were separated off by filtration, and the solvent was distilled off from the filtrate under reduced pressure. The residue was recrystallized from hexane/ethanol, and thus 2.9 g of white crystals of 1E were obtained. The $^1$H-NMR spectrum of 1E (solvent: CDCl$_3$) is presented in FIG. 4.

Synthesis Example 6

Synthesis of (4A)

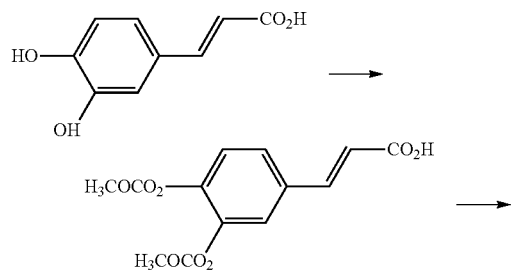

-continued

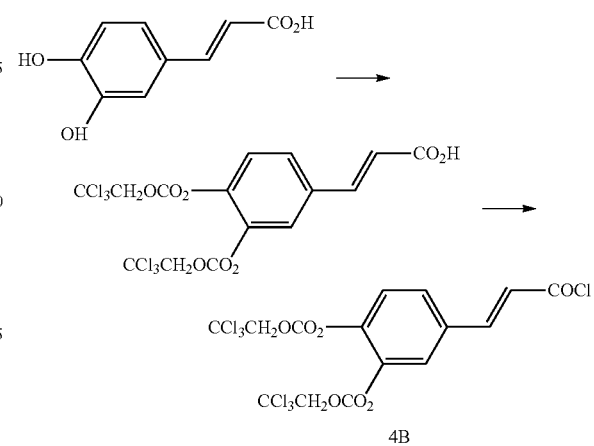

36 g of caffeic acid was dissolved in 400 mL of a 5% aqueous solution of sodium hydroxide, and under a nitrogen gas stream, 69 mL of methyl chloroformate was added dropwise thereto at 0° C. to 3° C. After the mixture was stirred for 1 hour at 5° C. to 10° C., a white solid was collected by filtration and was washed with water. Subsequently, the white solid was recrystallized from hexane/isopropanol, and thus 52.2 g of dicarbomethoxycaffeic acid was obtained.

2.1 mL of oxalyl chloride was added to a mixture of 2.96 g of dicarbomethoxycaffeic acid and 20 mL of toluene, and the mixture was heated and stirred for 2 hours at 60° C. After the mixture was left to cool naturally, the solvent and any excess oxalyl chloride were distilled off under reduced pressure. Thus, 3.1 g of a white solid of 4A was obtained.

Synthesis Example 7

Synthesis of (4B)

3.6 g of caffeic acid was dissolved in 40 mL of a 10% aqueous solution of sodium hydroxide, and under a nitrogen gas stream, 12.7 g of trichloroethyl chloroformate was added dropwise thereto at 0° C. to 5° C. After being stirred for 1 hour at 5° C. to 10° C., the reaction liquid was poured into cold dilute hydrochloric acid, and a white precipitate thus produced was collected by filtration and was recrystallized from isopropanol. Thus, 3.8 g of dicarbotrichloroethoxycaffeic acid was obtained.

30 mL of toluene and 2.5 mL of oxalyl chloride were added to the dicarbotrichloroethoxycaffeic acid thus obtained, and the mixture was heated and stirred for 2 hours at 45° C. to 50° C. After the mixture was left to cool naturally, the solvent and any excess oxalyl chloride were distilled off under reduced pressure, and thus 3.9 g of a white solid of 4B was obtained.

Synthesis Example 8

Synthesis of (4C)

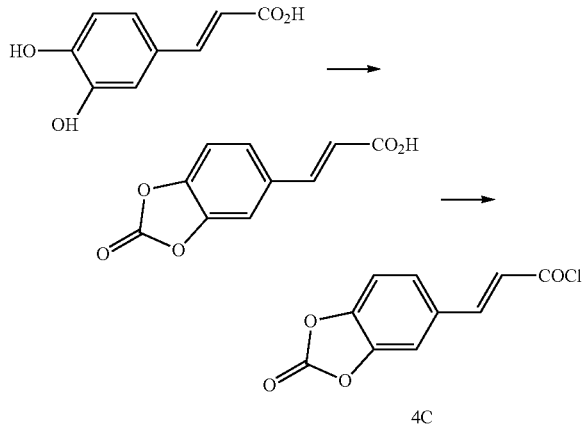

6.42 g of diphenyl carbonate was added to a mixture of 3.6 g of caffeic acid, 5 mL of triethylamine, and 10 mL of dimethylacetamide at room temperature, and the mixture was heated and stirred for 3 hours at 45° C. to 50° C. The reaction liquid was poured into cold dilute hydrochloric acid, and a white precipitate thus produced was collected by filtration and washed with water. Subsequently, the precipitate was recrystallized from acetone/acetic acid, and thus 2.9 g of white crystals of 3,4-carbonyldioxycinnamic acid were obtained.

2.1 mL of oxalyl chloride was added to a mixture of 2.06 g of the 3,4-carbonyldioxycinnamic acid thus obtained and 50 mL of toluene, and the mixture was heated and stirred for 3 hours at 60° C. After the mixture was left to cool naturally, the solvent was distilled off under reduced pressure, and thus 2.2 g of a white solid of 4C was obtained.

Synthesis Example 9

Synthesis of Compound (2)

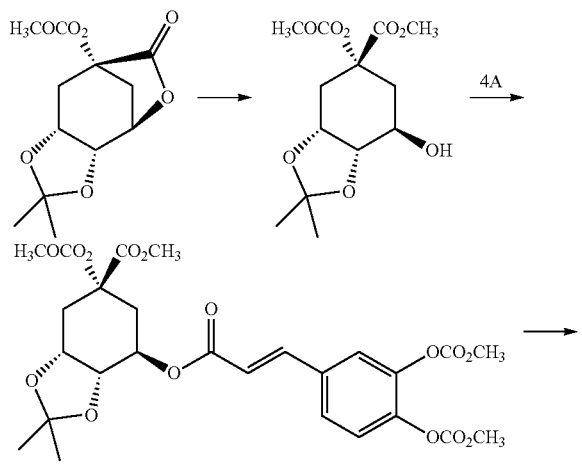

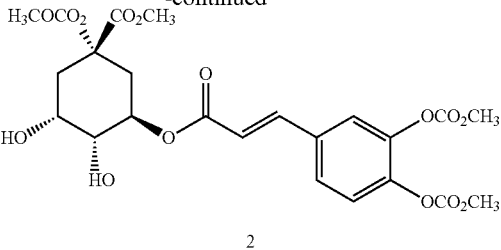

1.38 g of anhydrous potassium carbonate was added to a mixture of 2.72 g of 1-carbomethoxy-3,4-O-isopropylidene-1,5-quinide lactone synthesized in Synthesis Example 1 and 100 mL of methanol, and the mixture was stirred for 2 hours at room temperature. Inorganic materials were separated off by filtration, and then methanol was distilled off under reduced pressure. The residue was purified by silica gel column chromatography (eluent: ethyl acetate/n-hexane), and thus 2.3 g of methyl 1-carbomethoxy-3,4-O-isopropylidenequinate was obtained.

Figure 5:
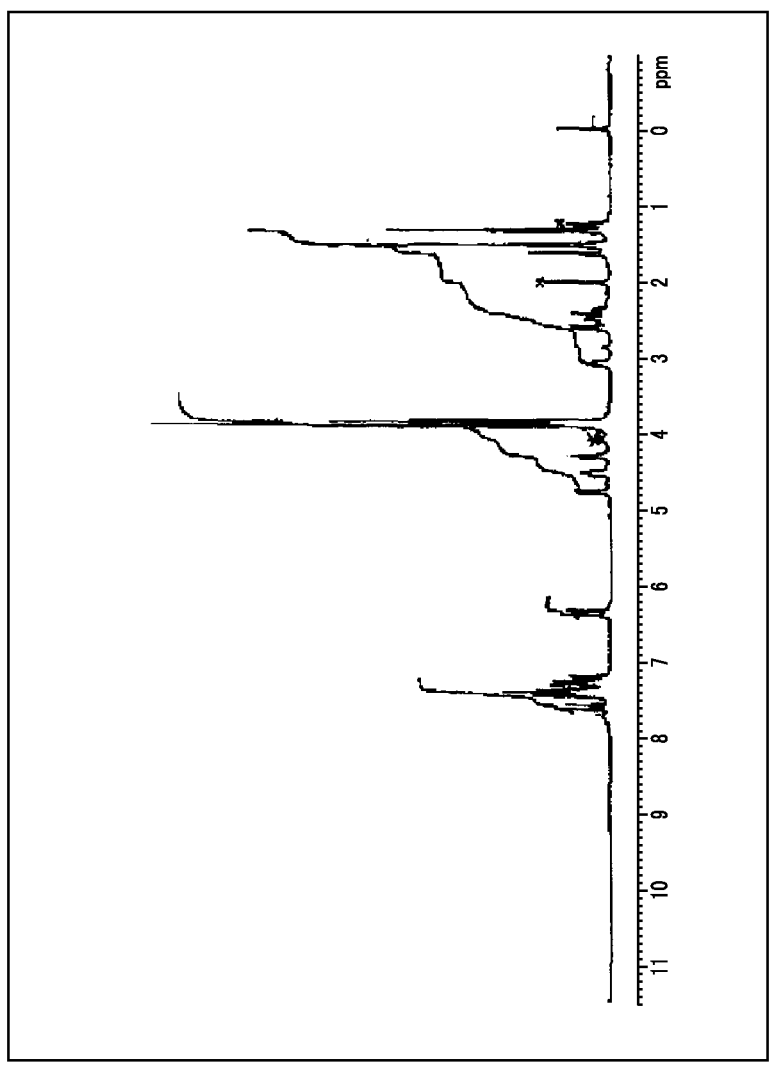
FIG. 5 is the $^1$H-NMR spectrum of methyl 1-carbomethoxy-3,4-O-isopropylidene-5-(3,4-dicarbomethoxycaffeoyl)quinate synthesized in Synthesis Example 9.

4A (2.4 g) synthesized in Synthesis Example 4 was added in small amounts to a mixture of 1.52 g of methyl 1-carbomethoxy-3,4-O-isopropylidenequinate, 2 mL of pyridine, and 20 mL of methylene chloride at −5° C. to 0° C. After being stirred for 3 hours at 0° C. to 5° C., the reaction liquid was poured into cold dilute hydrochloric acid, and extraction was performed using ethyl acetate. The extract was washed with a saline solution, and then the solvent was distilled off under reduced pressure. The residue was purified by silica gel column chromatography (eluent: ethyl acetate/n-hexane), and thus 2.6 g of methyl 1-carbomethoxy-3,4-O-isopropylidene-5-(3,4-dicarbomethoxycaffeoyl)quinate was obtained. The $^1$H-NMR spectrum (solvent: DMSO-$d_6$) is presented in FIG. 5.

30 mL of trifluoroacetic acid and 5 mL of water were added to 1.5 g of methyl 1-carbomethoxy-3,4-O-isopropylidene-5-(3,4-dicarbomethoxycaffeoyl)quinate, and the mixture was stirred for 3 hours at room temperature. Subsequently, the solvent was distilled off under reduced pressure, and the residue was washed with water. Thus, 1.8 g of compound (2) was obtained.

Synthesis Example 10

Synthesis of Compound (3)

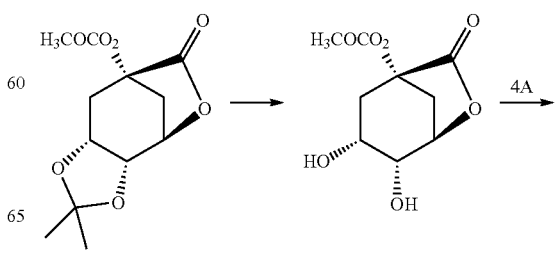

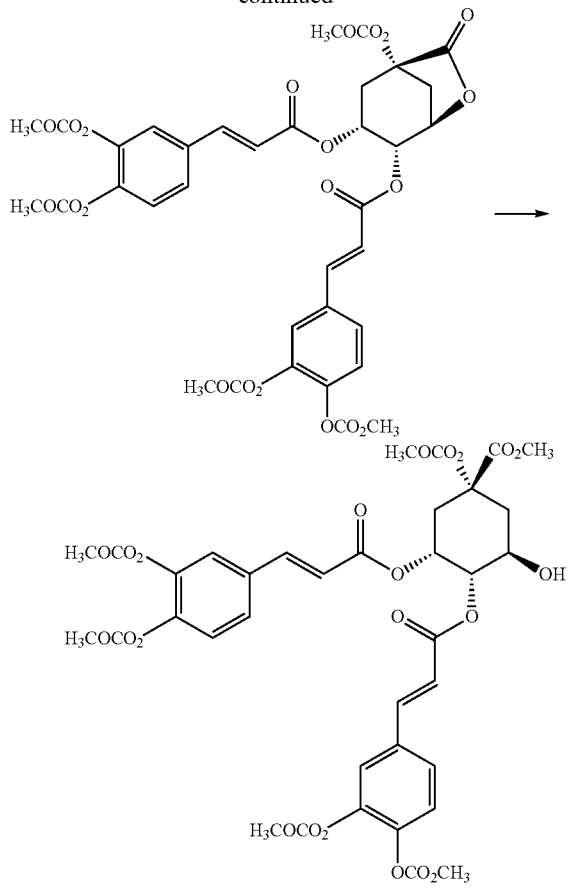

A mixture of 5.0 g of 1-carbomethoxy-3,4-O-isopropylidene-1,5-quinide lactone synthesized in Synthesis Example 1, 25 mL of acetic acid, and 25 mL of water was heated and stirred for 7 hours at 65° C. to 70° C. After the mixture was left to cool naturally, the solvent was distilled off under reduced pressure, and the residue was recrystallized from hexane/isopropanol. Thus, 2.6 g of 1-carbomethoxy-1,5-quinide lactone was obtained.

Figure 6:
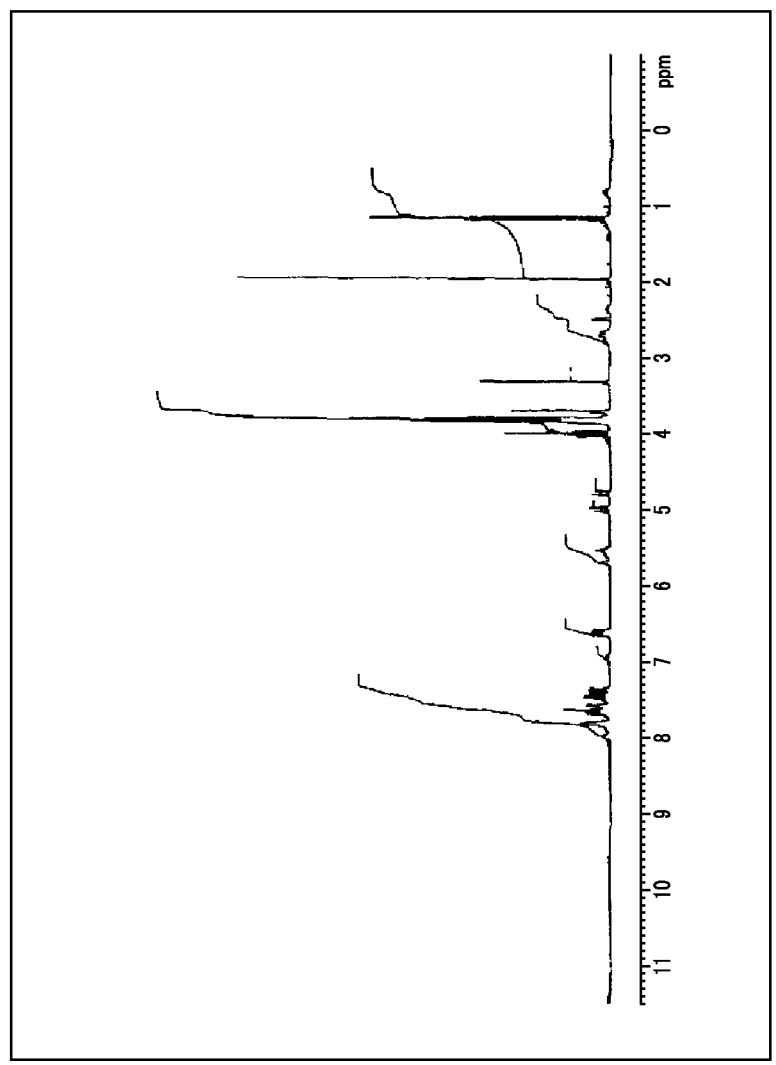
FIG. 6 is the $^1$H-NMR spectrum of 1-carbomethoxy-3,4-bis(3,4-dicarbomethoxycaffeoyl)-1,5-quinide lactone synthesized in Synthesis Example 10.

4A (9.4 g) was added in small amounts to a mixture of 2.32 g of 1-carbomethoxy-1,5-quinide lactone, 4 mL of pyridine, and 40 mL of methylene chloride at −5° C. to 0° C. The mixture was stirred for 5 hours at 0° C. to 5° C., subsequently the reaction liquid was poured into cold dilute hydrochloric acid, and extraction was performed using ethyl acetate. The extract was washed with a saline solution and dried over anhydrous magnesium sulfate, and then the solvent was distilled off under reduced pressure. The residue was purified by silica gel column chromatography (eluent: ethyl acetate/n-hexane), and thus 6.3 g of 1-carbomethoxy-3,4-bis(3,4-dicarbomethoxycaffeoyl)-1,5-quinide lactone was obtained. The $^1$H-NMR spectrum (solvent: DMSO-d6) is presented in FIG. 6.

Five droplets of methanesulfonic acid were added to a mixture of 3.9 g of 1-carbomethoxy-3,4-bis(3,4-dicarbomethoxycaffeoyl)-1,5-quinide lactone and 100 mL of methanol, and the mixture was stirred for 10 hours at room temperature. The solvent was distilled off under reduced pressure, ethyl acetate was added to the residue, and the mixture was washed with a 2% aqueous solution of sodium hydrogen carbonate and a saline solution. Subsequently, the residue was dried over anhydrous magnesium sulfate, and the solvent was distilled off under reduced pressure. The residue was purified by silica gel column chromatography (eluent: ethyl acetate/n-hexane), and thus 3.1 g of compound (3) was obtained.

Synthesis Example 11

Synthesis of 3,4,5-tricaffeoylquinic acid (1$^{st}$)

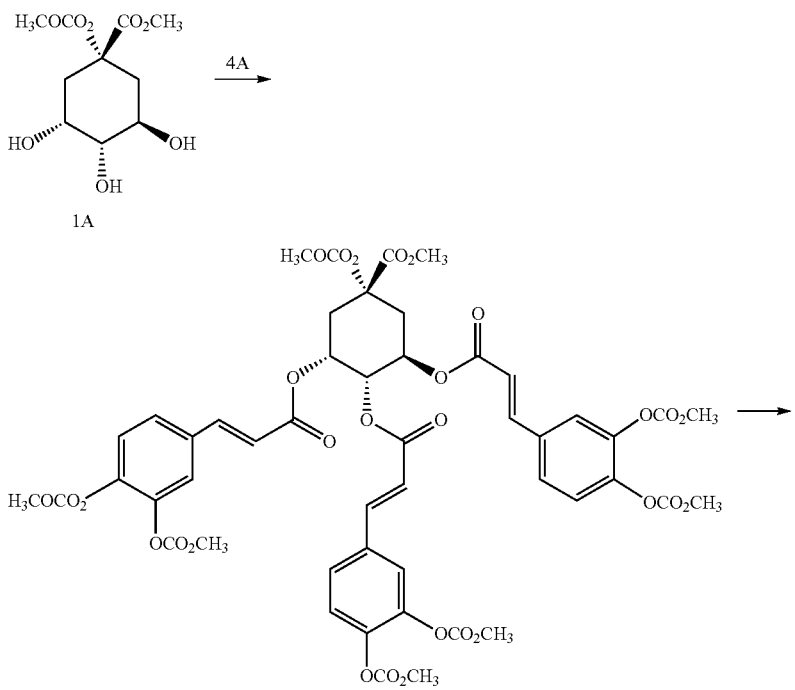

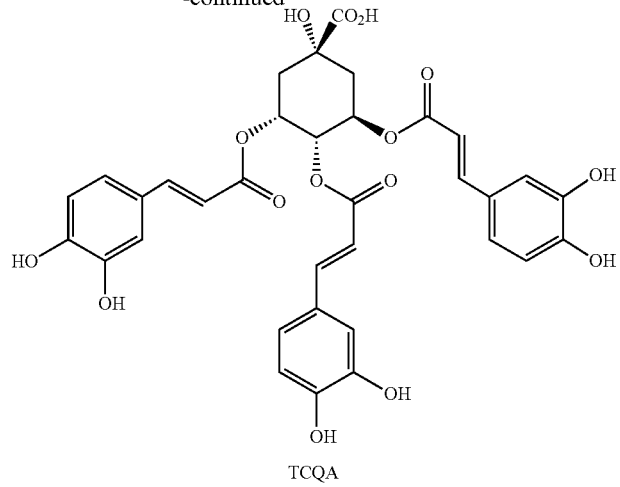

Figure 7:
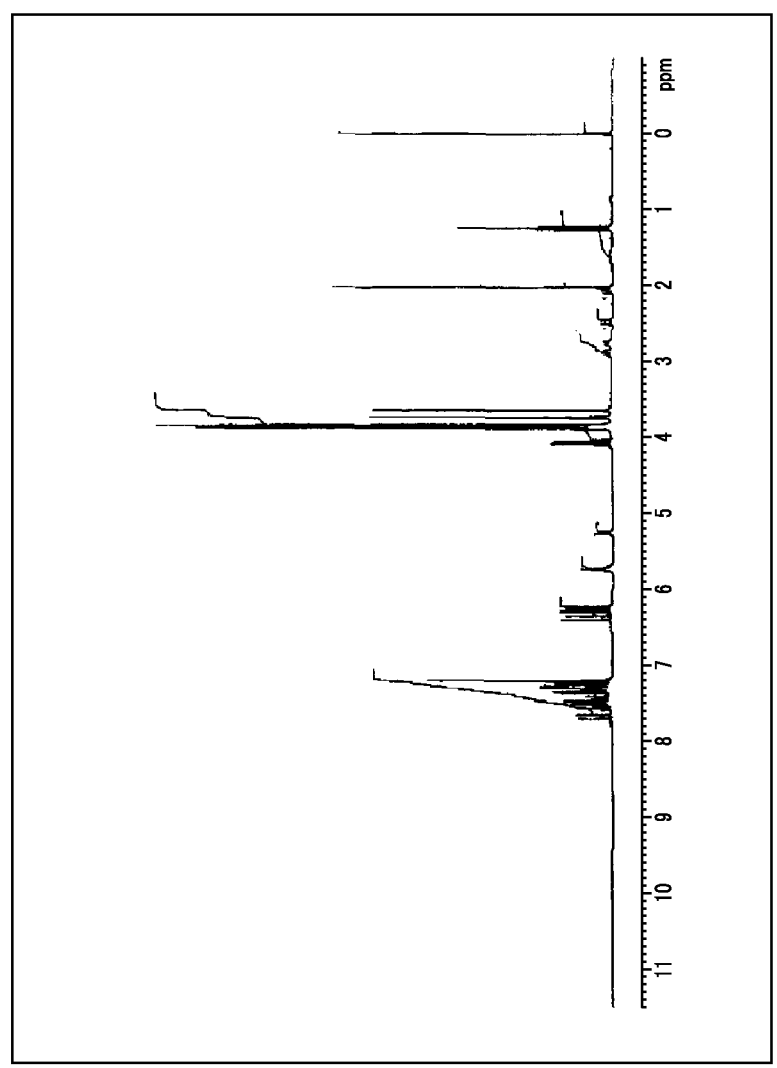
FIG. 7 is the $^1$H-NMR spectrum of methyl 1-carbomethoxy-3,4,5-tris(3,4-dicarbomethoxycaffeoyl)quinate synthesized in Synthesis Example 11.

TCQA 4A (6.3 g) synthesized as described above was added in small amounts to a mixture of 1A (1.32 g) synthesized as described above, 2.5 mL of pyridine, and 35 mL of methylene chloride at −5° C. to 0° C. The mixture was stirred for 1 hour at −5° C. to 0° C. and for 5 hours at 0° C. to 5° C., and then the reaction liquid was poured into cold dilute hydrochloric acid. Ethyl acetate was added to the reaction liquid, and an organic layer was extracted. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 3.8 g of methyl 1-carbomethoxy-3,4,5-tris(3,4-dicarbomethoxycaffeoyl)quinate was obtained. The $^1$H-NMR spectrum (solvent: CDCl$_3$) is presented in FIG. 7.

Figure 8:
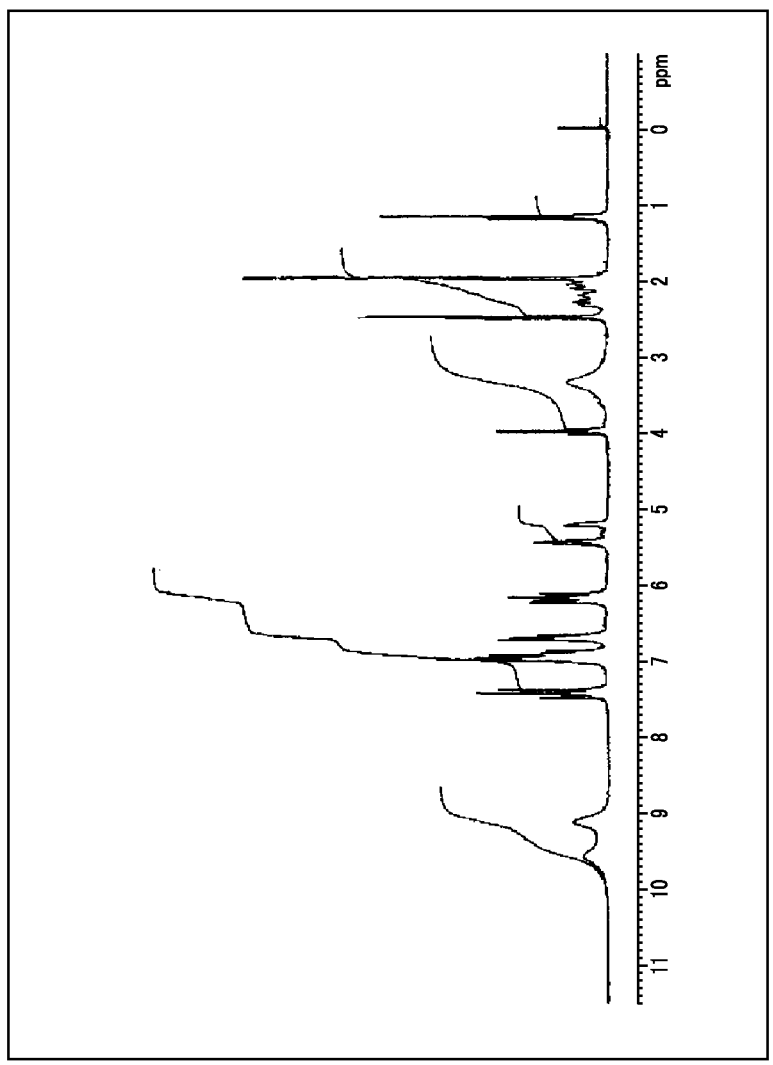
FIG. 8 is the $^1$H-NMR spectrum of 3,4,5-tricaffeoylquinic acid synthesized in Synthesis Example 11.

A mixture of 2.2 g of methyl 1-carbomethoxy-3,4,5-tris(3,4-dicarbomethoxycaffeoyl)quinate, 6.8 g of anhydrous lithium chloride, and 30 mL of pyridine was heated to reflux for 3 hours, subsequently 1.34 g of anhydrous lithium iodide was added thereto, and the resulting mixture was heated to reflux for 2 hours. After the mixture was left to cool naturally, the solvent was distilled off under reduced pressure, and the residue was purified by silica gel column chromatography (eluent: ethyl acetate/n-hexane) and ODS column chromatography. Thus, 0.8 g of 3,4,5-tricaffeoylquinic acid (TCQA) was obtained. The $^1$H-NMR spectrum (solvent: DMSO-d$_6$) is presented in FIG. 8.

Synthesis Example 12

Synthesis of 3,4,5-tricaffeoylquinic acid (2$^{nd}$)

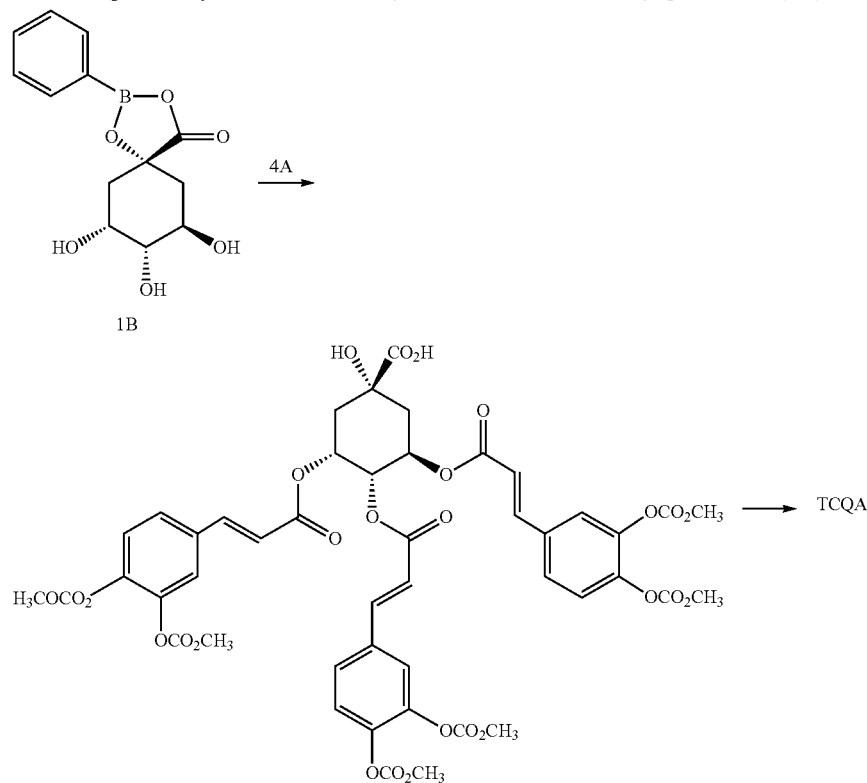

Figure 9:
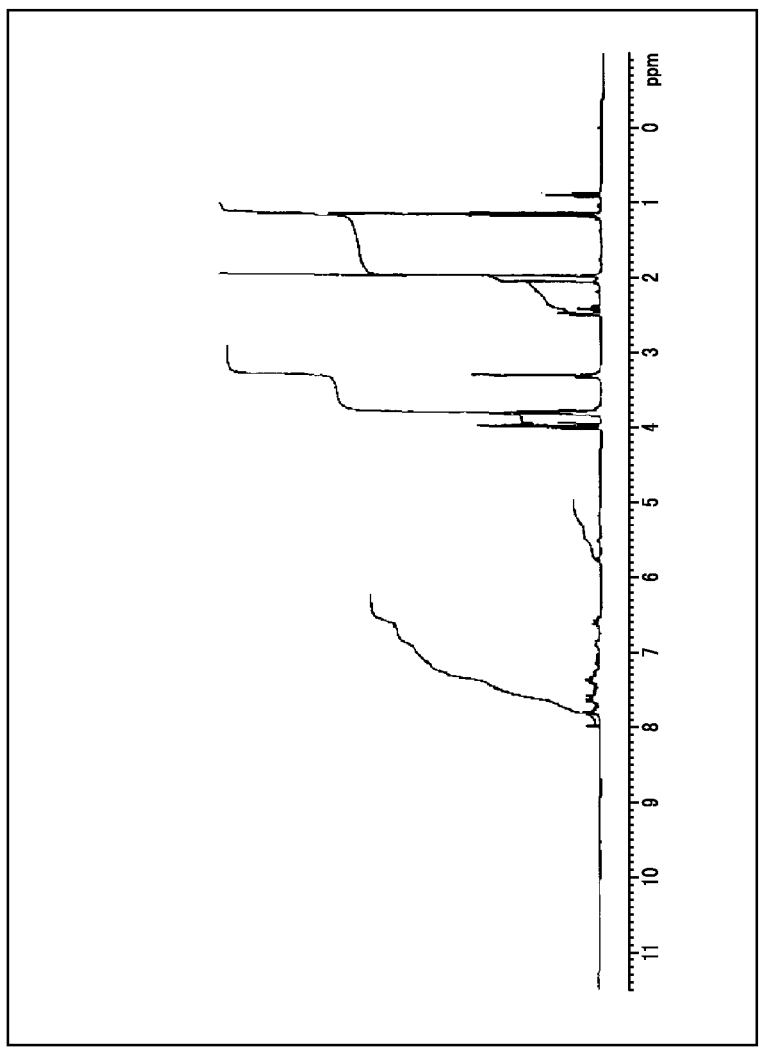
FIG. 9 is the $^1$H-NMR spectrum of 3,4,5-tris(3,4-dicarbomethoxycaffeoyl)quinic acid synthesized in Synthesis Example 12.

4A (6.3 g) synthesized as described above was added in small amounts to a mixture of 1B (1.39 g) synthesized as described above, 2.5 mL of pyridine, and 35 mL of methylene chloride at −5° C. to 0° C. The mixture was stirred for 1 hour at −5° C. to 0° C., for 3 hours at 0° C. to 5° C., and for 3 hours at 5° C. to 10° C., and then the reaction liquid was poured into cold dilute hydrochloric acid. Ethyl acetate was added thereto, and an organic layer was partitioned. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 1.4 g of 3,4,5-tris(3,4-dicarbomethoxycaffeoyl)quinic acid was obtained. The $^1$H-NMR spectrum (solvent: DMSO-$d_6$) is presented in FIG. 9.

A mixture of 1.1 g of 3,4,5-tris(3,4-dicarbomethoxycaffeoyl)quinic acid, 3.2 g of anhydrous lithium chloride, and 30 mL of pyridine was heated to reflux for 3 hours. After the mixture was left to cool naturally, the solvent was distilled off under reduced pressure, and the residue was purified by silica gel column chromatography (eluent: ethyl acetate/n-hexane), and thus 0.4 g of 3,4,5-tricaffeoylquinic acid (TCQA) was obtained.

Synthesis Example 13

Synthesis of 3,4,5-tricaffeoylquinic acid ($3^{rd}$)

4B (11.0 g) synthesized as described above was added in small amounts to a mixture of 1C (2.5 g) synthesized as described above, 2.5 mL of pyridine, and 40 mL of methylene chloride at −5° C. to 0° C. The mixture was stirred for 5 hours at 0° C. to 5° C., and then the reaction liquid was poured into cold dilute hydrochloric acid. Ethyl acetate was added thereto, and an organic layer was partitioned. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 4.9 g of trichloroethyl 1-carbotrichloroethoxy-3,4,5-tris(3,4-dicarbotrichloroethoxycaffeoyl)quinate was obtained.

5.0 g of zinc dust was added under stirring to a mixture of 4.0 g of trichloroethyl 1-carbotrichloroethoxy-3,4,5-tris(3,4-dicarbotrichloroethoxycaffeoyl)quinate, 30 mL of acetic acid, and 30 mL of tetrahydrofuran, and the mixture was heated and stirred for 8 hours at 35° C. to 40° C. Inorganic materials were separated off by filtration, and the inorganic materials were washed with 20 mL of methanol. The filtrate and the washing liquid were combined, and the solvent was distilled off under reduced pressure. 30 mL of water was added to the residue, and the solvent was distilled off again under reduced pressure. The residue was purified by ODS column chromatography, and thus 0.9 g of 3,4,5-tricaffeoylquinic acid (TCQA) was obtained.

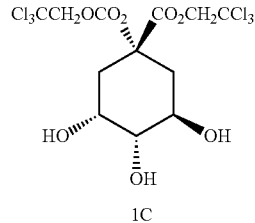

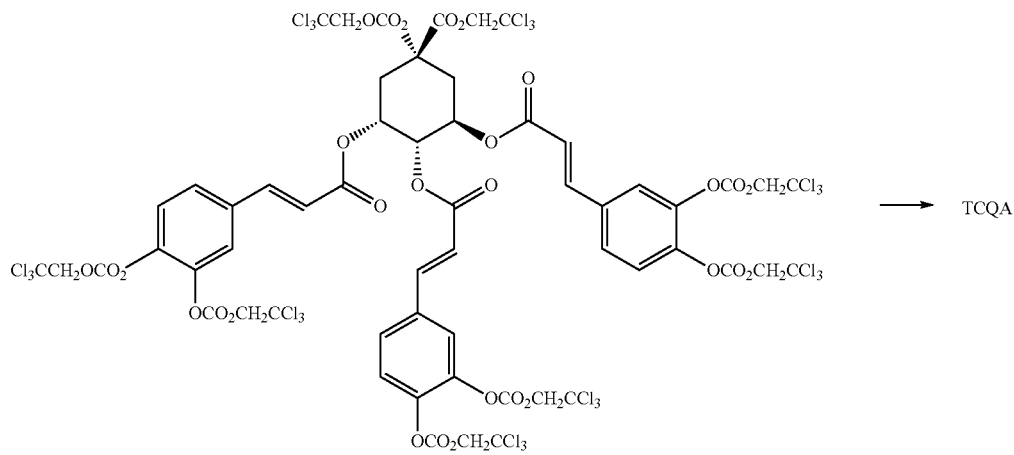

Synthesis Example 14

Synthesis of 3,4,5-tricaffeoylquinic acid (4th)

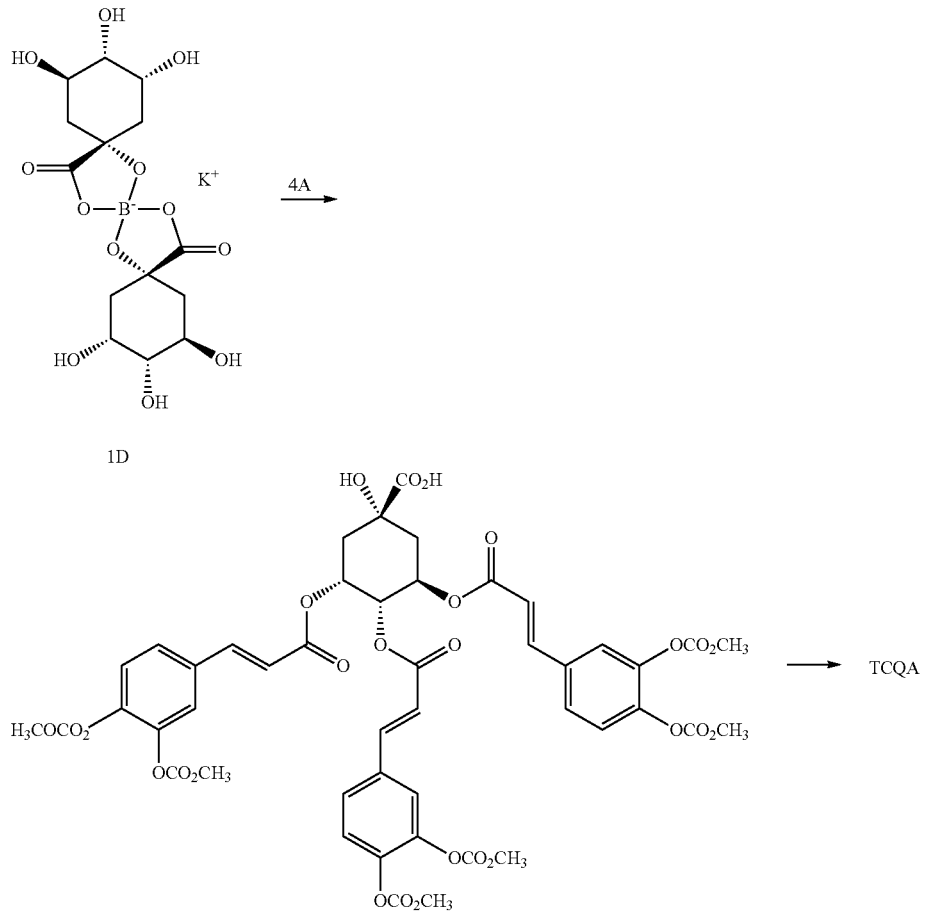

4A (6.3 g) synthesized as described above was added in small amounts to a mixture of 1D (0.83 g) synthesized as described above, 2 mL of pyridine, and 40 mL of dimethylformamide at −5° C. to 0° C. The mixture was stirred for 1 hour at −5° C. to 0° C., for 3 hours at 0° C. to 5° C., and for 3 hours at 5° C. to 10° C., and then the reaction liquid was poured into cold dilute hydrochloric acid. Ethyl acetate was added thereto, and an organic layer was extracted. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 0.25 g of 3,4,5-tris(3,4-dicarbomethoxycaffeoyl)quinic acid was obtained.

A mixture of 0.25 g of 3,4,5-tris(3,4-dicarbomethoxycaffeoyl)quinic acid, 1.2 g of anhydrous lithium chloride, and 10 mL of pyridine was heated to reflux for 4 hours. After the mixture was left to cool naturally, the solvent was distilled off under reduced pressure, and the residue was purified by silica gel column chromatography (eluent: ethyl acetate/n-hexane). Thus, 70 mg of 3,4,5-tricaffeoylquinic acid (TCQA) was obtained.

Synthesis Example 15

Synthesis of 3,4,5-tricaffeoylquinic acid (5th)

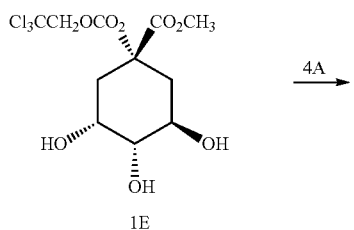

-continued

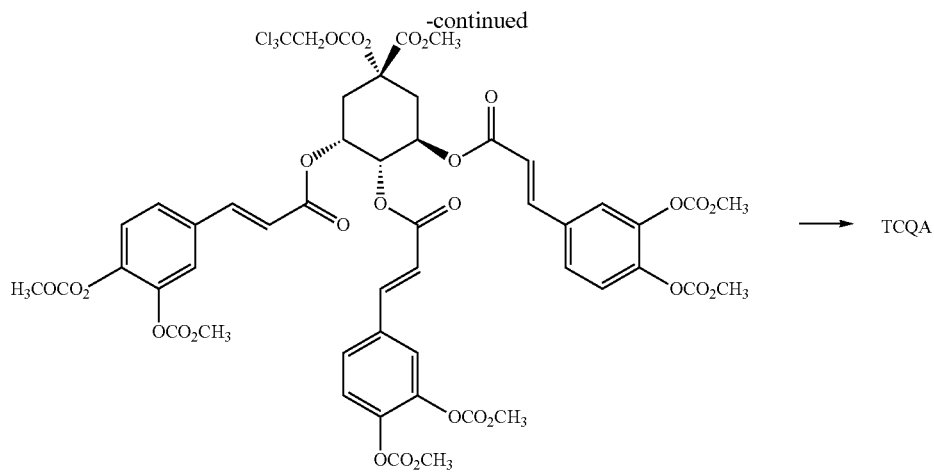

→ TCQA 4A (6.3 g) synthesized as described above was added in small amounts to a mixture of 1E (1.91 g) synthesized as described above, 2 mL of pyridine, and 30 mL of methylene chloride at −5° C. to 0° C. The mixture was stirred for 1 hour at −5° C. to 0° C., and for 5 hours at 0° C. to 5° C., and then the reaction liquid was poured into cold dilute hydrochloric acid. Ethyl acetate was added thereto, and an organic layer was partitioned. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 3.7 g of methyl 1-trichlorocarboethoxy-3,4,5-tris(3,4-dicarbomethoxycaffeoyl)quinate was obtained.

4.0 g of zinc dust was added under stirring to a mixture of 2.4 g of methyl 1-trichlorocarboethoxy-3,4,5-tris(3,4-dicarbomethoxycaffeoyl)quinate, 20 mL of acetic acid, and 20 mL of tetrahydrofuran, and the mixture was heated and stirred for 5 hours at 35° C. to 40° C. Inorganic materials were separated off by filtration, and the inorganic materials were washed with methanol. The filtrate and the washing liquid were combined, and the solvent was distilled off under reduced pressure. 8.7 g of anhydrous lithium bromide and 40 mL of pyridine were added to the residue, and the mixture was heated to reflux for 4 hours. After the mixture was left to cool naturally, the solvent was distilled off under reduced pressure, and the residue was purified by silica gel column chromatography (eluent: ethyl acetate/n-hexane). Thus, 0.7 g of 3,4,5-tricaffeoylquinic acid (TCQA) was obtained.

Synthesis Example 16

Synthesis of 3,4,5-tricaffeoylquinic acid (6$^{th}$)

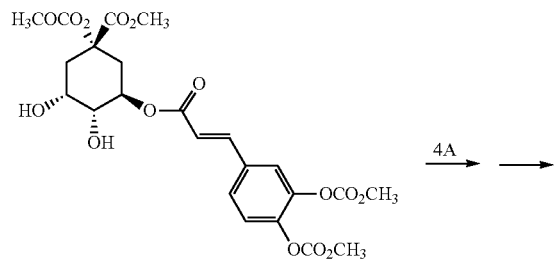

2

→ 4A →

TCQA 4A (2.8 g) synthesized as described above was added in small amounts to a mixture of 1.0 g of the compound (2) synthesized as described above, 2 mL of pyridine, and 20 mL of methylene chloride at −5° C. to 0° C. The mixture was stirred for 1 hour at −5° C. to 0° C. and for 5 hours at 0° C. to 5° C., and then the reaction liquid was poured into cold dilute hydrochloric acid. Ethyl acetate was added thereto, and an organic layer was partitioned. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 1.8 g of methyl 1-carbomethoxy-3,4,5-tris(3,4-dicarbomethoxycaffeoyl)quinate was obtained.

Deprotection was carried out by the same method as that of Synthesis Example 11, and thus 0.8 g of 3,4,5-tricaffeoylquinic acid (TCQA) was obtained.

Synthesis Example 17

Synthesis of 3,4,5-tricaffeoylquinic acid (7$^{th}$)

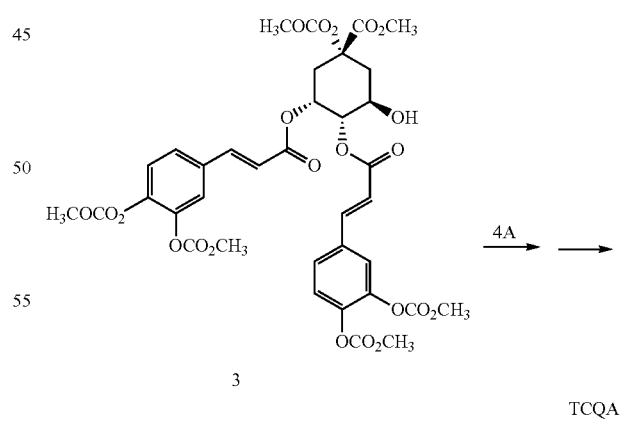

3

→ 4A →

TCQA 4A (2.5 g) synthesized as described above was added in small amounts to a mixture of 1.5 g of the compound (3) synthesized as described above, 2 mL of pyridine, and 25 mL of methylene chloride at −5° C. to 0° C. The mixture was stirred for 1 hour at −5° C. to 0° C. and for 5 hours at 0° C. to 5° C., and then the reaction liquid was poured into cold dilute hydrochloric acid. Ethyl acetate was added thereto, and an organic layer was partitioned. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 1.1 g of methyl 1-carbomethoxy-3,4,5-tris(3,4-dicarbomethoxycaffeoyl)quinate was obtained.

Deprotection was carried out by the same method as that of Synthesis Example 11, and thus 0.4 g of 3,4,5-tricaffeoylquinic acid (TCQA) was obtained.

Synthesis Example 18

Synthesis of 3,4,5-tricaffeoylquinic acid ($8^{th}$)

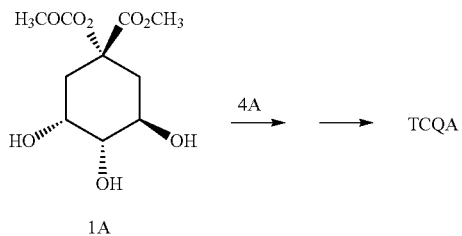

4A (6.3 g) synthesized as described above was added in small amounts to a mixture of 1A (1.32 g), 2.5 mL of pyridine, and 30 mL of dimethylformamide at −5° C. to 0° C. The mixture was stirred for 1 hour at −5° C. to 0° C. and for 5 hours at 0° C. to 5° C., and then the reaction liquid was poured into cold dilute hydrochloric acid. Ethyl acetate was added thereto, and an organic layer was partitioned. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 0.7 g of methyl 1-carbomethoxy-3,4,5-tris(3,4-dicarbomethoxycaffeoyl)quinate was obtained.

A mixture of 0.7 g of methyl 1-carbomethoxy-3,4,5-tris(3,4-dicarbomethoxycaffeoyl)quinate, 4.5 g of anhydrous lithium iodide, and 20 mL of pyridine was heated to reflux for 4 hours. After the mixture was left to cool naturally, the solvent was distilled off under reduced pressure, and the residue was purified by silica gel column chromatography (eluent: ethyl acetate/n-hexane) and ODS column chromatography. Thus, 0.15 g of 3,4,5-tricaffeoylquinic acid (TCQA) was obtained.

Synthesis Example 19

Synthesis of 3,4,5-tricaffeoylquinic acid ($9^{th}$)

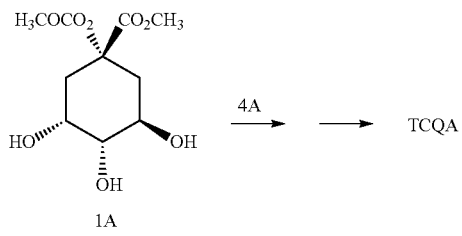

4A (6.3 g) synthesized as described above was added in small amounts to a mixture of 1A (1.32 g), 2.5 mL of pyridine, and 35 mL of toluene at room temperature. Thereafter, the mixture was heated to reflux for 5 hours at 80° C. After the mixture was left to cool naturally, the reaction liquid was poured into cold dilute hydrochloric acid, ethyl acetate was added thereto, and an organic layer was partitioned. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 1.7 g of methyl 1-carbomethoxy-3,4,5-tris(3,4-dicarbomethoxycaffeoyl)quinate was obtained.

A mixture of 1.7 g of methyl 1-carbomethoxy-3,4,5-tris(3,4-dicarbomethoxycaffeoyl)quinate, 8.5 g of anhydrous lithium iodide, and 30 mL of pyridine was heated to reflux for 5 hours. After the mixture was left to cool naturally, the solvent was distilled off under reduced pressure, and the residue was purified by silica gel column chromatography (eluent: ethyl acetate/n-hexane) and ODS column chromatography. Thus, 0.6 g of 3,4,5-tricaffeoylquinic acid (TCQA) was obtained.

Synthesis Example 20

Synthesis of (4D)

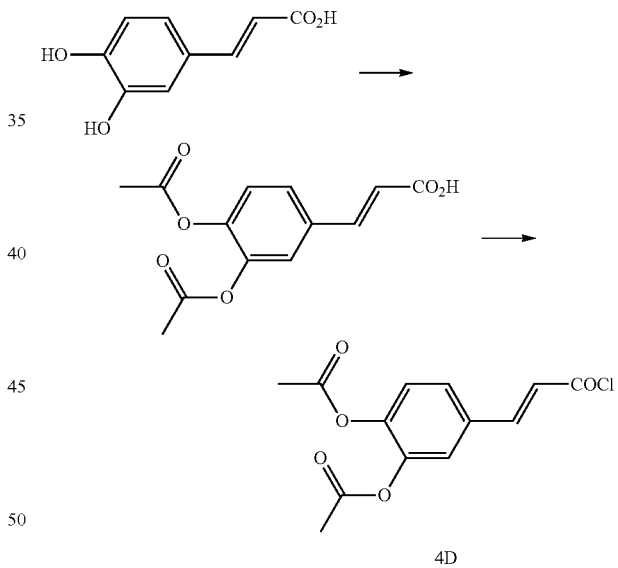

9.40 mL of acetic anhydride was added dropwise at 0° C. to a mixture of 7.20 g of caffeic acid, 20 mL of pyridine, and 0.12 g of 4-dimethylaminopyridine (DMAP), and then the mixture was stirred for 3 hours at room temperature. The reaction liquid was poured into ice, and was adjusted to pH 2 using hydrochloric acid at a concentration of 2 mol/L. Subsequently, extraction was performed three times using 80 mL of an ethyl acetate/tetrahydrofuran mixed solution [3/1 (v/v)], and then organic layers were combined and dried over anhydrous magnesium sulfate. The solvent was distilled off under reduced pressure, and then a solid obtained by adding n-hexane to the residue thus obtained was collected by filtration. Thus, 9.9 g of a white solid of 3,4-di-O-acetylcaffeic acid was obtained.

3.5 mL of oxalyl chloride was added dropwise at −10° C. to a mixture of 5.2 g of 3,4-di-O-acetylcaffeic acid thus obtained, 100 mL of toluene, and 0.1 g of N,N-dimethylformamide (DMF). The mixture was stirred for 3 hours at room temperature, and then the solvent was distilled off under reduced pressure. Subsequently, a solid precipitated by adding an ethyl acetate/n-hexane mixed solution [5/95 (v/v)] was collected by filtration, and thus 5.4 g of a pale yellow solid of 4D was obtained.

Synthesis Example 21

Synthesis of 3,4,5-tricaffeoylquinic acid 4D (2.87 g) synthesized as described above was added at −5° C. to 0° C. to a mixture of 0.50 g of quinic acid methyl ester, 1.15 mL of pyridine, and 20 mL of methylene chloride. After the mixture was stirred for 1 hour at −5° C. to 0° C., the temperature was raised to room temperature. The reaction liquid was poured into 1 N hydrochloric acid, ethyl acetate was added thereto, and an organic layer was extracted. The organic layer was washed with a saturated saline solution and dried over anhydrous magnesium sulfate, and then the solvent was distilled off under reduced pressure. Thus, 2.98 g of a residue was obtained. The residue was analyzed by $^1$H-NMR, and as a result, the purity of methyl 3,4,5-tris(3,4-di-O-acetylcaffeoyl)quinate included in the residue was 50% by weight, and the yield was 65%. To 100

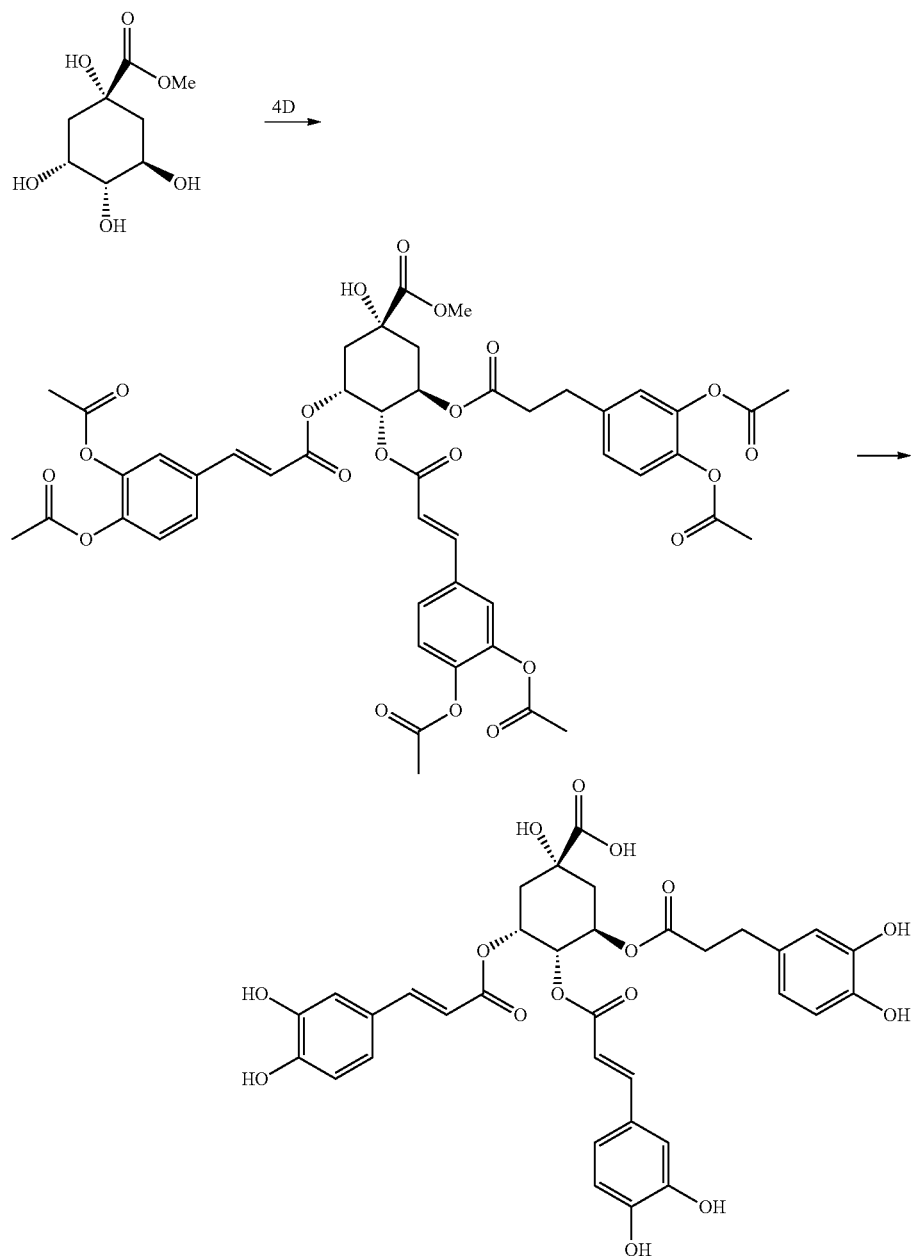

TCQA mg of this residue, a mixture of 5 mL of hydrochloric acid at 1 mol/L and 3 mL of tetrahydrofuran was added, and the mixture was stirred for 7 days at room temperature. The solvent was distilled off under reduced pressure. The residue was purified by silica gel column chromatography (eluent: ethyl acetate/n-hexane) and ODS column chromatography, and thus 7.0 mg of 3,4,5-tricaffeoylquinic acid (TCQA) was obtained.

Synthesis Example 22

Synthesis of (4A)

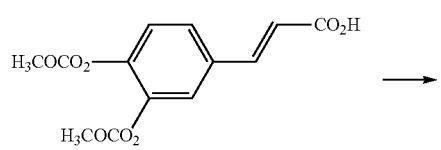

→

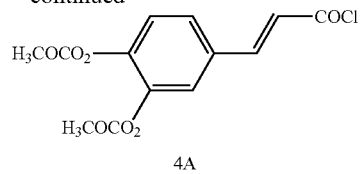

14.2 mL of thionyl chloride was added to a mixture of 48.08 g of dicarbomethoxycaffeic acid, 192 mL of toluene, and 0.15 mL of dimethylacetamide, and the mixture was heated and stirred for 1 hour at 50° C. The reaction liquid was ice-cooled, and then a solid precipitated therefrom was collected by filtration and was washed two times with 20 mL of toluene at 10° C. Thus, 44.7 g of a white solid of 4A was obtained.

Synthesis Example 23

Synthesis of 3,4,5-tricaffeoylquinic acid

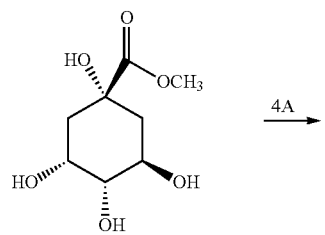 →4A→

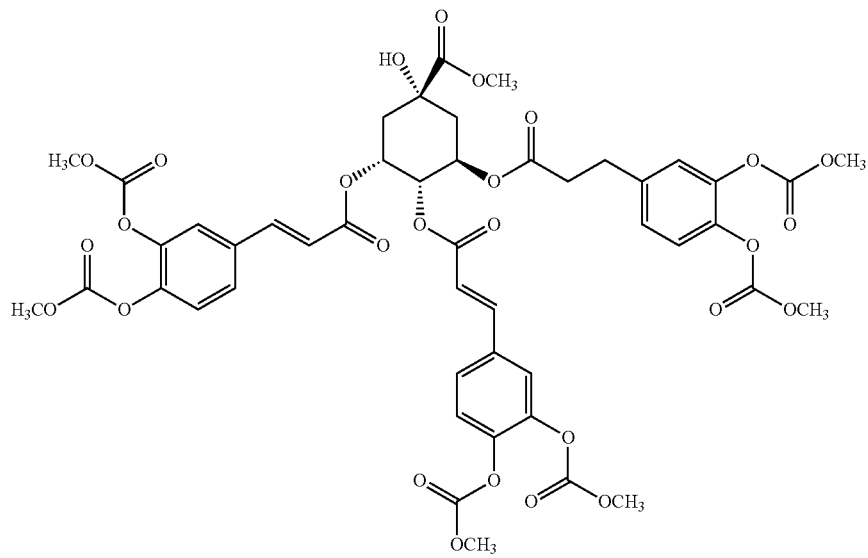

4A (1.70 g) synthesized in Synthesis Example 22 was added to a mixture of 0.31 g of quinic acid methyl ester, 0.65 mL of pyridine, and 10 mL of acetonitrile at 0° C. to 5° C. The mixture was stirred for 1 hour at 0° C. to 5° C., and then the temperature was raised to room temperature. Ethyl acetate and water were added to the reaction liquid, and an organic layer was extracted. The organic layer was washed with a saturated saline solution and dried over anhydrous magnesium sulfate, and then the solvent was distilled off under reduced pressure. Thus, 1.88 g of a residue was obtained. The residue was analyzed by $^{1}$H-NMR, and as a result, the purity of methyl 5-tris(3,4-di-O-carbomethoxycaffeoyl)quinate included in the residue was 50% by weight, and the yield was 60%.

3,4,5-Tricaffeoylquinic acid (TCQA) was obtained by the same method as that of Synthesis Example 11 described above, using the methyl 5-tris(3,4-di-O-carbomethoxycaffeoyl)quinate thus obtained, instead of methyl 1-carbomethoxy-3,4,5-tris(3,4-dicarbomethoxycaffeoyl)quinate.

Synthesis Example 24

Synthesis of 3,4,5-tricaffeoylquinic acid layer was washed with a saline solution and dried over anhydrous magnesium sulfate, and then the solvent was distilled off under reduced pressure. Thus, 1.81 g of a residue was obtained. The residue was analyzed by $^{1}$H-NMR, and as a result, the purity of methyl 1-carbomethoxy-3,4,5-tris(3,4-dicarbomethoxycaffeoyl)quinate included in the residue was 90% by mass, and the yield was 98%. The residue was purified by silica gel column chromatography (eluent: ethyl acetate/n-hexane), and thus 1.51 g of methyl 1-carbomethoxy-3,4,5-tris(3,4-dicarbomethoxycaffeoyl)quinate was obtained.

A mixture of 1.51 g of methyl 1-carbomethoxy-3,4,5-tris (3,4-dicarbomethoxycaffeoyl)quinate, 2.86 g of anhydrous lithium bromide, and 15 mL of pyridine was heated to reflux for 5 hours. After being left to cool naturally, the reaction liquid was poured into cold concentrated hydrochloric acid. Ethyl acetate was added thereto, and an organic layer was extracted. The organic layer was washed with a saline solution and dried over anhydrous magnesium sulfate, and then the solvent was distilled off under reduced pressure. The residue was purified by silica gel column chromatography (eluent: ethyl acetate/n-hexane) and ODS column chromatography, and thus 0.62 g of 3,4,5-tricaffeoylquinic acid (TCQA) was obtained.

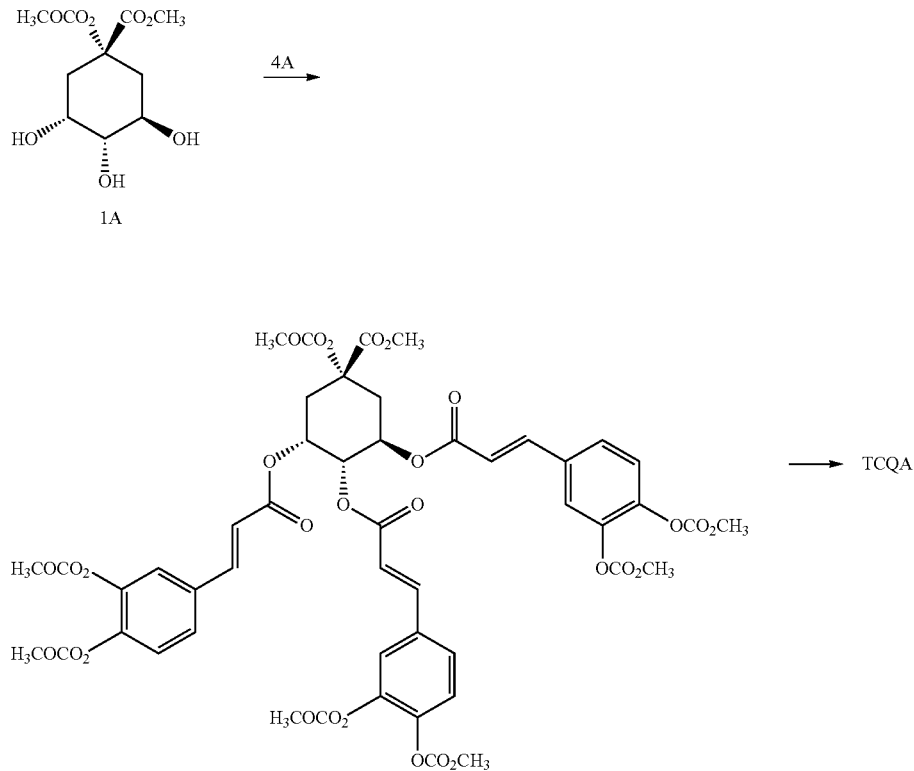

4A (1.56 g) synthesized in Synthesis Example 22 was added in small amounts to a mixture of 1A (0.40 g) synthesized in Synthesis Example 1, 0.6 mL of pyridine, and 4 mL of methylene chloride at −5° C. to 0° C. The mixture was stirred for 1 hour at −5° C. to 0° C. and for 30 minutes at room temperature, and then the reaction liquid was poured into cold dilute hydrochloric acid. Ethyl acetate was added thereto, and an organic layer was extracted. The organic Meanwhile, as can be seen from a comparison with Synthesis Example 23, in the case of the present Synthesis Example 24 using a compound represented by Formula (1A) in which $R^1$ is a hydroxyl protective group and $R^2$ is a carboxyl protective group, the purity of the product obtained after the reaction with a compound represented by Formula (4A) (methyl 1-carbomethoxy-3,4,5-tris(3,4-dicarbomethoxycaffeoyl)quinate) was higher.

Synthesis Example 25

Synthesis of 3,4,5-tricaffeoylquinic acid

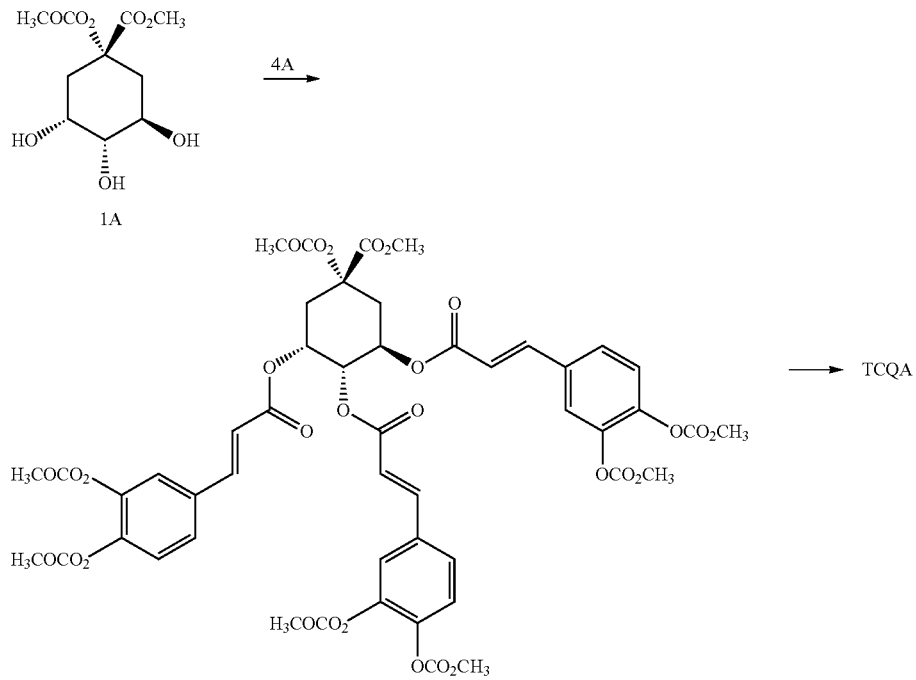

4A (1.56 g) synthesized in Synthesis Example 22 was added in small amounts to a mixture of 1A (0.40 g) synthesized in Synthesis Example 1, 0.6 mL of pyridine, and 4 mL of acetonitrile at −5° C. to 0° C. The mixture was stirred for 1 hour at −5° C. to 0° C. and for 30 minutes at room temperature, and then the reaction liquid was poured into cold dilute hydrochloric acid. Ethyl acetate was added thereto, and an organic layer was extracted. The organic layer was washed with a saline solution and dried over anhydrous magnesium sulfate, and then the solvent was distilled off under reduced pressure. Thus, 1.79 g of a residue was obtained. The residue was analyzed by $^1$H-NMR, and as a result, the purity of methyl 1-carbomethoxy-3,4,5-tris(3,4-dicarbomethoxycaffeoyl)quinate included in the residue was 91% by weight, and the yield was 98%. The residue was purified by silica gel column chromatography (eluent: ethyl acetate/n-hexane), and thus 1.58 g of methyl 1-carbomethoxy-3,4,5-tris(3,4-dicarbomethoxycaffeoyl)quinate was obtained.

A mixture of 1.58 g of methyl 1-carbomethoxy-3,4,5-tris (3,4-dicarbomethoxycaffeoyl)quinate, 2.86 g of anhydrous lithium bromide, and 15 mL of pyridine was heated to reflux for 5 hours. After the mixture was left to cool naturally, the reaction liquid was poured into cold concentrated hydrochloric acid. Ethyl acetate was added thereto, and an organic layer was extracted. The organic layer was washed with a saline solution and dried over anhydrous magnesium sulfate, and then the solvent was distilled off under reduced pressure. The residue was purified by silica gel column chromatography (eluent: ethyl acetate/n-hexane) and ODS column chromatography, and thus 0.65 g of 3,4,5-tricaffeoylquinic acid (TCQA) was obtained.

Synthesis Example 26

Synthesis of 3,4,5-tricaffeoylquinic acid

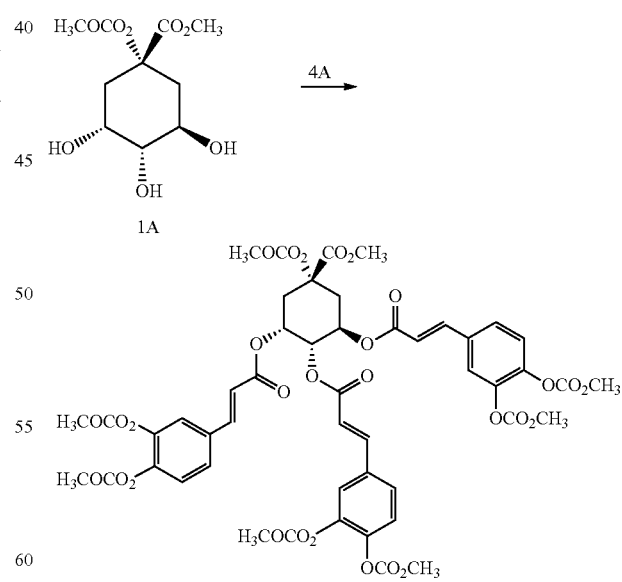

4A (1.04 g) synthesized in Synthesis Example 22 was added in small amounts to a mixture of 1A (0.26 g) synthesized in Synthesis Example 1 and 4 mL of acetonitrile at room temperature. After being heated to reflux for 5 hours, the reaction liquid was cooled to room temperature, and was poured into cold dilute hydrochloric acid. Ethyl acetate was added thereto, and an organic layer was extracted. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 0.88 g of methyl 1-carbomethoxy-3,4,5-tris(3,4-dicarbomethoxycaffeoyl)quinate was obtained.

3,4,5-Tricaffeoylquinic acid (TCQA) was obtained by the same procedure as that of Synthesis Example 25, using the methyl 1-carbomethoxy-3,4,5-tris(3,4-di carbomethoxycaffeoyl)quinate thus obtained.

Synthesis Example 27

Synthesis of 3,4,5-tricaffeoylquinic acid

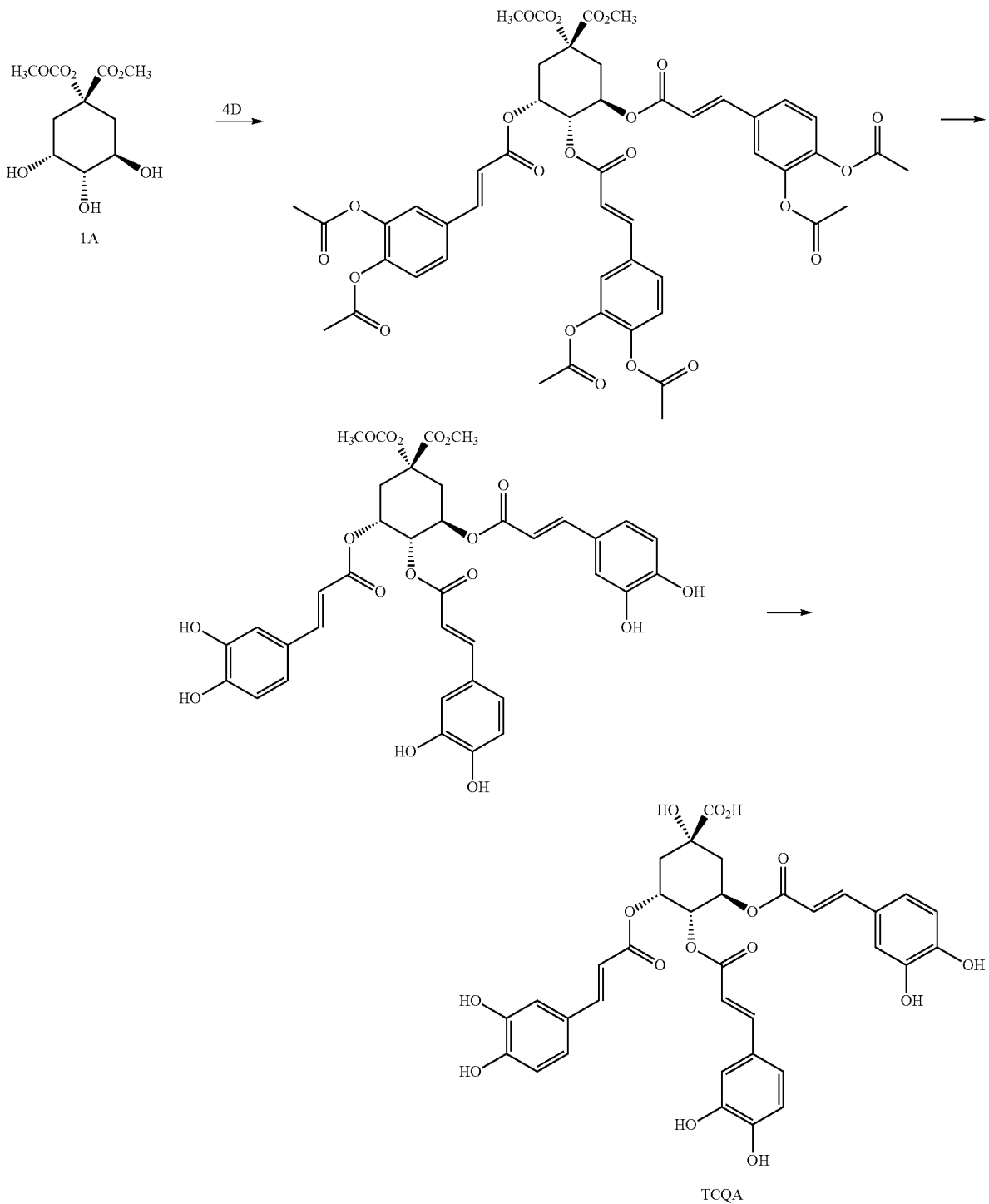

4D (37.0 g) synthesized in Synthesis Example 20 was added in small amounts to a mixture of 1A (9.62 g) synthesized in Synthesis Example 1, 15.8 mL of pyridine, and 96 mL of acetonitrile at −5° C. to 0° C. After being stirred for 1 hour at 0° C. to 5° C., the reaction liquid was poured into cold dilute hydrochloric acid. Ethyl acetate was added thereto, and an organic layer was extracted. The organic layer was washed with a saline solution and dried over anhydrous magnesium sulfate, and then the solvent was distilled off under reduced pressure. Thus, 38.9 g of a residue was obtained. The residue was analyzed by $^1$H-NMR, and as a result, the purity of methyl 1-carbomethoxy-3,4,5-tris(3,4-diacetylcaffeoyl)quinate included in the residue was 92% by weight, and the yield was 98%. The residue was purified by silica gel column chromatography (eluent: ethyl acetate/n-hexane), and thus 34.7 g of methyl 1-carbomethoxy-3,4,5-tris(3,4-diacetylcaffeoyl)quinate was obtained.

10.46 g of lithium hydroxide was added in small amounts to a mixture of 34.7 g of methyl 1-carbomethoxy-3,4,5-tris(3,4-diacetylcaffeoyl)quinate, 96 mL of acetonitrile, and 150 mL of water at 10° C. to 20° C. The mixture was stirred overnight at room temperature, and then 50 mL of concentrated hydrochloric acid was added in small amounts to the reaction liquid at 10° C. to 20° C. Ethyl acetate was added thereto, and an organic layer was extracted. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 24.1 g of methyl 1-carbomethoxy-3,4,5-tricaffeoylquinate was obtained.

A mixture of 24.1 g of methyl 1-carbomethoxy-3,4,5-tricaffeoylquinate, 32.3 g of anhydrous lithium bromide, and 200 mL of pyridine was heated to reflux for 9 hours. After being left to cool naturally, the reaction liquid was poured into cold concentrated hydrochloric acid. Ethyl acetate was added thereto, and an organic layer was extracted. The organic layer was washed with a saline solution and dried over anhydrous magnesium sulfate, and then the solvent was distilled off under reduced pressure. The residue was purified by silica gel column chromatography (eluent: ethyl acetate/n-hexane) and ODS column chromatography, and thus 9.28 g of 3,4,5-tricaffeoylquinic acid (TCQA) was obtained.

Synthesis Example 28

Synthesis of 3,4,5-tricaffeoylquinic acid

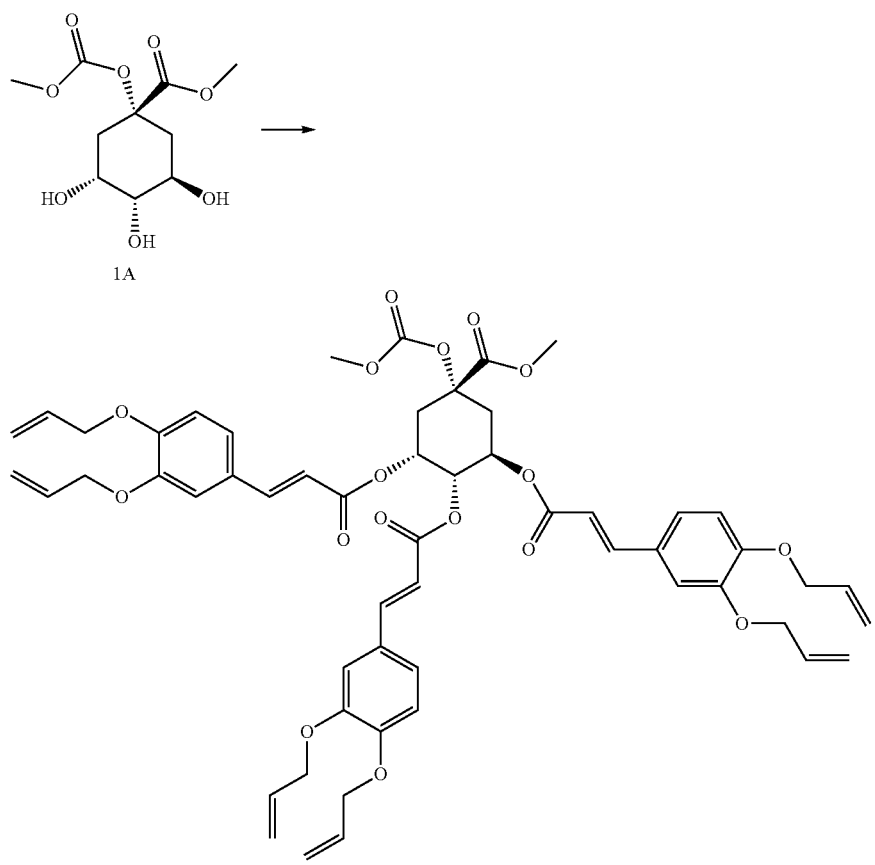

Figure 10:
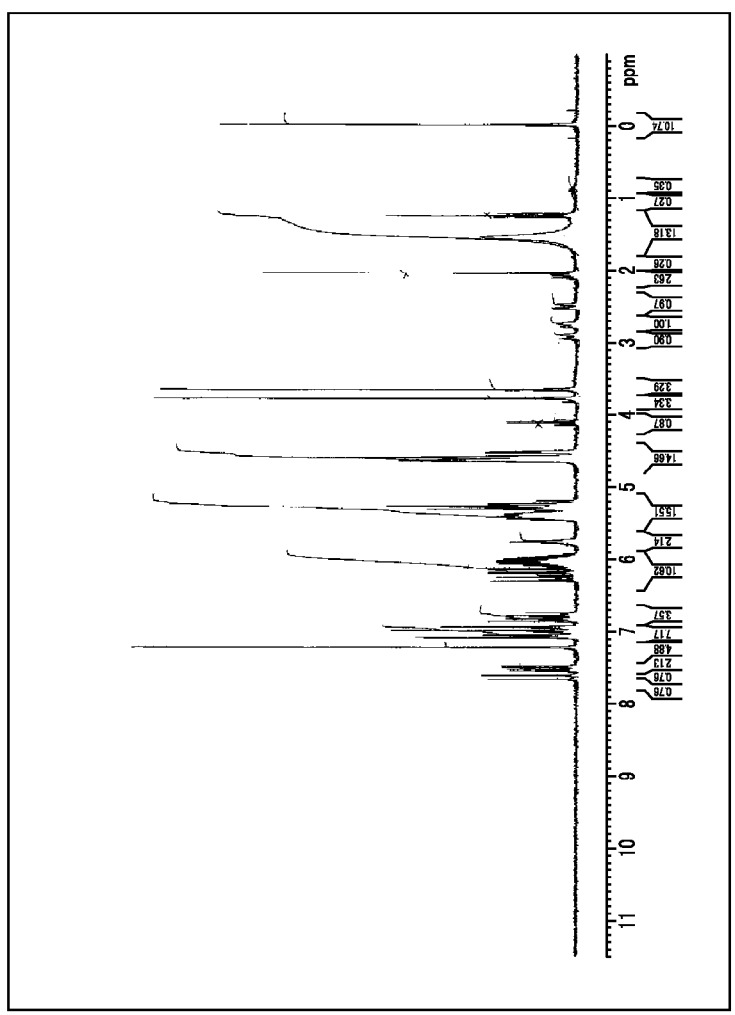
FIG. 10 is the $^1$H-NMR spectrum of methyl 1-carbomethoxy-3,4,5-tris(3,4-diallylcaffeoyl)quinate synthesized in Synthesis Example 28.

In a nitrogen atmosphere, a mixture of 1A (200 mg) synthesized in Synthesis Example 1, methylene chloride (10 mL), and pyridine (0.30 mL) was cooled to 0° C., and while the mixture was stirred, 3,4-di-O-allylcaffeic acid chloride was added thereto. The temperature was raised to room temperature, and then the reaction mixture was partitioned by adding ethyl acetate and 1 mol/L hydrochloric acid. Subsequently, the organic layer was washed with a saturated saline solution, and was dried over magnesium sulfate. After filtering the organic layer, the solvent was distilled off, and the residue was purified by silica gel column chromatography (eluent: n-hexane/ethyl acetate=1/1 (v/v)). Thus, methyl 1-carbomethoxy-3,4,5-tris(3,4-diallylcaffeoyl)quinate (291 mg) was obtained. The ¹H-NMR spectrum (solvent: CDCl₃) is presented in FIG. 10.

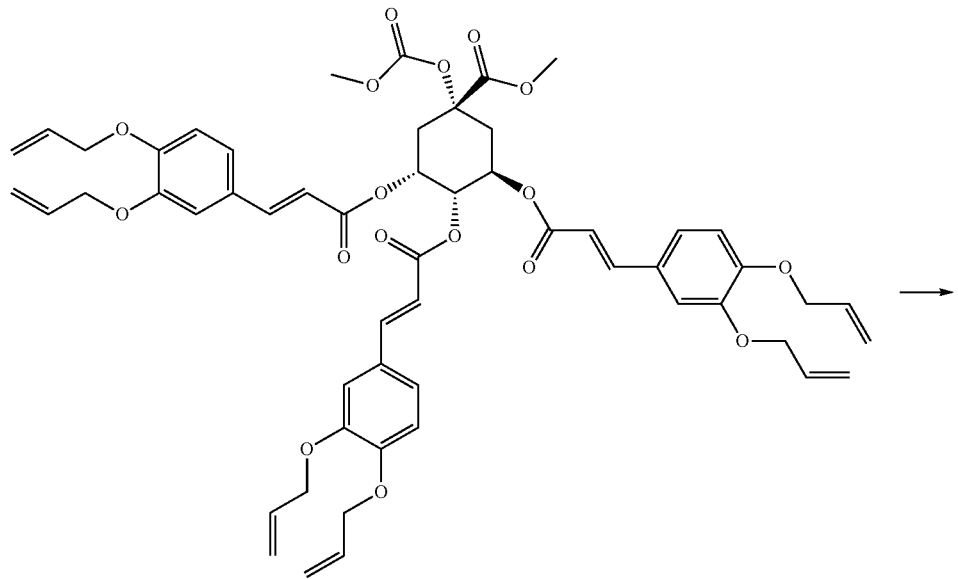

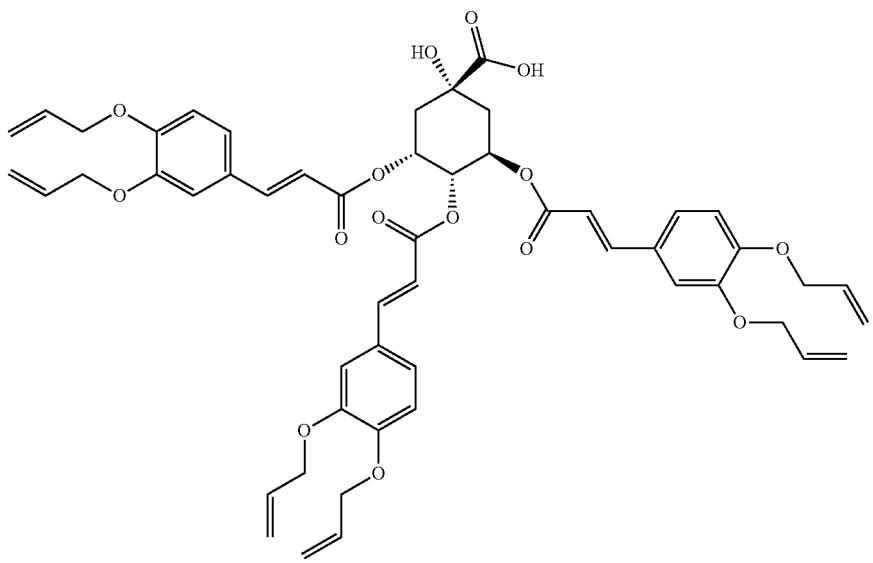

Figure 11:
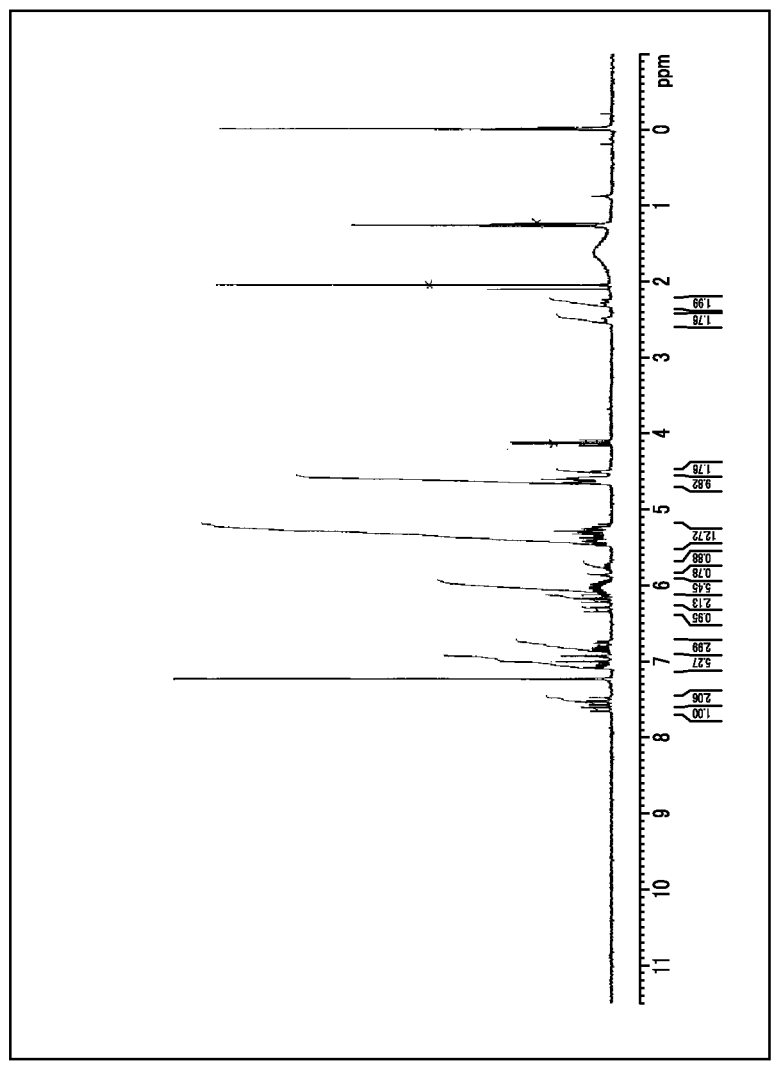
FIG. 11 is the $^1$H-NMR spectrum of 3,4,5-tris(3,4-diallylcaffeoyl)quinic acid synthesized in Synthesis Example 28.

In a nitrogen atmosphere, a mixture of methyl 1-carbomethoxy-3,4,5-tris(3,4-diallylcaffeoyl)quinate (200 mg), pyridine (4 mL), and lithium iodide (324 mg) was stirred for 6 hours at 100° C. After the mixture was cooled to room temperature, ethyl acetate and 1 mol/L hydrochloric acid were added thereto, and concentrated hydrochloric acid was further added thereto until the pH value of the aqueous layer reached 2. The organic layer and the aqueous layer were partitioned, and the aqueous layer was further extracted with ethyl acetate two more times. The organic layers thus obtained were combined and dried over magnesium sulfate, and then filtration and concentration were carried out. A residue thus obtained was purified by silica gel column chromatography (eluent: n-hexane/ethyl acetate=2/3 (v/v)) using CHROMATOREX (SO3H) manufactured by Fuji Silysia Chemical, Ltd. as a column packing agent, and thus 3,4,5-tris(3,4-diallylcaffeoyl)quinic acid (122 mg) was obtained. The ¹H-NMR spectrum (solvent: CDCl₃) is presented in FIG. 11.

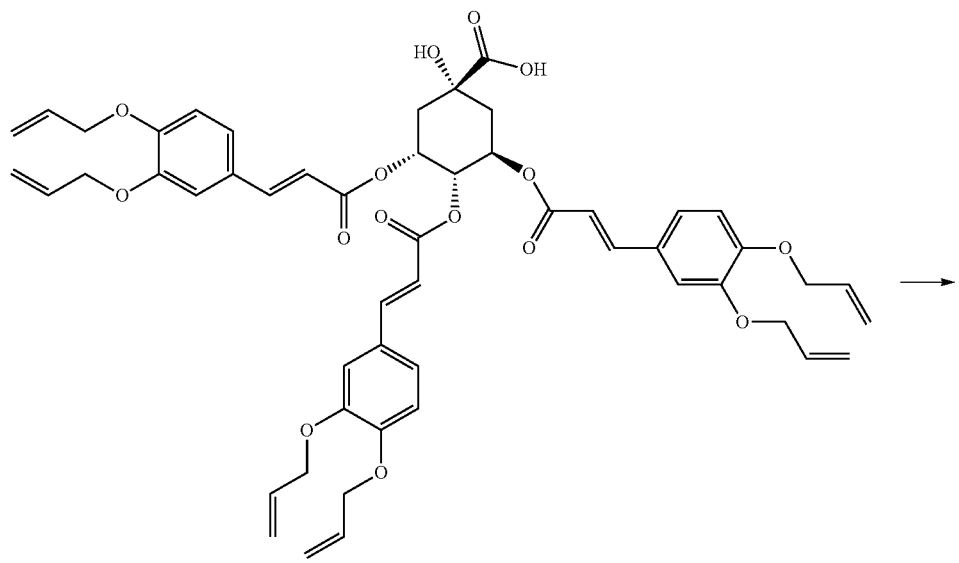

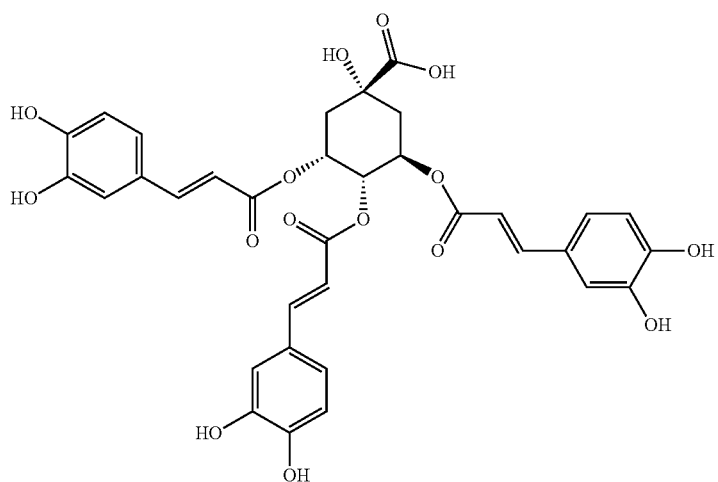

In a nitrogen atmosphere, a mixture of 3,4,5-tris(3,4-diallylcaffeoyl)quinic acid (60 mg), tetrahydrofuran (3.5 mL), tetrakis(triphenylphosphine)palladium (3.8 mg), and morpholine (341 mg) was stirred for 4 hours at room temperature. After the mixture was cooled to room temperature, ethyl acetate and 1 mol/L hydrochloric acid were added thereto, and concentrated hydrochloric acid was further added thereto until the pH value of the aqueous layer reached 2. An organic layer and an aqueous layer were partitioned, and the aqueous layer was further extracted with ethyl acetate two more times. The organic layers thus obtained were combined and dried over magnesium sulfate, and then filtration and concentration were carried out. A residue thus obtained was purified by silica gel column chromatography (eluent: ethyl acetate/methanol=5/1 (v/v)), and thus TCQA (6.8 mg) was obtained.

Synthesis Example 29

Synthesis of 1-O-carbomethoxy-3,4-O-isopropylidene-1,5-quinide lactone

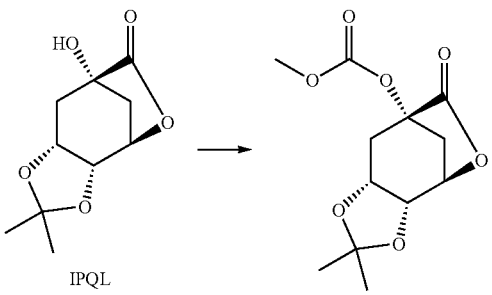 [SMILES: CC1(C)O[C@H]2[C@H]3C[C@@](O)(C[C@H]2O1)C(=O)O3 ; COC(=O)O[C@@]12C[C@@H](OC1=O)[C@@H]1OC(C)(C)O[C@@H]1C2]

In a nitrogen atmosphere, a mixture of 3,4-O-isopropylidene-1,5-quinide lactone (IPQL) (21.4 g), methylene chloride (214 mL), and tetramethylethylenediamine (TMEDA) (13.9 g) was cooled to −12° C. while being stirred. Methyl chloroformate (18.9 g) was added dropwise thereto over 15 minutes. After completion of dropwise addition, the temperature was raised to room temperature, and stirring was continued for 2 hours. The reaction mixture was partitioned by adding 70 mL of 1 mol/L hydrochloric acid thereto, and then the organic layer was washed with a mixed liquid of 40 mL of a saturated saline solution and 10 mL of a saturated aqueous solution of sodium hydrogen carbonate, and was dried over magnesium sulfate. After filtration, 100 mL of hexane was added thereto, and the solvent was distilled off until the mass reached 70 g. Crystals precipitated therefrom were filtered and dried under reduced pressure, and thus 1-O-carbomethoxy-3,4-O-isopropylidene-1,5-quinide lactone (24.8 g) was obtained as white crystals.

Synthesis Example 30

Synthesis of 1A

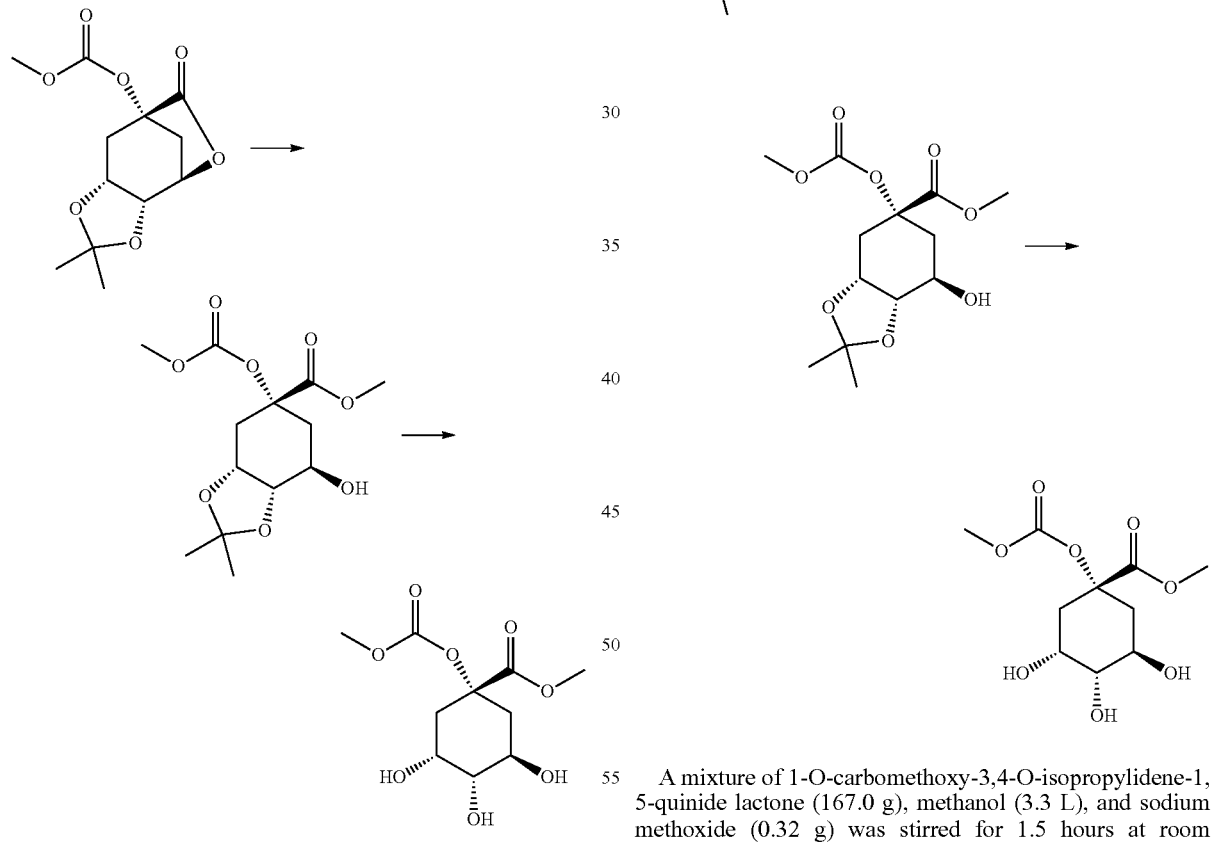

A mixture of 1-O-carbomethoxy-3,4-O-isopropylidene-1,5-quinide lactone (40 g), methanol (1.6 L), and sodium hydrogen carbonate (14.8 g) was stirred for 1 hour at room temperature. The mixture was cooled to obtain an internal temperature of 6° C., 40 g of sodium sulfate was added thereto, and concentrated sulfuric acid (10.8 g) was further added dropwise thereto. After 1 hour, the temperature was raised to room temperature, and stirring was continued for 5 hours. Sodium hydrogen carbonate (3.7 g) was added to the reaction mixture, and the mixture was thoroughly stirred. Subsequently, insoluble materials were filtered, and methanol was distilled off. Ethyl acetate (600 mL) and sodium hydrogen carbonate (98 g) were added to the residue, and the mixture was stirred for 1 hour at room temperature. A solid was filtered, ethyl acetate was distilled off, and then a solid precipitated out by adding methyl tert-butyl ether was filtered and dried under reduced pressure. Thus, 1A (33.9 g) was obtained as white crystals.

Synthesis Example 31

Synthesis of 1A

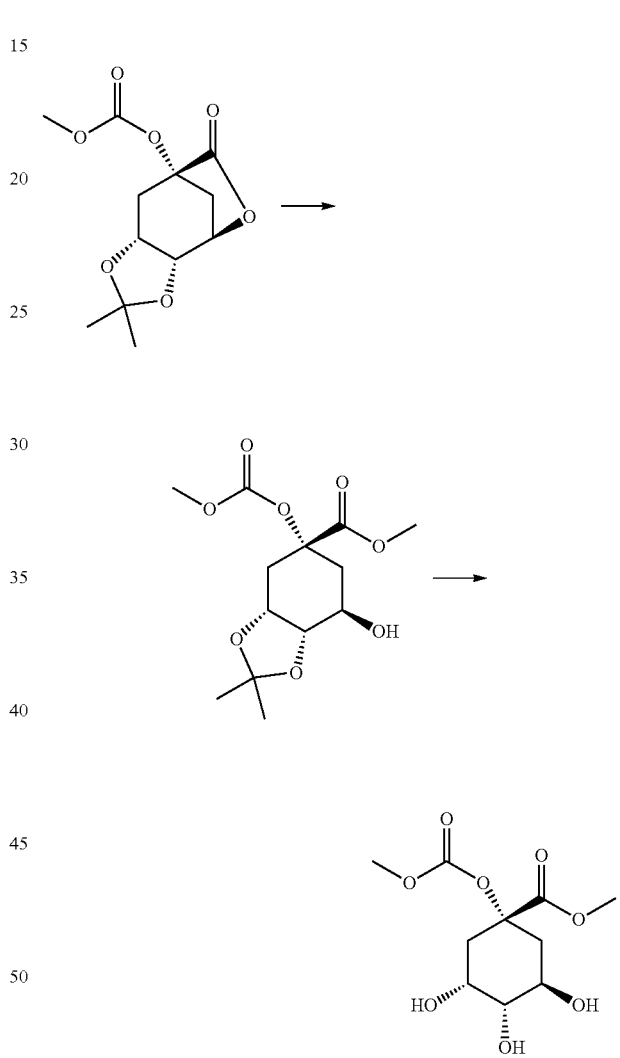

A mixture of 1-O-carbomethoxy-3,4-O-isopropylidene-1,5-quinide lactone (167.0 g), methanol (3.3 L), and sodium methoxide (0.32 g) was stirred for 1.5 hours at room temperature. The mixture was cooled to obtain an internal temperature of 6° C., and concentrated sulfuric acid (9.32 g) was added dropwise thereto. After one hour, the temperature was raised to room temperature, and stirring was continued for 5 hours. The reaction mixture was neutralized by adding sodium methoxide thereto, and then methanol was distilled off. A solid precipitated out by adding ethyl acetate and methyl tert-butyl ether to the residue was filtered and dried under reduced pressure, and thereby 1A (100 g) was obtained as white crystals.

Synthesis Example 32

Synthesis of 3,4,5-tricaffeoylquinic acid

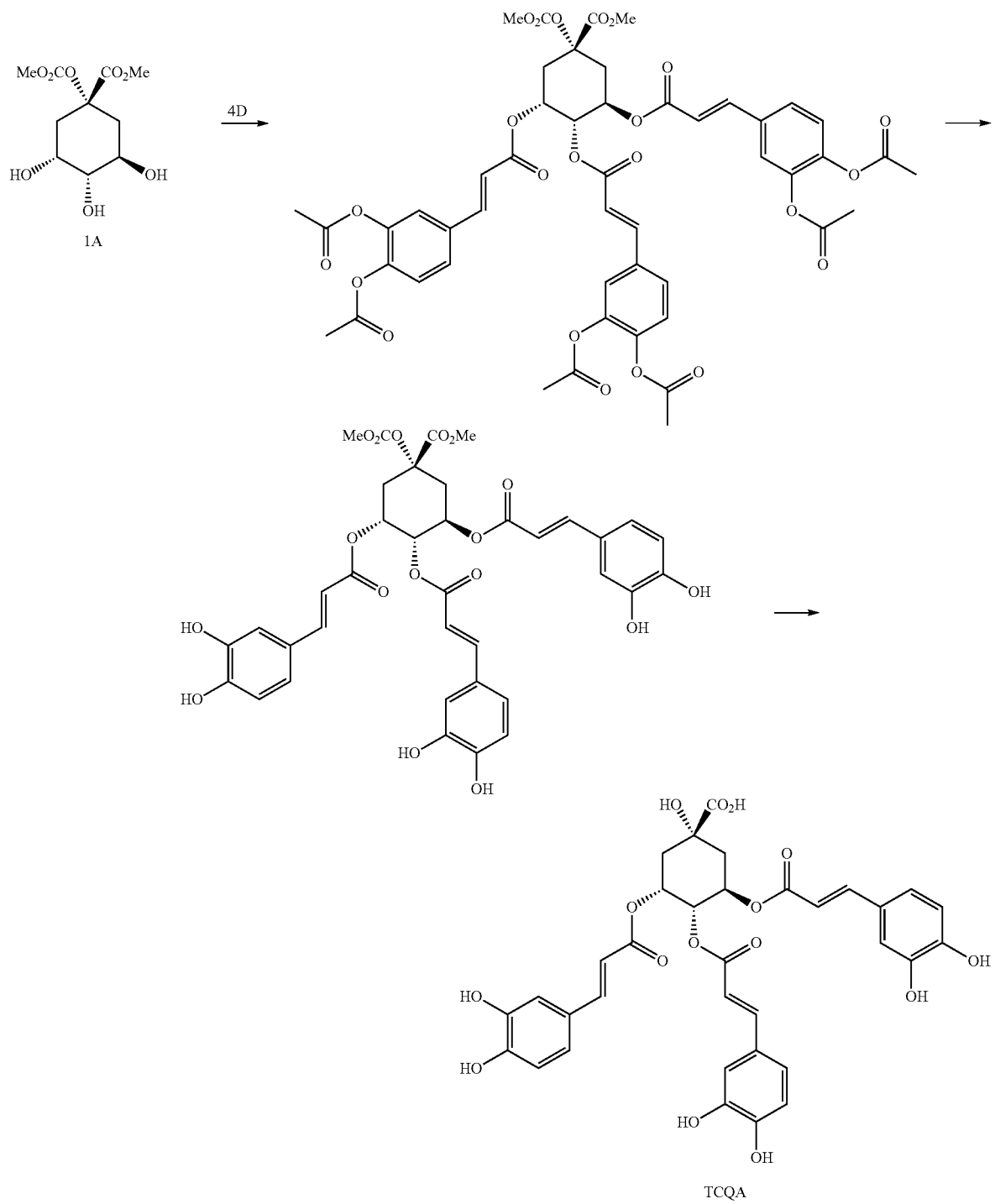

4D (213.7 g) synthesized in Synthesis Example 22 was added in small amounts to a mixture of 1A (55.5 g) synthesized in Synthesis Example 1, 91.3 mL of pyridine, and 333 mL of acetonitrile at −5° C. to 0° C. After being stirred for 1.5 hours at room temperature, the reaction liquid was poured into cold dilute hydrochloric acid. Ethyl acetate was added thereto, and an organic layer was extracted. The organic layer was washed with a saline solution and dried over anhydrous magnesium sulfate, and then the solvent was distilled off under reduced pressure. Thus, 224.4 g of a residue was obtained. The residue was analyzed by ¹H-NMR, and as a result, the purity of methyl 1-carbomethoxy-3,4,5-tris(3,4-diacetylcaffeoyl)quinate included in the residue was 92% by weight, and the yield was 98%.

To a mixture of 20.3 g of the residue obtained here and 38 mL of acetonitrile, 11.2 mL of hydrazine monohydrate was added in small amounts at 10° C. to 25° C. After the mixture was stirred for 1.5 hours at room temperature, 21 mL of concentrated hydrochloric acid was added in small amounts to the reaction liquid at 0° C. to 10° C. Ethyl acetate was added thereto, and an organic layer was extracted. The organic layer was washed with a saline solution and dried over anhydrous magnesium sulfate, and then the solvent was distilled off under reduced pressure. The residue was purified by silica gel column chromatography (eluent: ethyl acetate/n-hexane), and thus 12.2 g of methyl 1-carbomethoxy-3,4,5-tricaffeoylquinate was obtained.

A mixture of 7.51 g of methyl 1-carbomethoxy-3,4,5-tricaffeoylquinate, 15.6 g of anhydrous lithium bromide, 4.80 g of pyridine hydrobromide, and 45 mL of pyridine was heated to reflux for 1.5 hours. After being left to cool naturally, the reaction liquid was poured into cold concentrated hydrochloric acid. Ethyl acetate was added thereto, and an organic layer was extracted. The organic layer was washed with a saline solution and dried over anhydrous magnesium sulfate, and then the solvent was distilled off under reduced pressure. The residue was purified by silica gel column chromatography (eluent: ethyl acetate/n-hexane) and ODS column chromatography, and thus 6.0 g of 3,4,5-tricaffeoylquinic acid (TCQA) was obtained.

Comparative Example

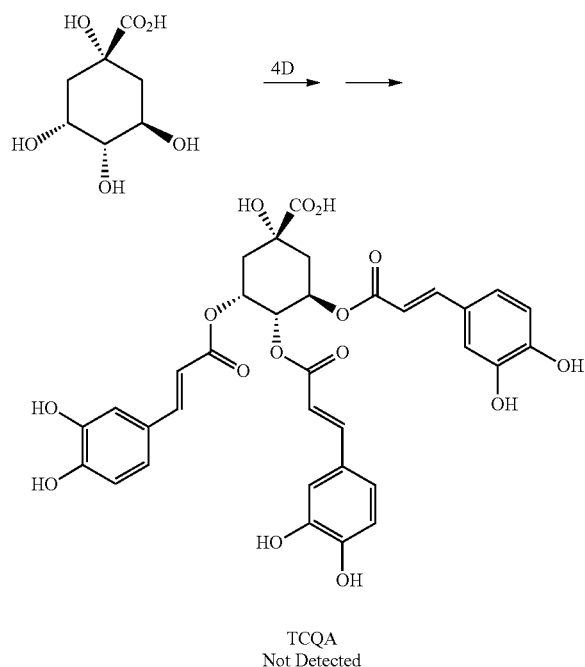

4D (0.650 g) synthesized in Synthesis Example 20 was added in small amounts to a mixture of quinic acid (0.096 g), 0.27 mL of pyridine, and 3 mL of acetonitrile at −5° C. to 0° C. After being stirred for 1 hour at 0° C. to 5° C., the reaction liquid was poured into cold dilute hydrochloric acid. Ethyl acetate was added thereto, and an organic layer was extracted. The organic layer was washed with a saline solution and dried over anhydrous magnesium sulfate, and then the solvent was distilled off under reduced pressure. 4 mL of acetonitrile and 6 mL of water were added to the residue. 0.144 g of lithium hydroxide was added in small amounts to the mixture at 10° C. to 20° C. After the mixture was stirred overnight at room temperature, dilute hydrochloric acid was added in small amounts to the reaction liquid at 10° to 20° C., and thus the reaction liquid was acidified. Ethyl acetate was added thereto, and an organic layer was extracted. The organic layer was washed with a saline solution and dried over anhydrous magnesium sulfate, and then the solvent was distilled off under reduced pressure. The residue was analyzed by high performance liquid chromatography; however, 3,4,5-tricaffeoylquinic acid was not detectable.

What is claimed is:

1. A method for manufacturing 3,4,5-tricaffeoylquinic acid, the method comprising at least Step (1) of allowing a compound represented by Formula (1) or a compound represented by Formula (2) to react with a compound represented by Formula (4); and Step (2) of deprotecting the product obtained in Step (1), and producing 3,4,5-tricaffeoylquinic acid represented by Formula (6):

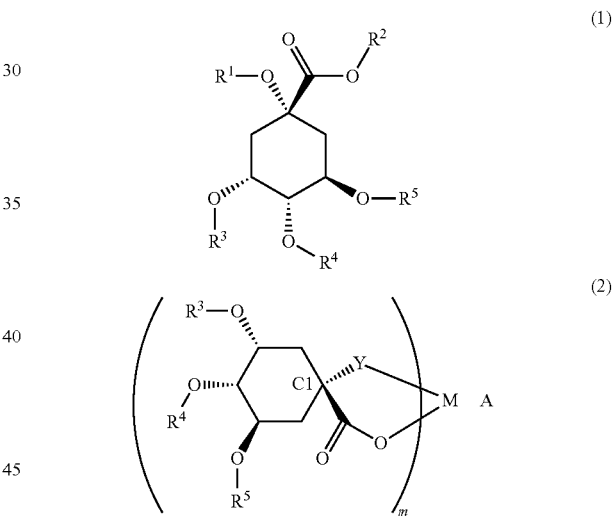

where in Formula (1), $R^1$ represents a hydrogen atom or a hydroxyl protective group; $R^2$ represents a hydrogen atom or a carboxyl protective group; at least one of $R^1$ and $R^2$ is not a hydrogen atom or $R^1$ and $R^2$ are joined together to form a protective group represented by —B($R^a$)—; $R^a$ represents a $C_{1-6}$ alkyl group which may be substituted, an aryl group which may be substituted, or a $C_{1-6}$ alkoxy group which may be substituted; and $R^3$, $R^4$ and $R^5$, which are identical or different, each represent a hydrogen atom or a group represented by Formula (3), in Formula (2), Y represents $*_1$-$OR^b$; $R^b$ either does not exist or represents a hydrogen atom; $*_1$ represents the position of bonding to a carbon atom represented by C1; A either does not exist or represents a monovalent cation; M represents a boron atom, a silicon atom, a divalent metal ion, or a trivalent metal ion; and m represents an integer of 2 or 3, when M is a boron atom, m represents 2, and A represents a monovalent cation; when M is a silicon atom, m represents 2, and A does not exist; when M is a divalent metal ion, m represents 2, and A does not exist; and when M is a trivalent metal ion, m represents 3, and A does not exist, and at least one of R³, R⁴, and R⁵ represents a hydrogen atom:

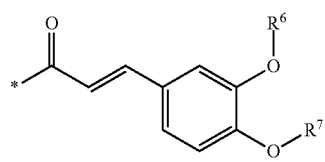

(3)

where in Formula (3), R⁶ and R⁷, which are identical or different, each represent a phenolic hydroxyl protective group; or R⁶ and R⁷ are joined together to form a protective group selected from the group consisting of a carbonyl group (—CO—) and a methylene group which may be substituted; and * represents the position of bonding to an oxygen atom of the compound represented by Formula (1), and

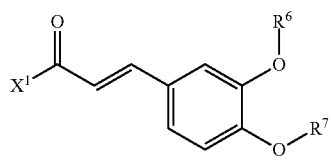

(4)

where in Formula (4), X¹ represents a hydroxyl group or a leaving group; and R⁶ and R⁷ have the same meanings as described above,

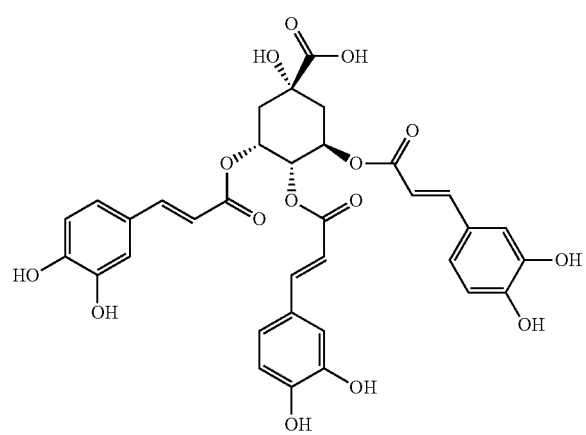

(6)

wherein a compound represented by Formula (1a) is used in the Step (1), and the method comprises, before the Step (1), Step (3) of allowing a compound represented by Formula (A3) to react with a compound represented by Formula (A5), and thereby obtaining the compound represented by Formula (1a):

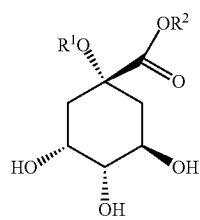

(1a)

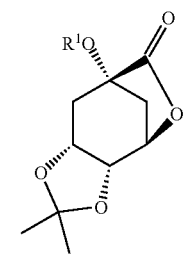

(A3)

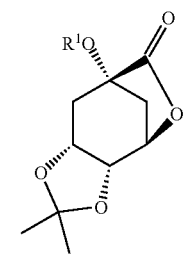

R²OH   (A5)

where in Formula (1a) and Formula (A3), R1 represents a hydrogen atom or a hydroxyl protective group; and in Formula (1a) and Formula (A5), R2 represents a hydrogen atom or a carboxyl protective group, provided that at least one of R1 and R2 is not a hydrogen atom.

2. The method according to claim 1, wherein Step (1) is carried out in the presence of a solvent having an SP value of 8.0 to 10.0.

3. The method according to claim 1, wherein the temperature of the reaction for Step (1) is −10° C. to 30° C.

4. The method according to claim 1, wherein X¹ represents a halogen atom.

5. The method according to claim 1, wherein X¹ represents a chlorine atom.

6. The method according to claim 1, wherein R¹ is a hydroxyl protective group, and R² is a carboxyl protective group.

7. The method according to claim 1, wherein
R¹ represents a $C_{1-6}$ alkoxycarbonyl group which may be substituted, an aryloxycarbonyl group which may be substituted, or an acyl group which may be substituted; and
R² represents a $C_{1-6}$ alkyl group which may be substituted, or a $C_{2-6}$ alkenyl group which may be substituted.

8. The method according to claim 1, wherein
R¹ represents a $C_{1-6}$ alkoxycarbonyl group which may be substituted with a halogen atom; and
R² represents a $C_{1-6}$ alkyl group which may be substituted with a halogen atom.

9. The method according to claim 1, wherein R⁶ and R⁷, which are identical or different, each represent a $C_{1-6}$ alkoxycarbonyl group which may be substituted, an aryloxycarbonyl group which may be substituted, or an acyl group which may be substituted.

10. The method according to claim 1, wherein R⁶ and R⁷, which are identical or different, each represent a $C_{1-6}$ alkoxycarbonyl group which may be substituted with a halogen atom.

11. The method according to claim 1, wherein R³, R⁴, and R⁵ are hydrogen atoms.

12. The method according to claim 2, wherein the temperature of the reaction for Step (1) is −10° C. to 30° C.

13. The method according to claim 2, wherein a compound represented by Formula (1a) is used in the Step (1), and the method comprises, before the Step (1), Step (3) of allowing a compound represented by Formula (A3) to react with a compound represented by Formula (A5), and thereby obtaining the compound represented by Formula (1a):

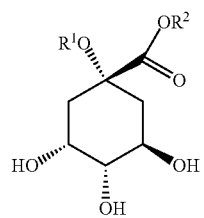

(1a)

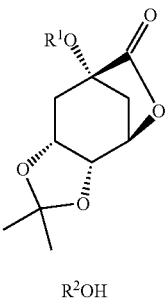

(A3)

R²OH (A5)

where in Formula (Ia) and Formula (A3), $R^1$ represents a hydrogen atom or a hydroxyl protective group; and in Formula (Ia) and Formula (A5), $R^2$ represents a hydrogen atom or a carboxyl protective group, provided that at least one of $R^1$ and $R^2$ is not a hydrogen atom.

* * * * *